US012773277B2

(12) United States Patent
Ghanam et al.

(10) Patent No.: US 12,773,277 B2
(45) Date of Patent: Oct. 27, 2026

(54) SYSTEMS AND METHODS FOR CALIBRATING A TRACKING ARRAY

(71) Applicant: Stryker European Operations Limited, Carrigtwohill (IE)

(72) Inventors: Fadi Ghanam, Schallstadt (DE); James G. Walen, Portage, MI (US); Clifford Edwin Lambarth, Portage, MI (US); Caleb Gossens, Ravenna, MI (US)

(73) Assignee: Stryker European Operations Limited, Carrigtwohill (IE)

( * ) Notice: Subject to any disclaimer, the term of this patent is extended or adjusted under 35 U.S.C. 154(b) by 169 days.

(21) Appl. No.: 18/784,228

(22) Filed: Jul. 25, 2024

(65) Prior Publication Data

US 2024/0374324 A1 Nov. 14, 2024

Related U.S. Application Data

(63) Continuation of application No. 17/219,067, filed on Mar. 31, 2021, now Pat. No. 12,064,190, which is a
(Continued)

(51) Int. Cl.
*A61B 34/20* (2016.01)
*A61B 90/00* (2016.01)
*G06T 7/20* (2017.01)

(52) U.S. Cl.
CPC .............. *A61B 34/20* (2016.02); *A61B 90/39* (2016.02); *G06T 7/20* (2013.01);
(Continued)

(58) Field of Classification Search
CPC . A61B 34/20; A61B 90/39; A61B 2034/2055; A61B 2034/2072;
(Continued)

(56) References Cited

U.S. PATENT DOCUMENTS 6,081,741 A 6/2000 Hollis
8,597,316 B2 12/2013 McCombs
(Continued)

FOREIGN PATENT DOCUMENTS

CN 107405170 A 11/2017
CN 108535734 A 9/2018
(Continued)

OTHER PUBLICATIONS

English language abstract and machine-assisted English translation for CN 108535734 A extracted from espacenet.com database on Aug. 30, 2024, 15 pages.
(Continued)

*Primary Examiner* — Christopher M Brandt
(74) *Attorney, Agent, or Firm* — Howard & Howard Attorneys PLLC

(57) ABSTRACT

A navigation system for navigating a medical instrument is provided. The system includes a localizer, a tracking array, and a processor. The tracking array has a first tracking face and a second tracking face which are coupled to one another and collectively include a plurality of optical tracking elements. The processor is configured to measure relative positions of the plurality of optical tracking elements while visible to the localizer, measure relative positions of the at least one optical tracking element of the first tracking face and at least one optical tracking element of the second tracking face while visible to the localizer at the same time, and create a composite rigid body based on the measured relative positions of at least one optical tracking element of the first tracking face and the at least one optical tracking element of the second tracking face while visible at the same time.

20 Claims, 32 Drawing Sheets

Related U.S. Application Data continuation-in-part of application No. PCT/IB2020/059064, filed on Sep. 28, 2020.

(60) Provisional application No. 62/906,629, filed on Sep. 26, 2019.

(52) U.S. Cl.
CPC ................. *A61B 2034/2055* (2016.02); *A61B 2034/2072* (2016.02); *A61B 2090/3979* (2016.02); *G06T 2207/10048* (2013.01); *G06T 2207/30004* (2013.01); *G06T 2207/30208* (2013.01)

(58) Field of Classification Search
CPC ............ A61B 2090/3979; A61B 34/25; A61B 2034/107; A61B 2034/2051; A61B 2090/3983; A61B 2017/00477; G06T 7/20; G06T 2207/10048; G06T 2207/30004; G06T 2207/30208
See application file for complete search history.

(56) References Cited

U.S. PATENT DOCUMENTS

| | | | |
|---|---|---|---|
| 9,220,573 | B2 | 12/2015 | Kendrick et al. |
| 9,622,824 | B2 | 4/2017 | Goldbach |
| 10,531,926 | B2 | 1/2020 | Roessler |
| 10,765,480 | B2 | 9/2020 | Srimohanarajah et al. |
| 11,653,983 | B2 | 5/2023 | Bonny et al. |
| 2014/0276855 | A1* | 9/2014 | de la Barrera ......... G16H 40/40 705/2 |
| 2015/0045656 | A1 | 2/2015 | Yoon et al. |
| 2016/0262838 | A1* | 9/2016 | Jajal ....................... A61B 34/20 |
| 2017/0319217 | A1 | 11/2017 | Manley et al. |
| 2018/0049622 | A1 | 2/2018 | Ryan et al. |
| 2018/0092699 | A1* | 4/2018 | Finley .................... A61B 34/20 |
| 2018/0250077 | A1 | 9/2018 | Xu et al. |
| 2019/0150901 | A1* | 5/2019 | Ponzer ................... A61B 90/39 |
| 2019/0231408 | A1 | 8/2019 | DiCorleto |
| 2019/0321108 | A1 | 10/2019 | Ghanam et al. |
| 2020/0129238 | A1 | 4/2020 | Bar-Tal et al. |
| 2020/0360092 | A1 | 11/2020 | Deng et al. |
| 2021/0183075 | A1 | 6/2021 | Schipper et al. |
| 2021/0236212 | A1 | 8/2021 | Ghanam et al. |
| 2026/0007476 | A1 | 1/2026 | Coakley et al. |

FOREIGN PATENT DOCUMENTS

| | | | |
|---|---|---|---|
| CN | 110123456 | A | 8/2019 |
| EP | 1700574 | A1 | 9/2006 |
| EP | 1872735 | A1 | 1/2008 |
| EP | 3510927 | A1 | 7/2019 |
| JP | 2002516690 | A | 6/2002 |
| JP | 2019122768 | A | 7/2019 |
| WO | 2011005080 | A1 | 1/2011 |
| WO | 2013115640 | A1 | 8/2013 |
| WO | 2017100180 | A1 | 6/2017 |
| WO | 2018032084 | A1 | 2/2018 |
| WO | 2018203304 | A1 | 11/2018 |
| WO | 2022006248 | A1 | 1/2022 |

OTHER PUBLICATIONS

English language abstract for CN 110123456 A extracted from espacenet.com database on Aug. 30, 2024, 2 pages.
English language abstract for JP 2002-516690 A extracted from espacenet.com database on Aug. 30, 2024, 1 page.
English language abstract for JP 2019-122768 A extracted from espacenet.com database on Aug. 30, 2024, 2 pages.
English language abstract for CN 107405170 A extracted from espacenet.com database on Dec. 9, 2024, 1 page.
English language abstract for EP 1 872 735 A1 extracted from espacenet.com database on Apr. 7, 2021, 2 pages.
International Search Report for Application No. PCT/IB2018/053130 dated Mar. 29, 2021, 3 pages.
OSRAM OPTO Semiconductors GMBH, "SFH 4714 A Olsen Black Specification Sheet", Version 1.2, May 29, 2018, 15 pages.
Partial International Search Report for Application No. PCT/IB2018/053130 dated Jan. 11, 2021, 2 pages.

* cited by examiner

SYSTEMS AND METHODS FOR CALIBRATING A TRACKING ARRAY

RELATED APPLICATIONS

This application is a continuation of U.S. patent application Ser. No. 17/219,067, filed on Mar. 31, 2021, which is a continuation-in-part of International Application No. PCT/IB2020/059064, filed on Sep. 28, 2020, which claims priority to and the benefit of U.S. Provisional Patent Application No. 62/906,629, filed on Sep. 26, 2019, the entire contents of which are hereby incorporated by reference.

BACKGROUND

During surgery, a surgeon often uses instruments that have to be inserted into the body of a patient. Once inside the patient's body, the surgeon loses vision of the tip of the instrument. In order to help the surgeon navigate the instrument in such a case, a surgical navigation system can be used that tracks the instrument and provides visual or acoustic guidance to the surgeon. One way to track the instrument is to attach a tracker onto the instrument. A camera in the operating room detects the tracker and generates data that is used to calculate the position of the tracker and, therefore, of the instrument. Commonly, the patient is also tracked, which enables calculating the position of the instrument relative to the patient. Improvements to trackers are desired.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
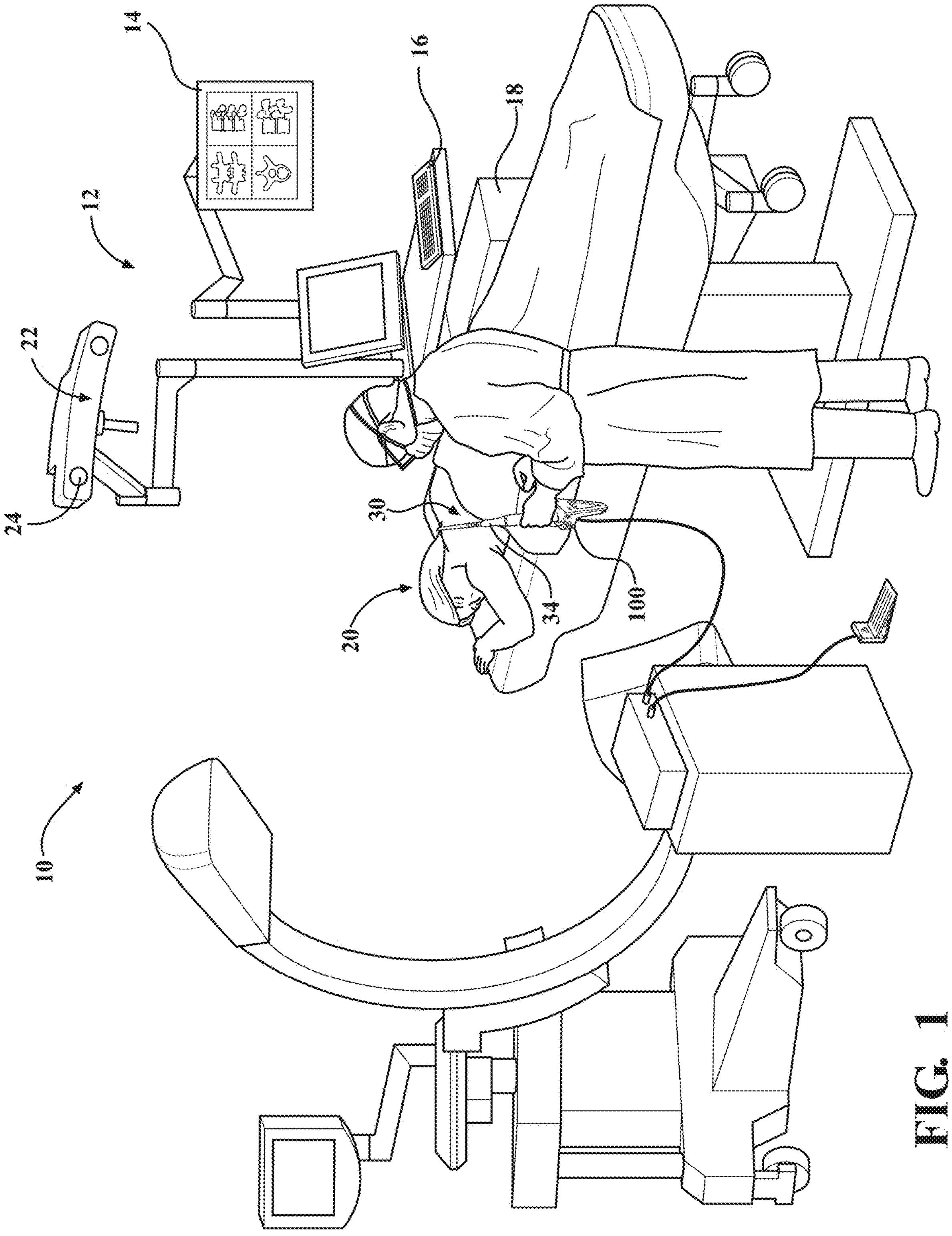
FIG. 1 is an exemplary surgical suite showing a surgical navigation system.

With reference to the Figures, wherein like numerals indicate like parts throughout the several views, the present disclosure includes a tracker 100 for a handheld surgical instrument 34 a surgical navigation system 12 and a method for operating the tracker 100. FIG. 1 illustrates an exemplary surgical system 10 that may comprise the surgical navigation system 12 for tracking one or more surgical instrument assemblies 30 including the surgical instrument 34 and the tracker 100 to assist the medical professional, such as a surgeon, in executing a medical procedure.

The surgical navigation system 12 may comprise a navigation interface that includes one or more display units 14 and one or more user inputs 16. The display unit 14 of the surgical navigation system 12 may be configured to display various prompts or data entry boxes. For example, the display unit 14 may be configured to display a text box or prompt that allows the surgeon to manually enter or select the type of surgical procedure to be performed. The display unit 14 may also be configured to display patient data, such as a pre-operative image or scan. As described above, the pre-operative image may be based on MRI scans, radiological scans, or computed tomography (CT) scans of the patient's anatomy. The preoperative image may be uploaded to the surgical navigation system 12 and displayed on the display unit 14. The display unit 14 may be further configured to display a surgical plan for a medical procedure overlaid on the patient data or image. The surgical plan may include the surgical pathway for executing the medical procedure or planned trajectory or orientation for the medical instrument during the medical procedure. The surgical plan may also include overlaying the position and/or orientation of an implant or medical device to be inserted during the medical procedure on the patient data or image. It is contemplated that the surgical navigation system 12 may comprise a display unit 14 configured to display and/or project a holographic image of surgical pathway for executing the medical procedure or planned trajectory or orientation for the medical instrument during the medical procedure. This may include projecting the surgical pathway onto the patient or other surface in the operating room. It may also include a projection of the surgical pathway onto the head unit worn by the surgeon, such as a lens, shield, or glasses of the head unit. An exemplary configuration of surgical navigation system 12 including a display unit worn by the surgeon to display the target trajectory and/or target location is disclosed in International Patent Application No. PCT/IB2018/053130, the entirety of which is hereby incorporated by reference.

The user input 16 may be configured to allow the surgeon to input or enter patient data or modify the surgical plan. The patient data may comprise patient images, such as preoperative images of the patient's anatomy. These images may be based on MRI scans, radiological scans, or computed tomography (CT) scans of the patient's anatomy. The patient data may also include additional information related to the type of medical procedure being performed, the patient's anatomical features, the patient's specific medical condition, and/or operating settings for the surgical navigation settings. For example, in performing a spinal surgery, the surgeon may enter information via the user input 16 related to the specific vertebra on which the medical procedure is being performed. The surgeon may also input various anatomical dimensions related to the vertebrae and/or the size and shape of a medical device or implant to be inserted during the medical procedure. The user input 16 may also be configured to allow the surgeon to select, edit or manipulate the patient data. For example, the surgeon may identify and/or select anatomical features from the patient data. This may include selecting the surgical site, such as selecting the vertebra and/or specific area on the vertebra where the medical procedure is to be performed.

The surgical navigation system 12 may further comprise a navigation processor 18. The navigation processor 18 can be located on a personal computer or laptop computer. The navigation processor 18 may be in communication with the user input 16, display unit 14, central processing unit (CPU) and/or other processors, memory (not shown), and storage (not shown). The navigation processor 18 may further comprise software and/or operating instructions related to the operation of the surgical navigation system 12 and to implement the various routines and/or methods disclosed herein. The software and/or operating instructions may comprise a planning system configured to find an accurate position and/or angular alignment of the surgical instruments 34 in relation to the patient 20. The navigation processor 18 may be in wired or wireless communication with the surgical instrument assemblies 30, directly or indirectly.

The surgical navigation system 12 may also comprise a tracking unit 22, or localizer, including one or more sensors 24. The sensors may comprise cameras, such as CCD cameras, CMOS cameras, and/or optical image cameras, magnetic sensors, radio frequency sensors, or any other sensor adapted to detect and/or sense the position of a tracking device 100 of the surgical instrument assemblies 30. The localizer 22 is capable of detecting radiation or light from the plurality of markers 128 and of generating a localizer signal representative of the detected radiation or light. An exemplary surgical navigation system 12 may be configured to utilize a tracker 100 with a fixed spatial relation between the markers 128. Description of various suitable localizers that may be utilized can be found in U.S. Pat. No. 10,531,926 B2, which is hereby incorporated by reference in its entirety.

The processor 18 may be capable of receiving the localizer signal. The processor 18 may further be capable of registering and tracking the tracker 100 based on the received sensor signal. Based on the localizer signal, the processor is also capable of calculating an orientation and/or position of the tracker 100 relative to the localizer 22. The processor 18 may have access to information about the spatial relation. In such a case, three-dimensional images captured by a stereo camera would not be required and the camera may only comprise a single two-dimensional image sensor.

The processor 18 may further be configured to receive and/or store information of a patient's body 20 (e.g., a computed tomography scan and/or tracking signal of the patient's body). The processor 18 may then calculate a position and/or orientation of the surgical instrument 34 relative to the patient's body 20. The processor 18 may be configured to generate a visual or acoustic signal indicative of the tracking of the surgical instrument 34. The visual signal may be displayed on the display unit. The processor 18 may be a part of a computing device separate from the localizer. Alternatively, the localizer may comprise the processor.

Figure 2:
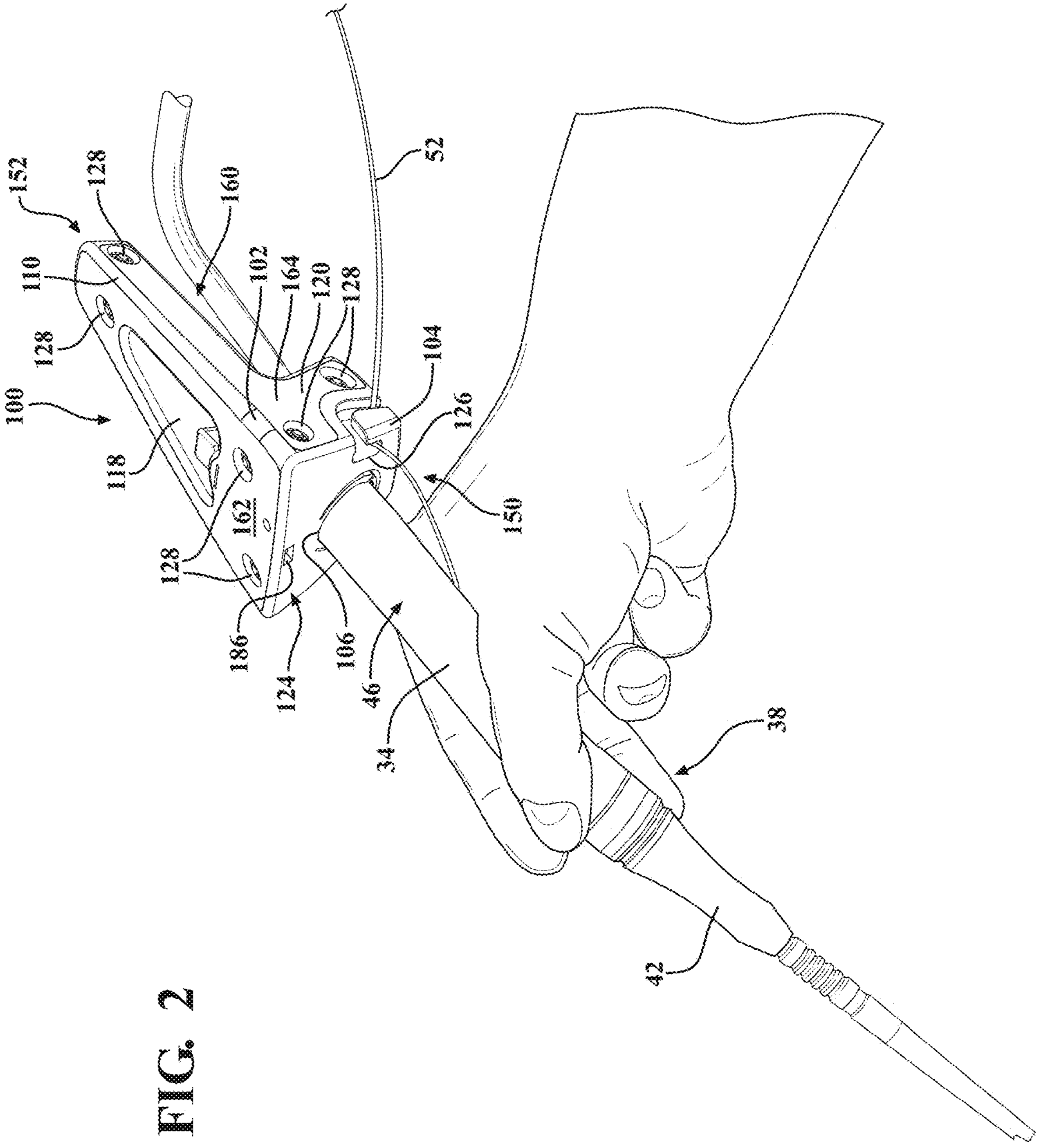
FIG. 2 is an environmental view of a first embodiment of a tracker and a surgical instrument being grasped by a user.

FIG. 2 shows a perspective view of a first configuration of the tracker 100 and the surgical instrument 34. The surgical instrument 34 has a proximal end 36 and a distal end 38 that are spaced along an instrument axis 40. In many cases, such as shown in FIG. 2, the surgical instrument 34 transfers mechanical energy along the instrument axis 40 from a source (e.g. a motor or an ultrasonic transducer) arranged near the proximal end 36 to an attachment 42 coupled to the distal end 38 of the surgical instrument 34. One example of this arrangement is shown in FIGS. 2-7, where the surgical instrument 34 is illustrated as a high-speed drill. Here, the surgical instrument 34 may include a housing 46, a motor (not shown) disposed in the housing 46, a flexible supply cable 48 protruding from the housing 46 in a proximal region, and an attachment interface 50 near the distal end 38 of the surgical instrument 34. Exemplary surgical instruments can be found in U.S. Pat. No. 8,597,316 and U.S. Patent Publication No. 2017/0319217, which are hereby incorporated by reference.

The tracker 100 is operable with the surgical instrument 34 and the surgical navigation system to determine the position and/or orientation of the surgical instrument 34 within an operating room. In order to accurately determine the position of the surgical instrument 34 the tracker 100 is coupled to the surgical instrument 34 and configured to prevent relative movement therebetween during a surgical procedure. Additionally, the tracker 100 should be coupled to the surgical instrument 34 so as to maximize visibility of the tracker 100 by the surgical navigation system.

While the surgical instrument 34 is shown throughout the figures as a high-speed drill, the tracker 100 could be utilized with surgical instruments 34 other than high-speed drills.

For example, the tracker 100 could be coupled to a handheld ultrasonic ablation tool or a biopsy needle or a portion of a robotic device, such as robotic end effector. Similarly, the tracker 100 could be adapted to couple to other surgical instruments (not shown) such as a handheld drill, a saw, or a bur. Again, similarly, the attachment 42 coupled to the distal end 38 of the surgical instrument 34 is shown in FIG. 2 as an angled attachment, which drives a rotary tool on an axis (not shown) different than the instrument axis 40. For example, the attachment could be straight, angled at 15 degrees, 45 degrees, etc.; the attachment could be of various lengths such as 30 mm, 50 mm, etc.

Surgical instruments may have little mass and may be structurally weak. When a heavy tracker is attached to such a handheld surgical instrument 34, the tracker 100 shifts the center of mass, which can be tiresome (e.g., due to a torque applied at the holding hand). Furthermore, the surgical instrument 34 may deform (elastically or plastically) or even be damaged due to the weight of the attached heavy tracker 100. The tracker 100 illustrated throughout the figures typically has a reduced weight. Therefore, the above-mentioned disadvantages are reduced or eliminated. The handheld surgical instrument 34 may be less tiresome to hold by hand and may be less likely to be deformed by the weight of the tracker 100.

In order to facilitate removably coupling the tracker 100 to the surgical instrument 34, the tracker 100 comprises a tracker frame 102 comprising a mounting body 104, which defines an instrument engaging aperture 106 extending therethrough along a longitudinal axis 108. As will be discussed in further detail below, the instrument engaging aperture 106 is configured to receive the surgical instrument 34 such that the instrument axis 40 is aligned with the longitudinal axis 108 of the mounting body 104. In other words, the mounting body 104 may be concentric with the body of the surgical instrument 34. The tracker frame 102 may further comprise an offset body 110 supported on the mounting body 104 and extending proximally and generally parallel to the longitudinal axis 108. The offset body 110 may define a cutout 118 extending therethrough in a direction generally perpendicular to the longitudinal axis 108. The tracker frame 102 may comprise a metal, such as titanium, a polymer such as nylon, or an epoxy resin, such as aromatic epoxy amine resin. The tracker frame may comprise any other suitable material for use in a medical setting, providing the necessary rigid structure to the tracker 100. The tracker frame may consist of polymer and may be manufactured using additive manufacturing techniques.

Alternatively, the tracker 100 and surgical instrument 34 may be mechanically connected for a one-time use. The tracker 100 and the surgical instrument 34 may be integrally formed (e.g., during injection molding). The tracker 100 may, for example, be integrally formed with a handle of the surgical instrument 34. With the tracker 100 already attached to the instrument 34, the surgeon can immediately use the surgical instrument 34 without having to attach the tracker 100 thereon. The surgeon may dispose of both the tracker 100 and the surgical instrument 34 after the one-time use.

In order to track the position and orientation of the surgical instrument 34, the tracker 100 comprises a plurality of markers 128 optionally arranged in one or more arrays 162, 164, 166 and coupled to the tracker frame 102. The tracker frame 102 may have three sides that are each aligned with the respective radial segments 112, 114, 116, each side oriented approximately 120 degrees from the others. The plurality of arrays 162, 164, 166 are positioned such that each array 162, 164, 166 is arranged on one of the three sides and oriented in a different direction from each other. The first array 162 is arranged on the side aligned with the first radial segment 112, the second array 164 is arranged on the side aligned with the second radial segment 114, and the third array 166 is arranged on the side aligned with the third radial segment 116. The side aligned with the first radial segment 112 is positioned on the offset body 110. The offset body 110 and the mounting body 104 cooperate to define the two sides that align with the second and third radial segments 114, 116. Other number of arrays and/or number of sides are also contemplated.

While each side has a specific radial arrangement, the angle of the sides may be configured such that they are angled toward a common vertex, such that they would converge at a point beyond a proximal end 152 of the offset body 110. The offset body 110 and/or the first array 162 may define a skew axis, such that the offset body 110 protrudes from the mounting body 104 along the skew axis. The skew axis may further define three skew segments (similar to the radial segments discussed herein) of equal proportion about the skew axis. Here, the at least six markers 128 are radially arranged about the longitudinal axis, and at least three markers 128 are radially arranged about the skew axis and arranged on the offset body 110 such that one of these at least three markers 128 is in each of the three skew segments and spaced from the longitudinal axis 108 to provide clearance for the flexible supply cable 48.

One method for increasing the accuracy of the surgical navigation system includes maximizing the visibility of the tracker 100. Increasing the accuracy of the tracker 100 can be increased in several ways, for example, the size of the tracker 100 can be increased, the quantity of markers 128 can be increased, the brightness of the markers 128 can be increased, and more. However, these methods may result in increasing the size and/or the mass of the tracker 100, for example, increasing the brightness of the markers 128 would be at the expense of power consumption, thereby reducing a duration that the tracker 100 can be operated, or a heavier battery with an increased capacity.

Figure 3:
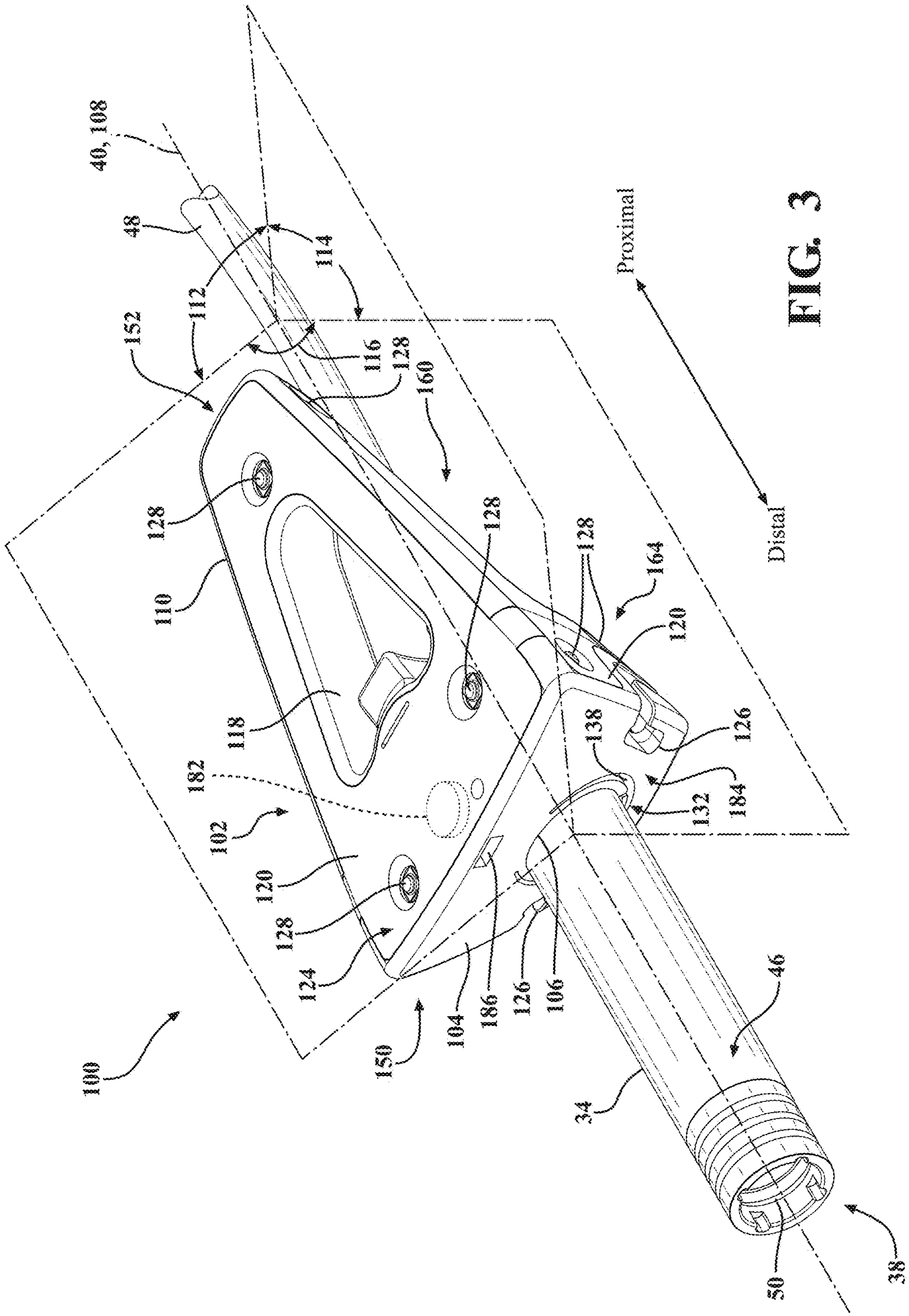
FIG. 3 is a perspective view of the tracker of FIG. 2, the tracker having a tracker frame coupled to a surgical instrument and with three radial segments arranged about a longitudinal axis of the tracker.
Figure 4:
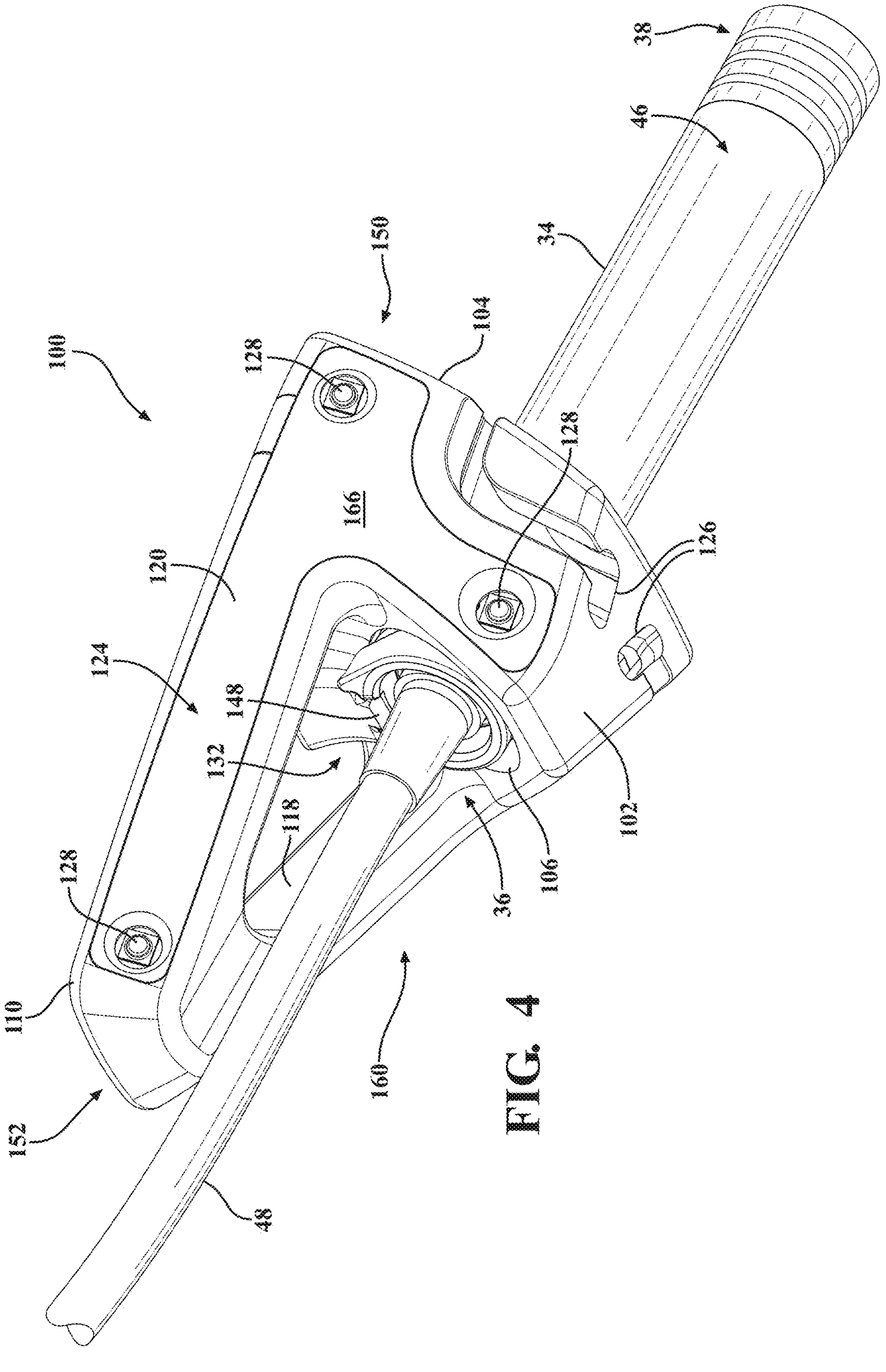
FIG. 4 is another perspective view of the tracker of FIG. 2, wherein the tracker frame is shown coupled to the surgical instrument.

The visibility of the tracker 100 can also be increased by strategic arrangement of the markers 128 on the tracker frame 102. Best shown in FIGS. 3 and 7, three radial segments 112, 114, 116 are defined about the longitudinal axis 108. Each radial segment 112, 114, 116 has a volume that corresponds to a respective portion of the tracker 100 and the arrangement of components of the tracker 100. As shown, the first radial segment 112 may be generally defined in alignment with the offset body 110. The second and third radial segments 114, 116 are aligned across the longitudinal axis 108 opposite to the offset body 110. For example, as illustrated in FIG. 3, each radial segment 112, 114, 116 extends 120 degrees about the periphery of the tracker 100. The radial segments 112, 114, 116 are defined such that all three are equal in size.

In some configurations the tracker 100 may comprise a body shell 120, such as the first configuration shown in FIGS. 2-11, and the second configuration shown in FIGS. 12-16. The body shell 120 covers portions of the tracker frame 102 and encloses an interior 122 of the tracker frame 102 and an exterior 124 (see FIG. 11). As will be discussed in further detail below, certain components of the tracker 100 may be arranged within the interior 122 of the tracker frame 102. The body shell 120 may be constructed from a polymer material, titanium, or other suitable materials. The tracker frame 102 may be of unitary or monolithic construction such that there is no discrete mounting body 104 and/or offset body 110. Suitable manufacturing processes for forming the tracker frame 102 and body shell 120 may include injection molding, additive manufacturing (3D printing), computer numerical control (CNC) machining, polymer casting, vacuum forming, and blow molding, among others.

A tube guide 126 may be defined on the tracker frame 102 in the mounting body 104 and configured to receive a surgical irrigation tube 52. The tube guide 126 receives the irrigation tube 52 and neatly routes the irrigation tube 52 around the tracker frame 102 and out of the way of the surgeon such that the irrigation tube does not interfere with the tracker frame in an unpredictable way. The tracker 100 may comprise two tube guides 126, which may be configured to receive irrigation tubes 52 with different diameters. These tube guides 126 may be equal in size or be differently sized to accommodate multiple sizes of irrigation tube 52. As illustrated in FIG. 2, the tube guides 126 are configured to direct the irrigation tubes 52 through an approximately 90-degree bend so as to be generally parallel with the longitudinal axis 108 as it meets the surgical instrument 34. The tube guide may also be configured to be a guide for other elongate members, such as wires to power trackers and aspiration tubes.

Figure 8:
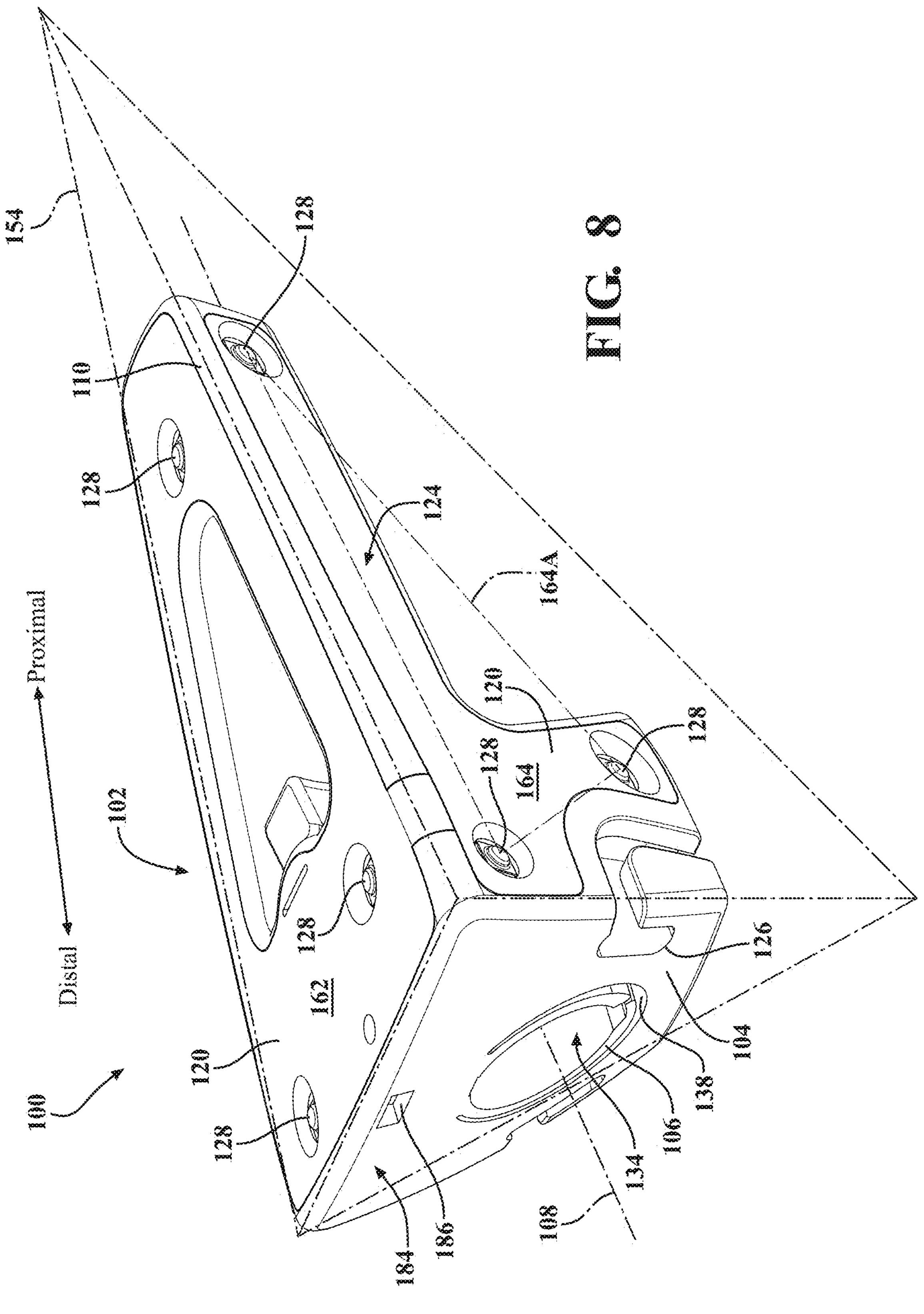
FIG. 8 is a perspective view of the tracker of FIG. 2 showing the tetrahedral shape of the tracker frame and a marker array and area.

When viewed in perspective, such as in FIG. 8 the tracker frame 102 may have a generally tetrahedral-like shape due to the arrangement of the three sides in alignment with the radial segments 112, 114, 116. These sides each form one of four faces of a tetrahedron 154, and edges are defined at intersections of each side. The fourth face of the tetrahedron is formed by a distally directed face 184 on the mounting body 104. This distally directed face 184 is generally perpendicular to the longitudinal axis 108 and defines a portion of the instrument engaging aperture 106. The distally directed face 184 is arranged opposite a proximally directed face 184 of the mounting body 104. The distally directed face 184 and the proximally directed face 185 generally form respective distal and proximal ends of the mounting body 104. The tetrahedral-like shape may be implemented as a regular tetrahedron, having all four faces that are the same, or an irregular tetrahedron, where some of the faces are differently sized and meet at different angles.

In some embodiments the tracker 100 may comprise as few as four markers 128 to track the surgical instrument 34. In these embodiments each of the markers 128 is coupled to the tracker frame 102 and arranged at a vertex of the tetrahedral shape. Each marker 128 forms an array with two other markers 128 that are visible to the navigation system. Each marker 128 may be oriented differently than the others to maximize the radial emission of light about the longitudinal axis 108.

As mentioned above, the offset body 110 is supported on the mounting body 104 and extends in a proximal direction. The offset body 110 extends from a distal end 150 coupled to the mounting body 104, and adjacent to the distally directed face 184, to a proximal end 152. A length 156 of the offset body 110 is defined between the distal end 150 and the proximal end 152, which corresponds to a distance that the proximal end 152 is spaced from the mounting body 104. The proximal end 152 is adjacent to one vertex of the tetrahedron 154 defined by the tracker frame 102. Best shown in FIGS. 6, 8, and 10, the offset body 110 is tapered from the distal end 150 to the proximal end 152, in other words, the proximal end 152 has a smaller profile than the distal end 150.

Figure 5:
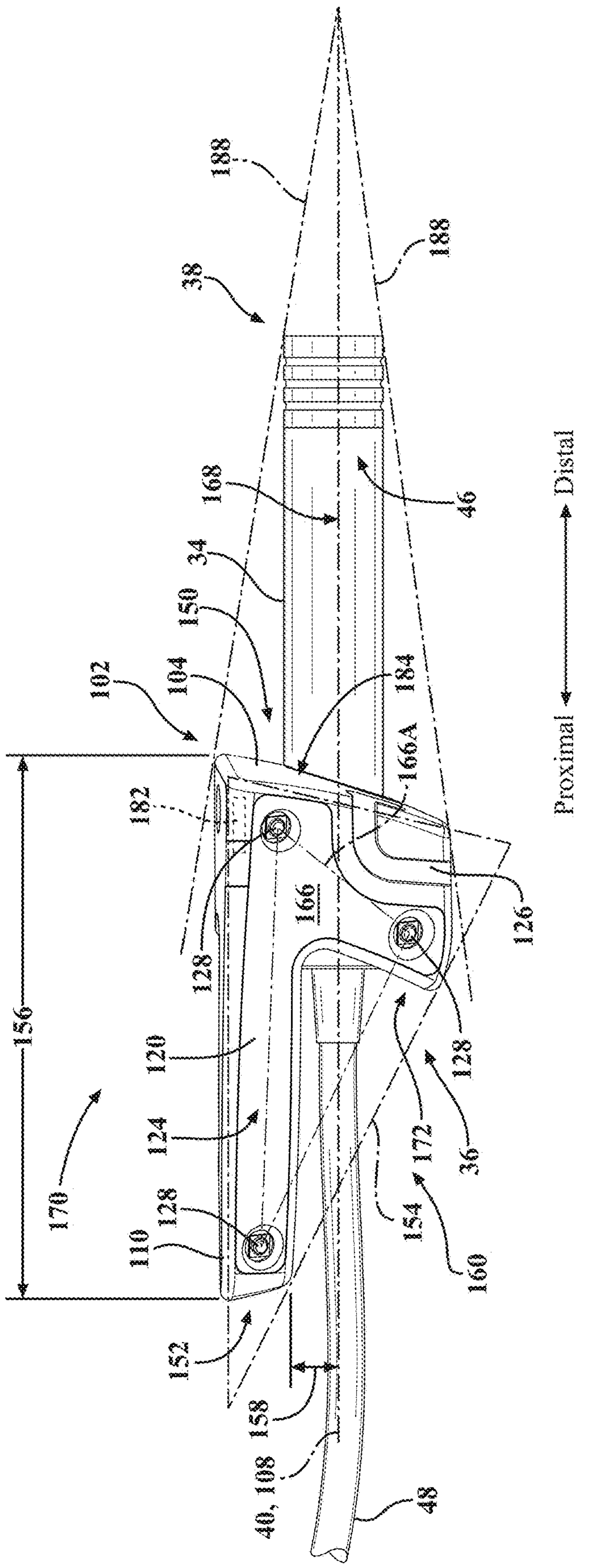
FIG. 5 is a side view of the tracker of FIG. 2 showing a tetrahedral shape of the tracker frame and two sightlines between the tracker and the surgical instrument.

Also as noted above, the offset body 110 is generally arranged in the first radial segment 112 and, further, is spaced from the longitudinal axis 108 at a height 158, as best shown in FIG. 5. Due in part to the smaller profile of the proximal end 152 and to the height 158 at which the proximal end 152 is spaced, the tracker frame 102 provides a relief area 160 for the flexible supply cable 48 of the surgical instrument 34. Best shown in the side view of FIG. 5, the relief area 160 is generally centered around the flexible supply cable 48 and minimizes potential contact between the flexible supply cable 48 and the tracker frame 102. For example, when a user such as the surgeon utilizes a pencil grip with the surgical instrument 34 in a way similar to that shown in FIG. 2, the flexible supply cable 48 will generally curve towards the floor and away from the surgeon. Because the flexible supply cable 48 has mass, it exerts a force on the proximal end 36 of the surgical instrument 34, which becomes a moment centered about the location where the surgeon is gripping the surgical instrument 34. As the surgical instrument 34 moves during the course of a surgical procedure, the surgeon often becomes familiar with the forces associated with the flexible supply cable 48 naturally following this movement. If the flexible supply cable 48 comes into contact with something unexpectedly, the balance of the surgical instrument 34 is affected. When the instrument's 34 balance is inconsistent, the delicate movements of the surgeon may be impacted, which may cause undesired movement at the distal end 38 of the surgical instrument 34. By providing a large relief area 160 below the offset body 110, the surgeon is able to move the surgical instrument 34 confidently and with an increased range of motion while reducing the chance that the flexible supply cable 48 will contact the tracker frame 102. The relief area 160 provides clearance for the flexibly supply cable 48 to curve freely at a small bend radius (i.e. at a large angle to the instrument axis 40) without contacting the tracker frame 102.

In addition to reducing the mass of the tracker 100 it is desirable to reduce any interference with the surgeon's visibility of a surgical site. In some cases the surgeon may desire to view the surgical site along a sightline 188, shown schematically in FIG. 5, that is generally aligned with the instrument axis 40. If a large tracker is used with the surgical instrument 34, it may obstruct the surgeon's view or require the surgeon to grip the surgical instrument 34 in a less preferred manner, thereby increasing an angle from the longitudinal axis at which the surgeon views the surgical site. The angle of the sightline 188 is influenced both by the length of the surgical instrument 34 as well as the height 158 of the offset body 110 from the longitudinal axis 108. It is therefore desirable to reduce the height 158 of the offset body 110 to minimize the angle of the sightlines 188. However, because the distance that proximal end 152 of the offset body 110 extends proximally from the distal end 150 of the offset body 110 (i.e. the length 156) is greater than the distance that the offset body 110 is spaced from the longitudinal axis 108 (i.e. the height 158), an area of each array 162, 164, 166 is still maximized, thereby maximizing the precision of the tracker 100. The reduced height 158 of the offset body 110 allows the angle of the sightline 188 to be less than 40 degrees. Depending on the attachment 42 coupled to the surgical instrument 34, the sight line could be further reduced to less than 30 degrees, or further still to less than 20 degrees. In certain configurations, no part of the tracker 100 extends from the longitudinal axis by a distance greater than 1, 2, 3, or 4 cm.

As mentioned above, the tracker 100 is coupled to the surgical instrument 34 via the instrument engaging aperture 106 such that the instrument axis 40 and the longitudinal axis 108 are aligned. As accurately determining the position of the surgical instrument 34 is facilitated by a determinate relationship between the tracker 100 and the surgical instrument 34, their coupling should be secure while being removable. Shown in FIGS. 4 and 9, the tracker 100 may further comprise a retention assembly 132 that is configured to secure the surgical instrument 34 within the instrument engaging aperture 106. The retention assembly 132 may be realized in several different ways depending on the specific surgical instrument 34 that is to be tracked, as well as the construction of the tracker frame 102. Specifically, some retention assemblies 132 may be more suited to tracker frames 102 comprising a metal construction and others may be more suited for polymer construction. Suitability may be determined, in part, by the physical characteristics of the surgical instrument 34 such as a weight or a diameter, or by cost such as whether the tracker 100 is to be a single use disposable or durable, as the case may be. In some cases the tracker 100 may comprise more than one retention assembly 132 in order to increase compatibility across a wide variety of surgical instruments 34.

A housing 46 of the surgical instrument 34 is slidably engaged with the tracker frame 102 to securely couple the tracker 100 and the surgical instrument 34. More specifically, by aligning the instrument axis 40 and the longitudinal axis 108 and inserting the distal end 38 of the surgical instrument 34 through a proximal side of the instrument engaging aperture 106.

Figure 10:
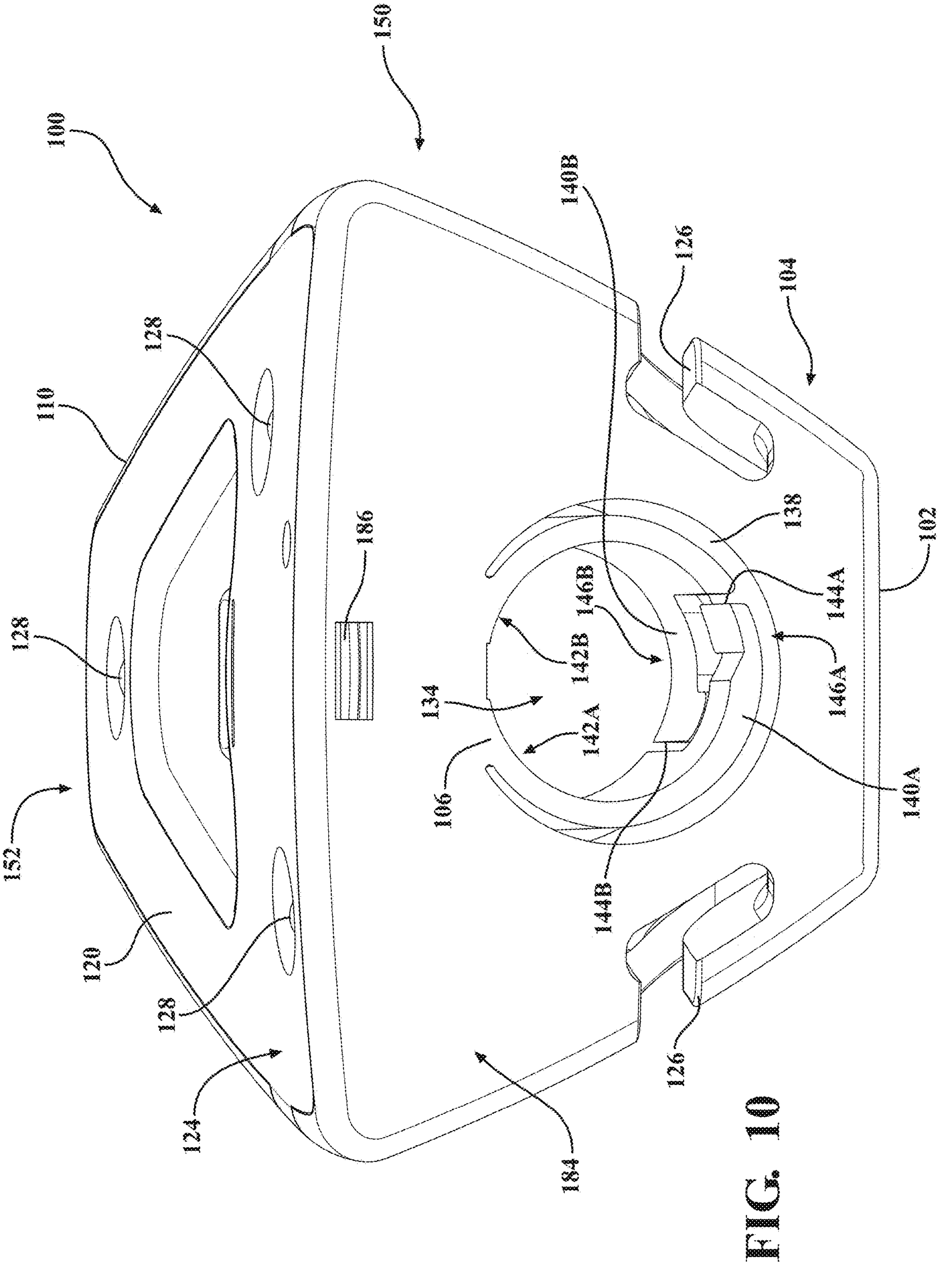
FIG. 10 is a distal perspective view of the tracker of FIG. 2 showing the instrument engaging aperture and a retention assembly.

A first alternative of the retention assembly 132 is realized as a friction clamp 134 shown best in FIGS. 8 and 10. Here, a clamp channel 138 is defined in the mounting body 104 extending therethrough. Two resilient arms 140A, 140B are disposed in the clamp channel 138, each resilient arm 140A, 140B has a reference end 142A, 142B and a movable end 144A, 144B. The reference ends 142A, 142B are both coupled to the mounting body 104 on one side of the clamp channel 138 and extend into the clamp channel 138 to the respective movable ends 144A, 144B. Best shown in FIG. 10, the instrument engaging aperture 106 is positioned so as to align with the resilient arms 140A, 140B, thereby permitting the resilient arms 140A, 140B to contact opposing sides of the housing 46 of the surgical instrument 34 during use. Near each of the movable ends 144A, 144B each resilient arm 140A, 140B has an overlapping portion 146A, 146B having a reduced width. The overlapping portion 146A of a distal resilient arm 140A has a reduced width in the distal direction, and the overlapping portion 146B of a proximal resilient arm 140B has a reduced width in the proximal direction. The reduced width of the overlapping portions 146A, 146B allows each resilient arm 140A, 140B to wrap around the housing 46 of the surgical instrument 34 greater than if the movable ends 144A, 144B were abutting, which here is greater than 180 degrees.

Here, in order to securely couple the surgical instrument 34 and the tracker 100, a diameter of the instrument engaging aperture 106 is smaller than a diameter of the housing 46. When the housing 46 is slidably engaged with the mounting body 104 the movable ends 144A, 144B of the resilient arms 140A, 140B spread apart to increase the diameter of the instrument engaging aperture 106 to match the housing 46. Force from deformation causes the resilient arms 140A, 140B to apply a clamping force on the housing 46. Due to friction and contact between the resilient arms 140A, 140B and the housing 46, the tracker 100 is thereby securely held to the surgical instrument 34.

Figure 9:
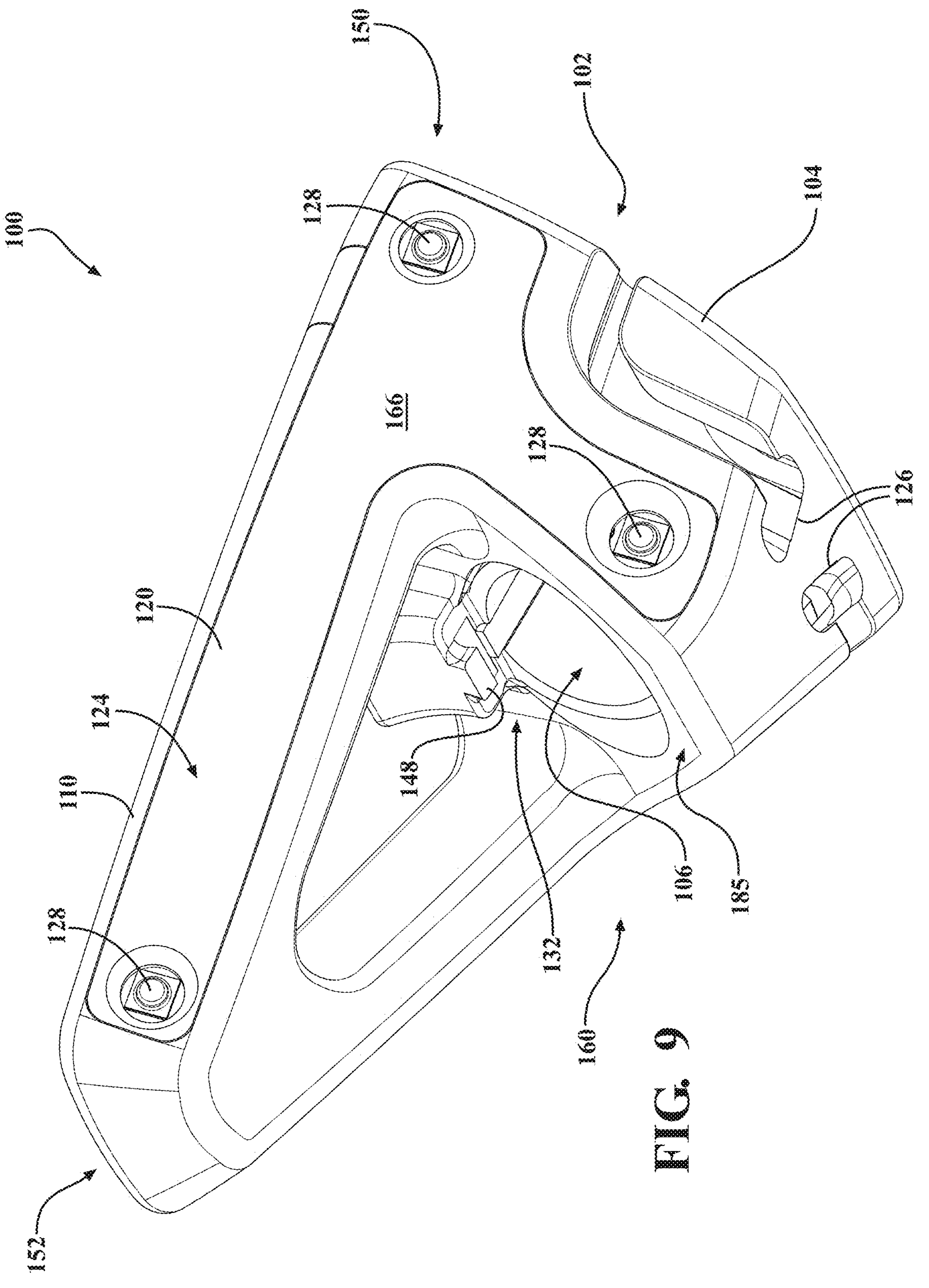
FIG. 9 is a perspective view of the tracker of FIG. 2 showing an instrument engaging aperture and a relief area.

In addition to the resilient arms 140A, 140B, the retention assembly may further comprise an attachment protrusion 148, which is shown arranged on the proximal side of the instrument engaging aperture 106, best illustrated in FIG. 9. The exemplary attachment protrusion 148 is radially arranged about the longitudinal axis 108 and configured for indexing engagement with the surgical instrument 34 along the instrument axis 40. Specifically, the attachment protrusion 148 engages with a complementary shaped recess in the housing 46 of the surgical instrument 34 to index the tracker frame 102 into rotational alignment about the instrument axis 40. Here, the attachment protrusion 148 has a generally rectangular profile that is adjacent to the instrument engaging aperture 106 and positioned asymmetrically such that full engagement of the surgical instrument 34 and the tracker 100 can only be achieved in a single position. Indexing engagement of the surgical instrument 34 and the tracker 100 can be effected through the use of one or more attachment protrusions 148, which may provide redundancy or further retention for securely coupling the tracker 100.

A second alternative of the retention assembly 132 is realized as a cam lock 136', 136" shown in FIGS. 12-16 and 17-21.

Figure 7:
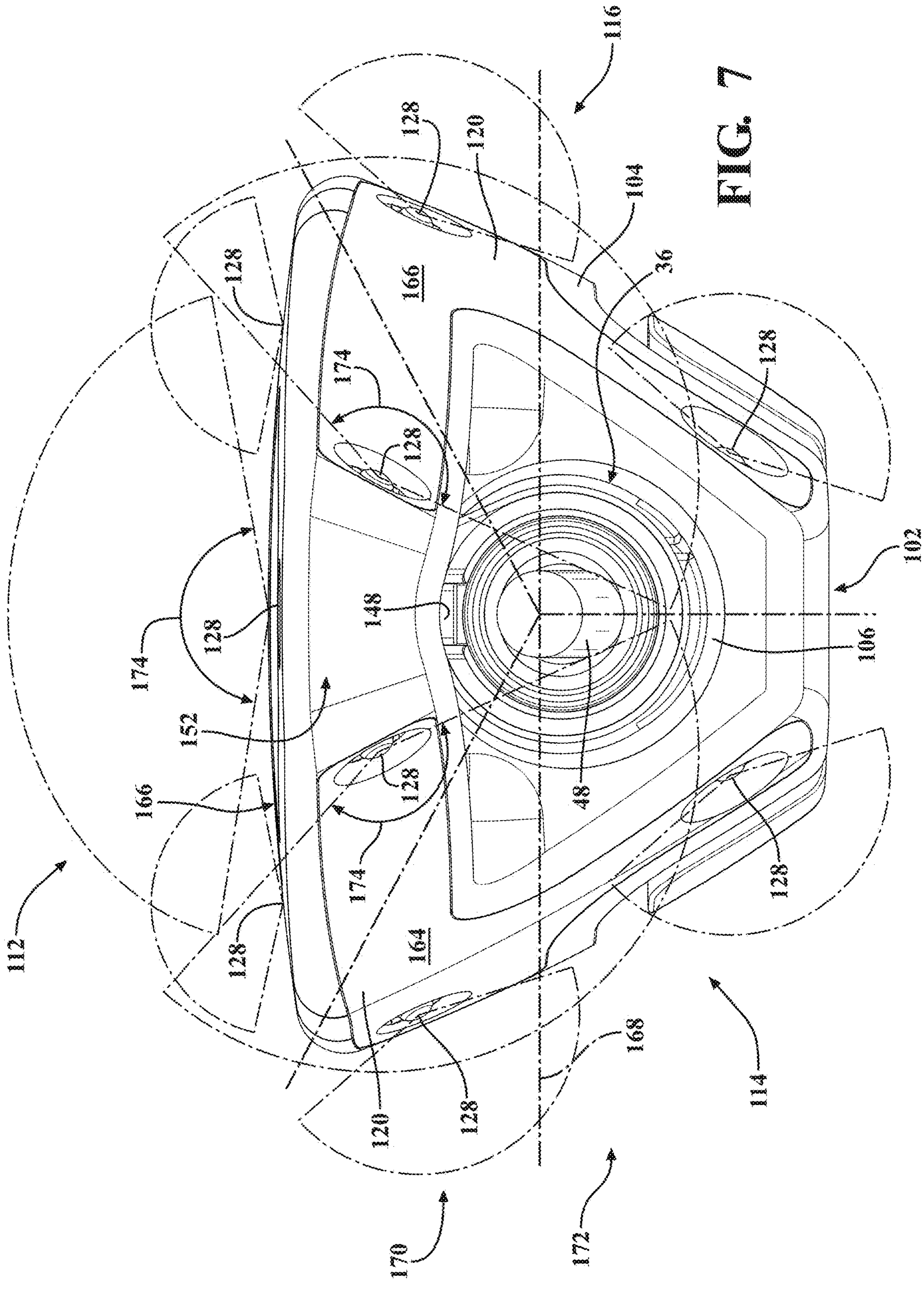
FIG. 7 is a proximal view of the tracker and surgical instrument of FIG. 2 showing three radial segments, a first and second region, and emission patterns for several markers.
Figure 11:
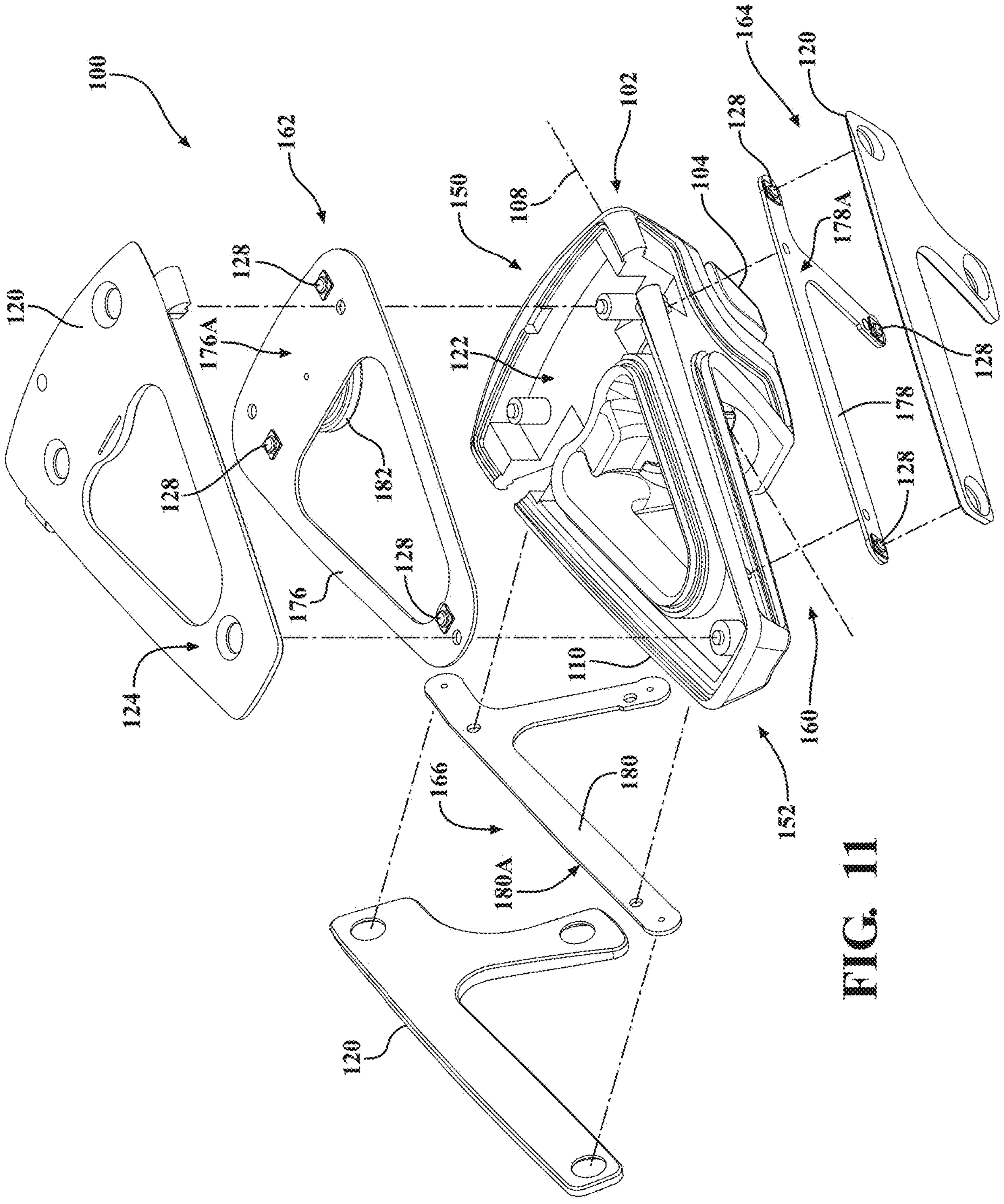
FIG. 11 is an exploded view of the tracker of FIG. 2 showing an interior of the tracker frame and the marker arrays.
Figure 12:
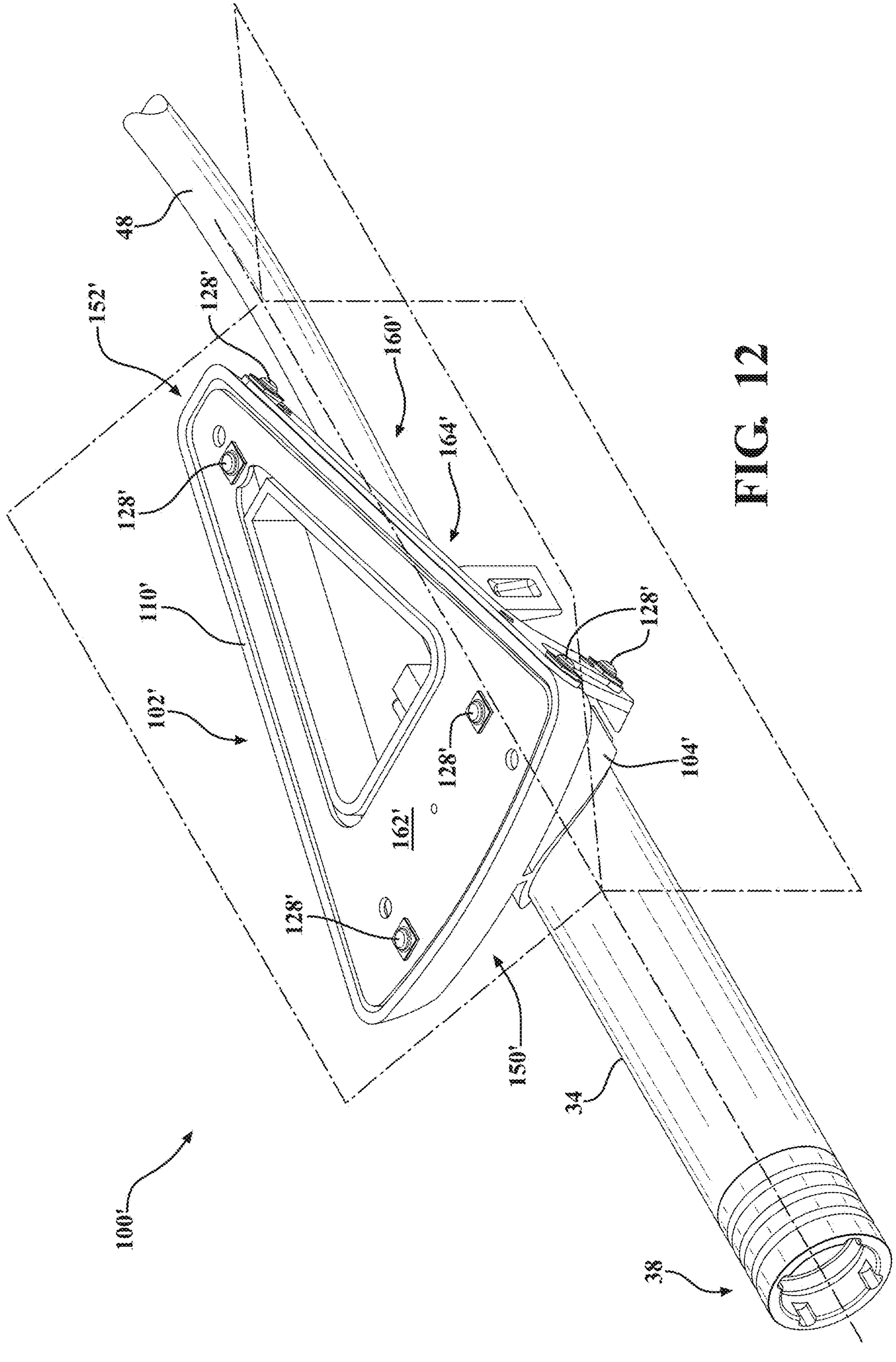
FIG. 12 is a perspective view of another embodiment of a tracker shown coupled to a surgical instrument.
Figure 13:
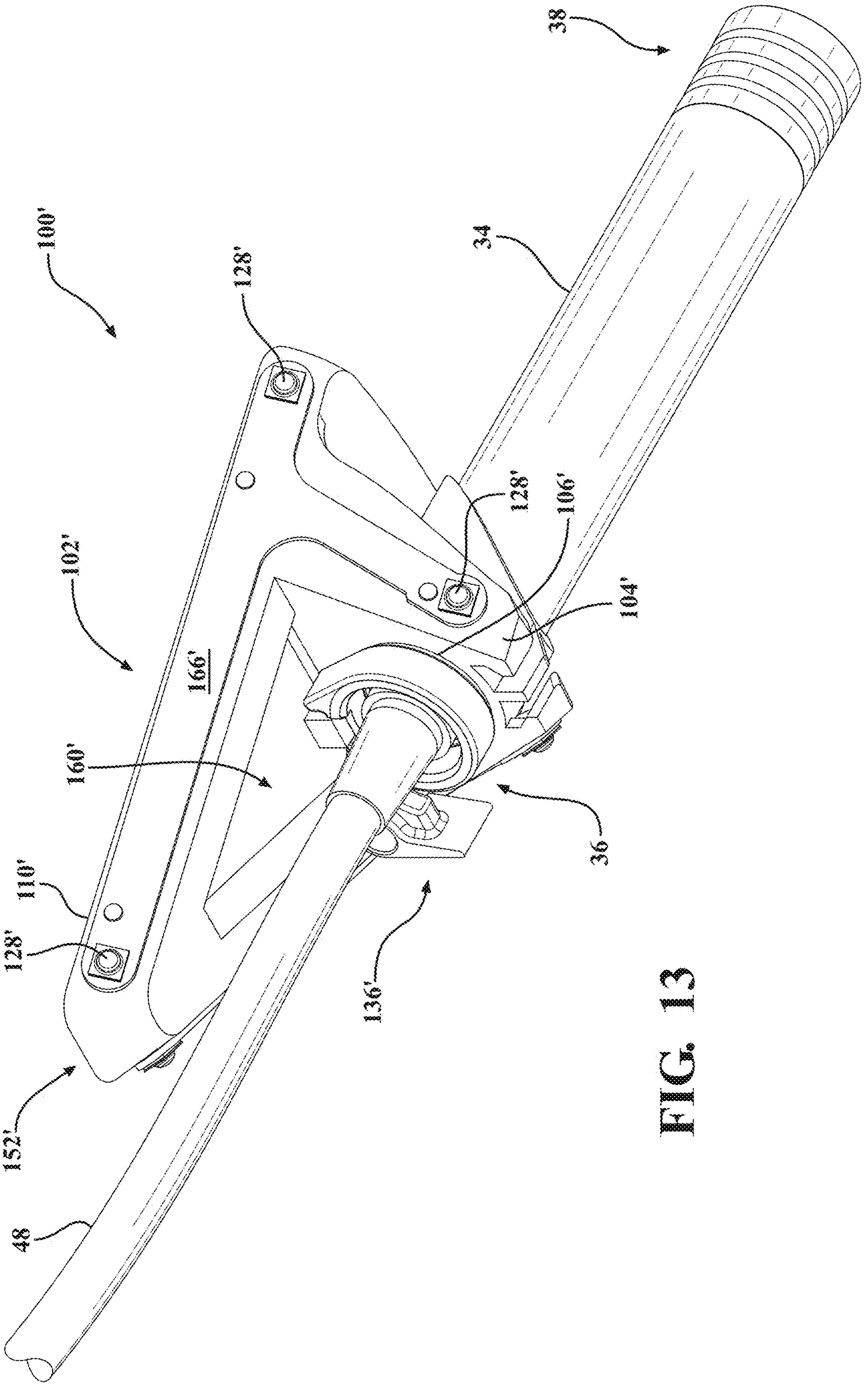
FIG. 13 is another perspective view of the tracker of FIG. 12.
Figure 14:
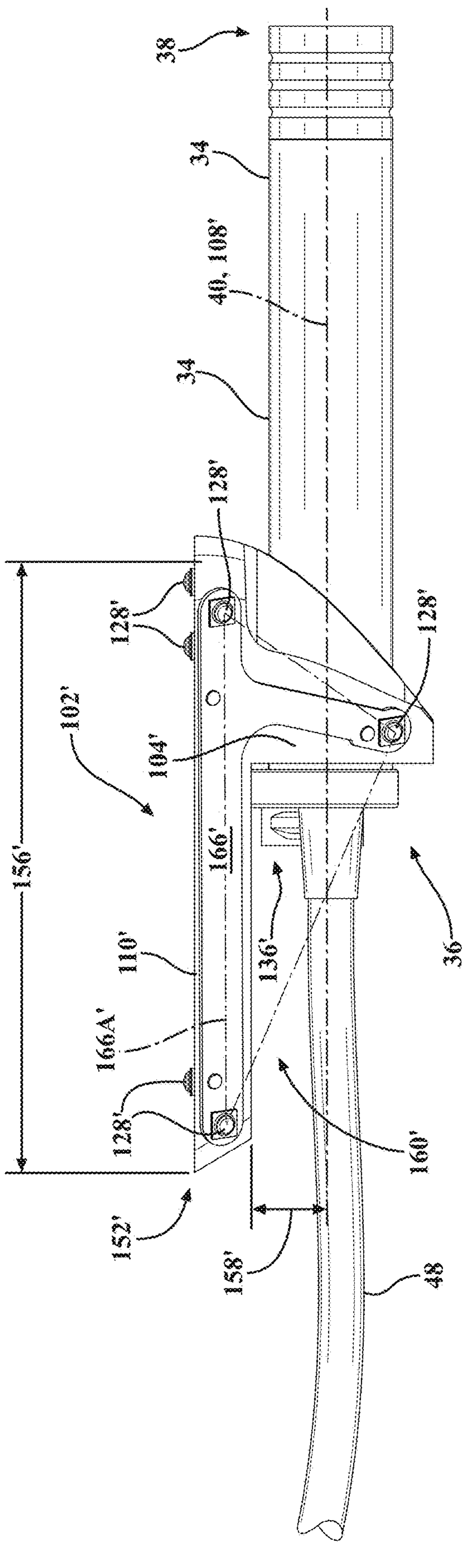
FIG. 14 is a side view of the tracker of FIG. 12.
Figure 15:
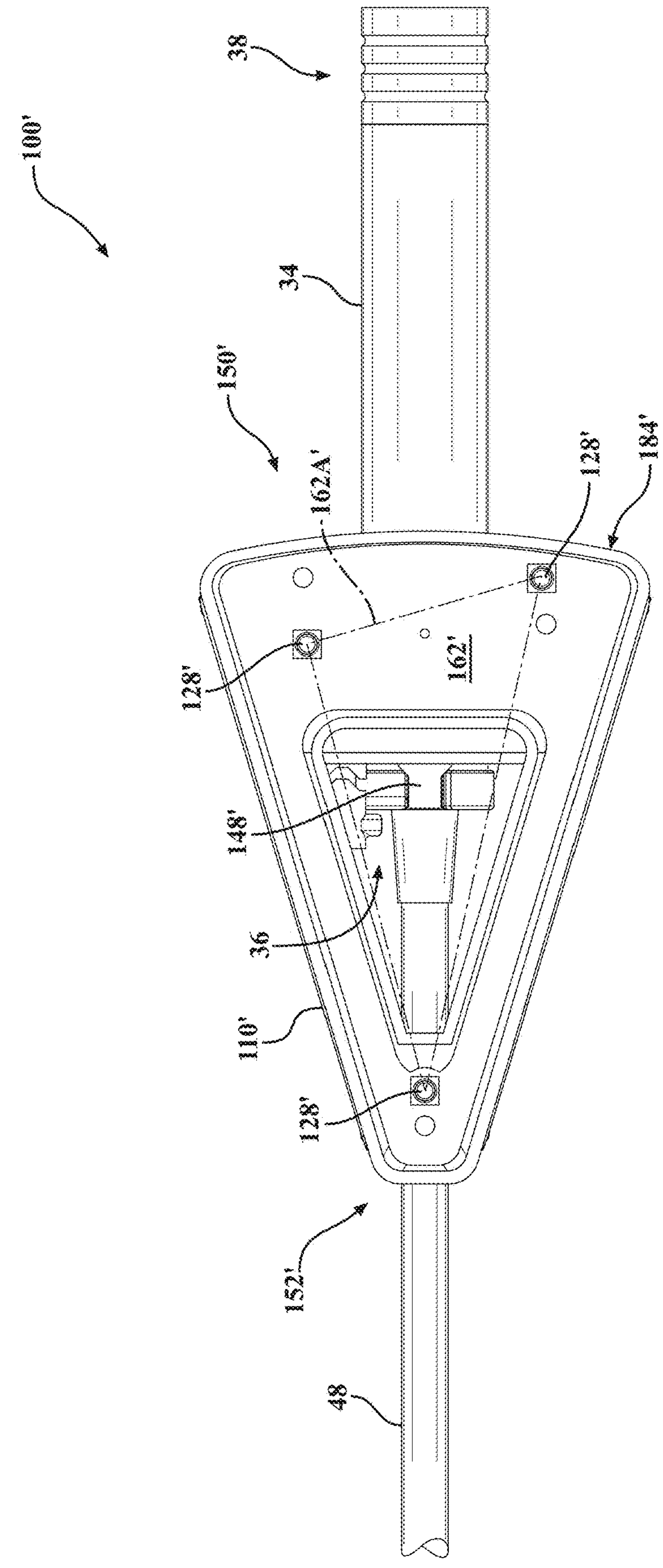
FIG. 15 is a top view of the tracker of FIG. 12.

As mentioned above, the tracker 100 may comprise a plurality of markers 128 arranged into a plurality of arrays 162, 164, 166 coupled to the tracker frame 102. FIGS. 3, 7, and 11 show that the tracker 100 may be configured such that the plurality of markers 128 is further defined as at least six markers 128, where FIG. 7 shows that at least one of the at least six markers 128 is positioned on the tracker frame 102 in each radial segment 112, 114, 116. Said differently, each radial segment 112, 114, 116 contains one of the markers 128, where some of the radial segments 112, 114, 116 may have more than one marker 128.

While the tracker 100 described above comprises at least six markers 128, a greater number of markers 128 may be desirable. For example, the tracker 100 may comprise nine markers 128 for greater three-dimensional accuracy. It is possible to reduce the power consumption of the tracker 100 by reducing the number of markers 128, which may be desirable in a tracker 100 for tracking movement with limited degrees of freedom (such as five degrees of freedom) or, for example, the surgical instrument 34. The tracker 100 may comprise more than nine markers 128 for increased redundancy. Alternatively, the tracker may include exactly nine, ten, eleven, or twelve markers to minimize energy consumption, maximize line of sight, and maintain tracking accuracy. Alternatively still, the tracker may include fewer than twelve markers.

In addition, or the alternative, to the aforementioned arrangement of the markers 128 in each of the radial segments 112, 114, 116, the tracker 100 could be configured such that the plurality of markers 128 are coupled to the tracker frame 102 and asymmetrically radially arranged about the longitudinal axis 108. FIGS. 5 and 7 show an edge of a longitudinal plane 168, which is parallel to the longitudinal axis 108 and bisects the instrument engaging aperture 106 to define a first region 170 and a second region 172. The arrangement of the markers 128 is further defined with respect to the first region 170 and the second region 172. A first quantity of the plurality of markers 128 are positioned in the first region 170, and a second quantity of the plurality of markers 128 are positioned in the second region 172, the first quantity being greater than the second quantity. For example, one configuration of the tracker 100 may comprise nine markers 128, the first quantity of seven markers 128 may be positioned on the tracker frame 102 such that they are in the first region 170, or above the longitudinal plane 168, and the second quantity of two markers 128 may be positioned on the tracker frame 102 such that they are in the second region 172, or below the longitudinal plane 168.

According to this example, there may be more or fewer markers 128 in either region 170, 172 such that the first quantity of markers 128 in the first region 170 is greater than the second quantity of markers 128 in the second region 172.

The tracker 100 may be adapted for compatibility with various different surgical navigation systems and position tracking technologies. For example, the tracker 100 may employ passive tracking markers, which reflect infrared light or radiation that has been emitted from a camera unit or another light source. Although one embodiment of the navigation system is described herein, the navigation system may have any other suitable configuration for monitoring trackers 100, which may be of various types and configurations. For example, the navigation system may comprise other types of cameras and/or markers 28.

In some embodiments, the navigation system may be radio frequency (RF) based. For example, the trackers 100 may comprise RF emitters or transponders, which may be passive or may be actively energized. Alternatively, in some embodiments, the navigation system may be electromagnetically (EM) based. For example, the navigation system may comprise an EM transceiver coupled to a computing device, controller, and the like. Here, the trackers 100 may comprise EM components attached thereto (e.g., various types of magnetic trackers, electromagnetic trackers, inductive trackers, and the like), which may be passive or may be actively energized.

As shown throughout the figures, and with renewed reference to FIG. 7 in particular, the markers 128 are infrared emitters capable of emitting infrared radiation or light which can be sensed by a surgical navigation system. Infrared wavelengths are preferable because ambient lighting used by the surgeon emits in the visible light spectrum, but the wavelength of infrared light is such that the brightness of the marker 128 able to be detected by the surgical navigation system is essentially independent from the brightness of the ambient lighting. Therefore, due to the marker 128 emitting infrared light, the marker 128 may be operated with a lower brightness, which decreases the current required to power the markers 128. The current required to power the markers may be as low as 15 mA, or lower.

Here, the infrared emitters are infrared light emitting diodes (IR-LEDs), which can emit infrared radiation and light at a relatively low power level. The current for at least one of the IR-LEDs may be limited by an internal electrical resistance of the IR-LEDs and an electrical resistance of at least one resistor electrically connected in series to the at least one IR-LED. The current for the at least one IR-LED may be limited by one or more resistor electrically connected in series to the at least one IR-LED.

The tracker 100 comprises an electrical circuit, discussed in further below, disposed in the tracker frame 102. The electrical circuit comprises the IR-LEDs (shown as the markers 128), a battery 182 and a resistor (not shown). The electrical circuit comprises electrical wiring (not shown) that electrically connects the battery 182 to each of the IR-LEDs. The IR-LED, the battery 182 and the resistor are electrically connected in series. Therefore, an electrical resistance of the resistor limits the current for the IR-LED. The resistor has an electrical resistance so that the current for the IR-LED does not exceed approximately 15 mA. In one embodiment, the IR-LEDs are electrically connected in parallel with each other. Therefore, if one of the IR-LEDs fails, the electrical connection of the battery 182 with the remaining IR-LEDs is not interrupted. Each resistor forms a series circuit with its corresponding IR-LED. Furthermore, each IR-LED contributes its own electrical resistance to the electrical resistance of the resulting series circuit. According to Ohm's law the current is inversely proportional to the resistance. Therefore, by adjusting the resistance of each resistor a current through that resistor as well as through its corresponding IR-LED can be adjusted. Exemplary circuit configurations can be found in U.S. Patent Publication No. 2019/0321108, which is hereby incorporated by reference.

In one configuration the tracker 100 comprises four resistors, equal to the number of IR-LEDs. The tracker 100 may alternatively comprise a different number of resistors. Each resistor is disposed between the battery 182 and its corresponding IR-LED. The resistors are disposed inside the tracker frame 102 and each resistor is electrically connected in series to its corresponding IR-LED. The resistors are electrically connected between the IR-LEDs and a positive terminal of the battery 182. Alternatively, at least one resistor may be electrically connected between the corresponding IR-LEDs and a negative terminal of the battery 182. This embodiment comprises a lower amount of resistors and, therefore, has lower material costs. Alternatively, more than one resistor may each be electrically connected in series to a plurality of the IR-LEDs. For example, two resistors may each be electrically connected in series to the IR-LEDs.

The electrical circuit further may further comprise a switch 186 that is operable by the user and configured to electrically open and close the electrical circuit. Therefore, the IR-LED may be operated by operating the switch 186, which opens and closes the electrical circuit that connects the battery 182 with the IR-LED. Alternatively, a plurality of switches may be provided configured to individually control power supply to each IR-LED. As a further alternative, the tracker 100 may comprise at least one one-time or single-use switch. Such a one-time use may be realized by the switch 186 comprising a removable isolating material (e.g., a paper or polymer strip, such as Mylar or Kapton), wherein the switch 186 is configured to close the electrical circuit upon removal of the isolating material. Alternatively, the single-use switch may be implemented as exposed contacts that are shorted together when the tracker 100 is assembled.

An electrical circuit may be configured to limit a radiant intensity of at least one IR-LED to not exceed 40 microwatts per steradian (μW/sr), preferably 20 μW/sr, more preferably 10 μW/sr. The electrical circuit may be configured to limit a maximum radiant intensity or average radiant intensity of at least one IR-LED to be in a range between 0.1 μW/sr and 40 μW/sr, for example between 0.5 μW/sr and 20 μW/sr or between 1 μW/sr and 10 μW/sr. The electrical circuit may be configured to limit a radiant intensity of some or all of a plurality of IR-LEDs to 40 μW/sr or less as indicated above.

The battery 182 may be realized as a single button cell (also called a coin cell). However, the battery 182 may also comprise a plurality of cells. Button cells are batteries with little weight resulting in a tracker 100 with a reduced weight. The battery 182 may have a mass of less than 5 grams, for example 3 grams. The battery 182 may be a primary battery that is not rechargeable or, alternatively, may be a secondary battery that is rechargeable. The battery 182 may utilize an anode material comprising zinc or lithium. The battery 182 may be an alkaline or lithium type, such as a commonly available CR2032 or CR2025 batteries having a circular or cylindrical shape. Alternatively, the battery 182 may be a zinc-air battery. The battery 182 may have a capacity of between 100 milliamp-hours (mAh) and 1000 mAh (e.g., between 200 mAh and 400 mAh).

Figure 6:
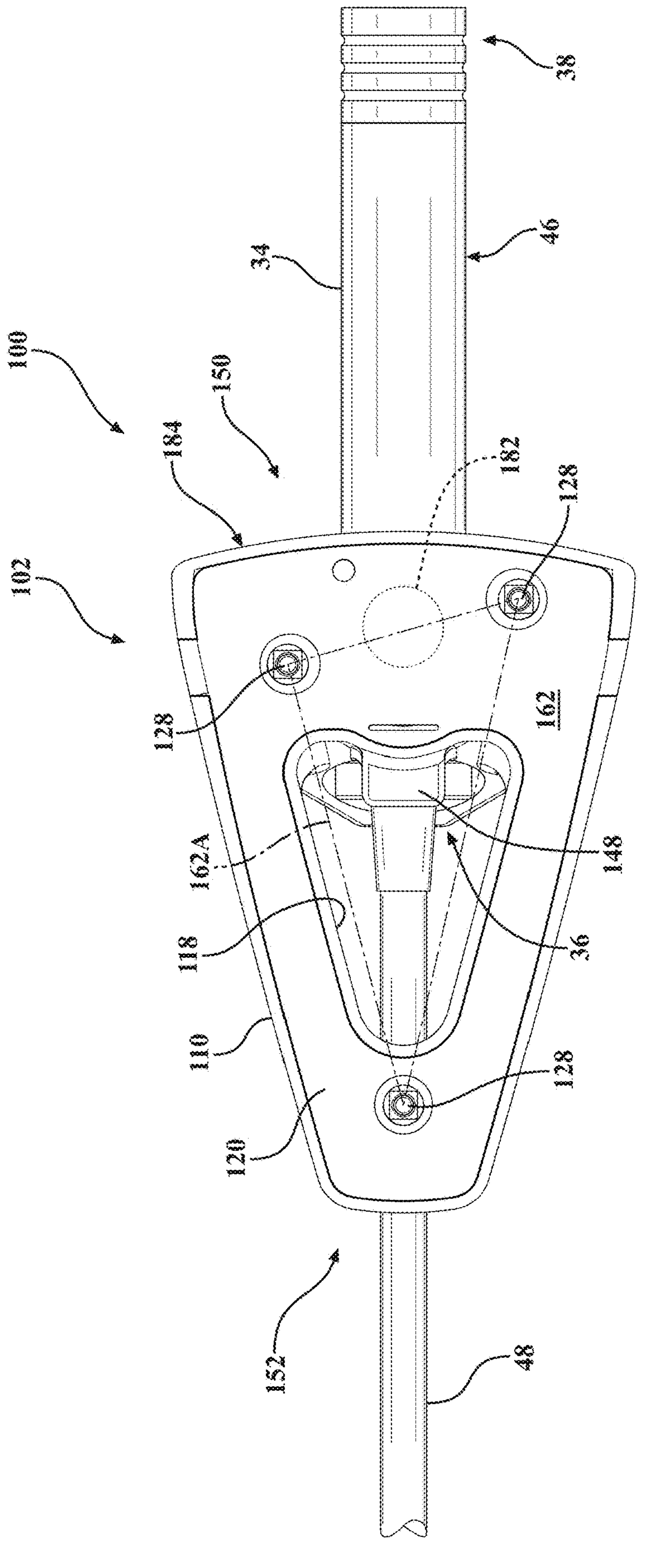
FIG. 6 is a top view of the tracker and surgical instrument of FIG. 2 showing a marker array and area.

In FIGS. 3 and 5-6 the battery 182 is displayed with dashed lines to indicate that the battery 182 is disposed in the interior 122 of the tracker 100 so as to protect the battery 182 from contaminants that may occur during surgery (e.g., blood, water, and sterilization agents). In the various embodiments shown throughout the figures the battery 182 may be removable from the tracker 100 by a user. Alternatively, the battery 182 may be non-removable from the tracker 100 by a user (e.g., when the tracker 100 is configured as a disposable item). Due to the limited current for at least one of the plurality of markers 128, the battery 182 may be sufficient as a power source and no external power source may be required. The tracker 100 may not comprise a power cord to an external power source.

The battery 182 provides a direct current voltage of, for example, 3V. Each of the IR-LEDs has an operation voltage of, for example, 1.5V. Therefore, 3V−1.5V=1.5V of the battery voltage drops off at each of the resistors. The electrical resistance of each resistor is 150Ω. Therefore, the current through each resistor and consequently each IR-LED is 1.5V/150Ω=10 mA. Due to the provision of the resistors the electrical circuit is configured to limit a current for each of IR-LEDs to not exceed 15 mA. In this way, the electrical circuit also limits the radiant intensity of at least one of the IR-LEDs to not exceed 40 μW/sr lumen.

The coin cell of the battery 182 has a low weight, but also a small capacity (e.g., 520 mAh). Since the electrical circuit is optionally configured to limit the current for each of the IR-LEDs to not exceed 15 mA or 20 mA, the capacity of a coin cell is still sufficient to safely operate the tracker 100 for the duration of a typical surgical navigation procedure. For example, with a CR2032 type battery having a capacity of 520 mAh and providing power to four IR-LEDs each with a current of 10 mA, the tracker 100 can be operated for a duration of 520 mAh/(4×10 mA)=5.5 h. The tracker 100 may be configured to house additional batteries to increase the duration the tracker 100 may be operated. For example, a tracker with two 520 mAh batteries may be operated for a duration in excess of 10 h.

Because the current load is decreased the tracker 100 is configured for continuous operation of the markers 128. The tracker 100 may be configured to operate at least two of the plurality of the markers 128 simultaneously. The tracker 100 may further be configured to operate all of the markers 128 simultaneously. Alternatively, the tracker 100 may be configured to operate the plurality of markers 128 sequentially.

Alternatively, the tracker 100 may be configured for quasi-continuous or pulsed operation. The quasi-continuous operation may further include circuitry capable of adjusting the brightness of the markers 128, such as via a pulse-width-modulation (PWM) circuit, where a duty-cycle of the electrical signal supplied to the marker 128 is modified to be on for a greater proportion of time than it is off, thereby increasing the brightness, and vice versa. The quasi-continuous operation may be performed at an operation frequency of over 0.5 kHz. Such a quasi-continuous operation reduces the power consumption of the tracker 100.

In addition to the IR-LEDs mentioned above, the tracker 100 may further comprise circuitry for a status indicator electrically coupled to at least one of the IR-LEDs, the battery, and the resistors. In one implementation, the status indicator may comprise an LED that emits visible (i.e. non-infrared) light so that a surgeon can easily verify that the tracker 100 has been activated and is functioning. The status indicator may be configured to provide additional diagnostic or operational information to the surgeon, such as remaining battery capacity. For example, the status indicator may flash or blink when the battery voltage corresponds to a first level, and when the battery voltage corresponds to a second level the status indicator may turn off. The status indicator may further be implemented with more than one LED, or an LED capable of illuminating with more than one color. If more than one LED is used the voltage level of the battery may correspond to the number of LEDs that are concurrently illuminated. If multi-color LEDs are used the color may correspond to the voltage level of the battery.

As mentioned above, the markers 128 are positioned around the longitudinal axis 108, either by arrangement in each of the radial segments 112, 114, 116, or with a certain quantity located on one side of the longitudinal plane 168. These configurations increase the visibility of the tracker 100, and therefore the ability of the surgical navigation system to accurately determine the position and orientation of the surgical instrument 34. Further, these configurations position the markers 128 at multiple angular positions about the longitudinal axis 108 such that the markers 128 are capable of radially emitting infrared radiation or light at least 260 degrees about the longitudinal axis 108. This radial emission is shown in FIG. 7, where an exemplary emission pattern for each of the plurality of markers 128 is shown relative to the tracker 100 and the surgical instrument 34. The radial emission shown here is 360 degrees about the longitudinal axis 108. Here again, the markers 128 are IR-LEDs, having a hypothetical total emission angle 174 of approximately 150 degrees. Said differently, each of the IR-LEDs is capable of emitting radiation of at least 50% of its peak intensity at an angle that is 75 degrees from a normal line 175 (see FIG. 25), or centerline, of the peak intensity, this angle is commonly referred to as a half-angle. The normal line 175 of the IR-LED is generally orthogonal to a mounting plane of the IR-LED and defines the centerline of peak intensity. IR-LEDs that have larger or smaller half angle values may be implemented in the alternative, such as 65 degrees or 85 degrees. The configuration of the IR-LEDs having an exemplary emission angle 174 of 150 degrees allows the radiation or light emitted from the IR-LEDs to be visible to the navigation system through approximately 360 degrees of rotation of the tracker 100 on the longitudinal axis 108, as may occur during the course of a surgical procedure as the surgeon operates the surgical instrument 34 as necessary.

In some embodiments a distance between at least two of the plurality of markers 128 may be smaller than 70 millimeters (mm). A distance between at least two of the plurality of markers 128 may be in a range between 1 mm and 70 mm, for example between 3 mm and 35 mm or between 5 mm and 30 mm. As will be discussed below, the markers 128 may be disposed in a common plane. Alternatively, the markers 128 may be configured such that they are not be disposed in a common plane.

Turning to FIG. 11 each electrical circuit comprises an IR-LED (i.e. marker 128), which is attached (e.g. via soldering) to a printed circuit board (PCB) 176, 178, 180, which in turn is coupled to the tracker frame 102. Here, three PCBs 176, 178, 180 are shown, wherein three markers 128 are coupled to each PCB 176, 178, 180. Each of the PCBs 176, 178, 180 is in electrical communication with a voltage source, shown here as the battery 182, which is used to provide power to the plurality of markers 128. The PCBs 176, 178, 180 have a generally flat and planar configuration, with the markers 128 and other components (such as the resistors discussed herein) attached thereto. More specifically, each PCB 176, 178, 180 defines a plane 176A, 178A, 180A that is generally normal to the direction that the respective markers 128 emit radiation. The two or more, or three or more PCBs 176, 178, 180 are arranged such that they are non-parallel to each other. In some configurations the battery 182 may be coupled to the electrical circuit on only one of the PCBs 176, 178, 180. Here, the battery 182 is electrically coupled to the upper PCB 176. Each of the other PCBs 178, 180 is electrically coupled to the upper PCB 176 via wiring in order to provide power to all of the markers 128. Alternatively, all of the markers 128 may be coupled to a single flexible PCB, which is configured with flexible portions allowing the PCB to have a single surface that is oriented in at least three different directions.

Figure 22:
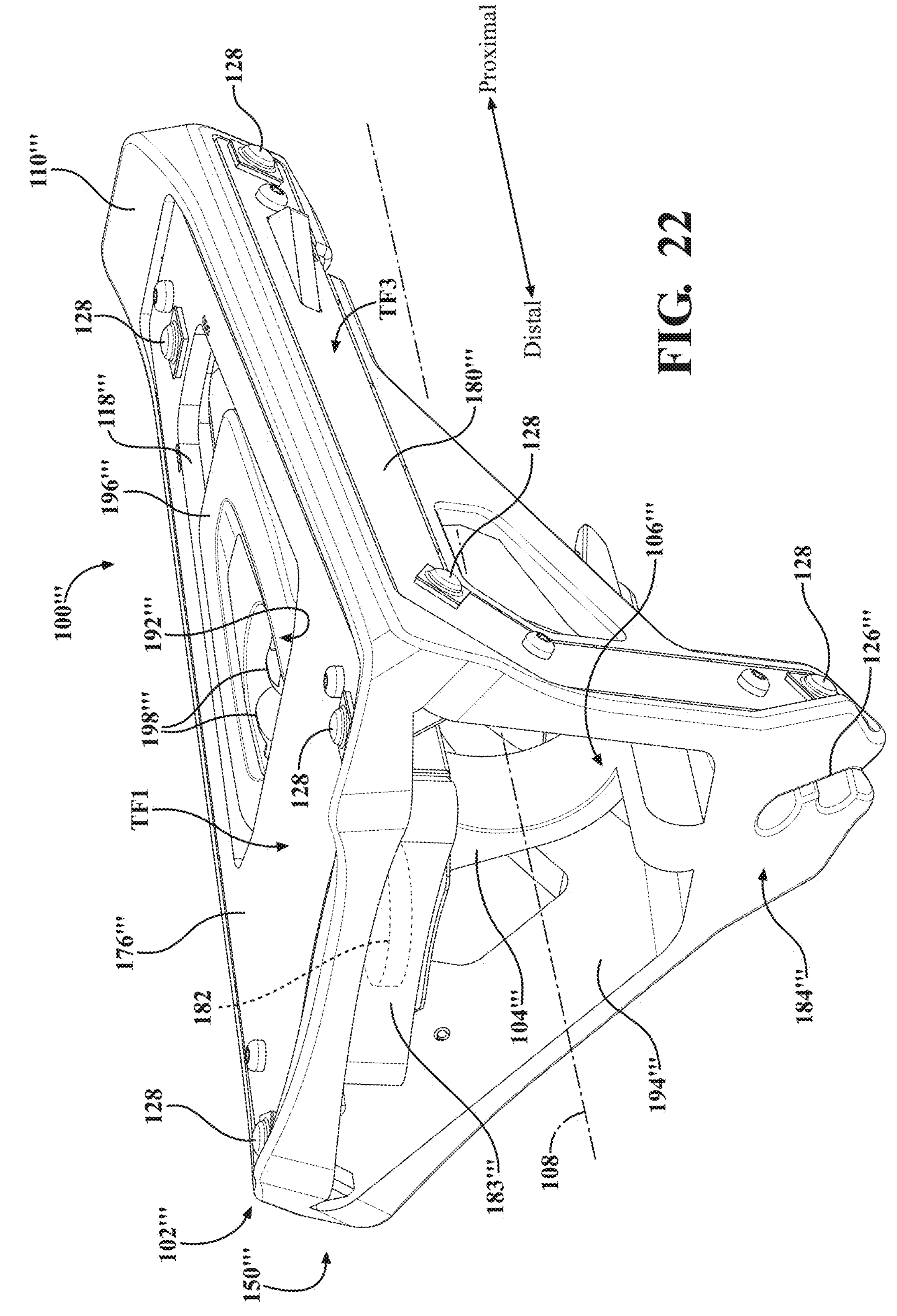
FIG. 22 is a perspective view of another embodiment of a tracker.
Figure 23:
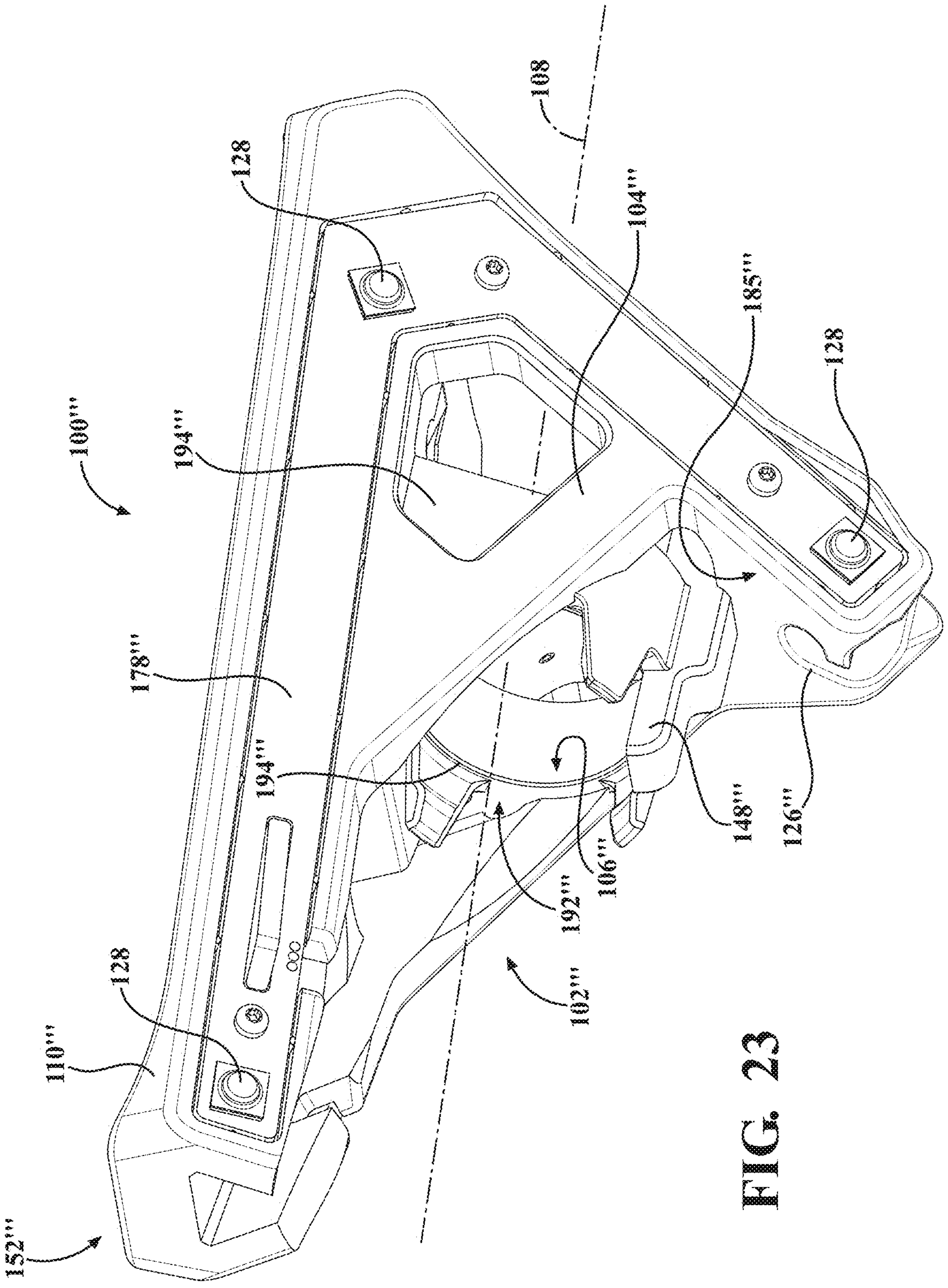
FIG. 23 is a perspective view of the tracker of FIG. 22.

As will be discussed below in connection with the fourth embodiment of the tracker 100" shown in FIG. 22, some embodiments may comprise a battery receptacle such as a tray 183", which holds the battery 182 and may be slidably engageable with the tracker frame 102" to place the battery 182 in electrical communication with the IR-LEDs. In some configurations, the battery 182 and battery tray 183 are arranged to directly engage the PCB in a low-profile configuration. When the battery 182 is configured as a button cell battery (e.g. a CR2032, as described above), one of the circular faces of the battery contacts conductive elements of the PCB. By placing the battery 182 in contact with the PCB an overall height of the PCB assembly is minimized. As discussed above, reducing the height of the tracker 100 advantageously reduces the angle of the sightline 188 during use.

Because the markers 128, when configured as infrared emitters or IR-LEDs, are coupled to the respective non-parallel PCBs 176, 178, 180, each marker 128 emits radiation normal to the plane 176A, 178A, 180A on which it is disposed. Therefore, the markers 128 collectively emit radiation in at least as many directions as there are non-parallel planes 176A, 178A, 180A. Again referring to FIG. 7 where three different directions are shown.

In order to capitalize on the radial emission characteristics afforded by the configuration of markers 128, the surgical navigation system may be able to determine which markers 128 correspond to a particular arrangement on the tracker frame 102. As mentioned above, the plurality of markers 128 are arranged to form at least two arrays, with each array having at least three markers 128, a portion of each array coupled to the offset body 110. More specifically, the tracker 100 shown in FIG. 11 comprises three arrays 162, 164, 166 coupled to the tracker frame 102. A first array 162 is coupled to the offset body 110 and faces toward the top of FIG. 11. A second array 164 is coupled to both the mounting body 104 and the offset body 110 and faces toward the lower left of FIG. 11. A third array 166 is also coupled to both the mounting body 104 and the offset body 110 and faces toward the lower right of FIG. 11. However, other array arrangements are contemplated.

In addition to a portion of each at least two arrays 162, 164, 166 being coupled to the offset body 110, a portion of each at least two arrays 162, 164, 166 is positioned proximally of said mounting body 104, and the portion of the at least two arrays 162, 164, 166 is positioned proximally of said mounting body 104 comprises exactly one marker 128. As mentioned above, a portion of the offset body 110 protrudes from the mounting body 104 in a proximal direction and terminates at a proximal end 152. This proximal end 152 of the offset body 110, and likewise the tracker frame 102, is positioned proximally of the proximal end 36 of the surgical instrument 34. Best shown in FIG. 7, three markers 128, one each from the first array 162, the second array 164, and the third array 166 are arranged on the tracker frame 102 at a position that is proximal of the proximal end 36 of the surgical instrument 34, near the proximal end 152 of the offset body 110.

The camera comprises two lenses for focusing the infrared light emitted by the plurality of the IR-LEDs. The lenses enable a larger amount of light to enter the camera compared to a non-focusing opening like a slit aperture. Therefore, the camera is capable of detecting light sources with a low brightness, such as the IR-LED being operated with limited currents.

The camera further comprises two two-dimensional image sensors 66. The two-dimensional image sensors 66 are capable of sensing a solid angle (i.e., a two-dimensional angle). A conventional one-dimensional sensor row, on the other hand, typically requires synchronization with the detected light source and may only allow tracking of a single light source per scan. Since the two-dimensional image sensors 66 can detect all IR-LEDs at once, the tracker 100 may be configured to operate at least two and in particular all of the plurality of the IR-LEDs simultaneously. Such a simultaneous operation requires no synchronization of the camera with the tracker 100. Therefore, the tracker 100 does not require a communication interface (e.g., a wireless transceiver) for communicating with the camera, which further reduces the weight of the tracker 100. Further advantages of a tracker 100 without a transceiver include preventing transmitted signals from undesired interference with outside systems, prevention of undesirable signal interference in received signals, reduced cost, and reduced complexity.

The surgical navigation system may comprise two two-dimensional image sensors that are part of a stereo camera. Such a stereo camera is capable of capturing three-dimensional image data. Therefore, a known spatial relation between the IR-LEDs is not necessary. A stereo camera may thus be employed when a plurality of single IR-LEDs are attached to a patient. Due to manual attachment, the spatial relation between the IR-LEDs is unknown. However, since the stereo camera is capable or capturing three-dimensional image data, the IR-LEDs can be tracked by the stereo camera.

In one configuration, identification of each of the arrays 162, 164, 166 is performed by the surgical navigation system by determining the distance to each marker 128 and triangulating a position from the camera, discussed above. Independently tracking each array 162, 164, 166 in more than one dimension (e.g. 2D, or 3D) is accomplished by configuring the arrays 162, 164, 166 with more than one marker 128. As shown throughout the figures, each array 162, 164, 166 is defined by three markers 128, for a total of nine markers 128. In order to accurately differentiate between each array 162, 164, 166, the specific arrangement of the markers 128 may vary between each of the arrays 162, 164, 166. In one example, the first array 162 may define a first area 162A (FIG. 6), which is the area of a triangle with vertices at a common reference on each of the respective markers 128. Likewise, the second array 164 may define a second area 164A (FIG. 8) and the third array 166 may define a third area 166A (FIG. 5), both the second area 164A and the third area 166A are based on the area of a triangle with vertices at a common reference on each of the respective markers 128. Here, the first area 162A may be greater than the second area 164A, and the second area 164A may be greater than the third area 166A.

In another example, particularly the tracker 100" (discussed in further detail below) shown in FIGS. 22-26, the second area 164A" and the third area 166A" may be equal.

Here, the second array 164" and the third array 166" may be configured with the markers 128" in the same position relative on the respective array. The second array 164" and the third array 166" may be dimensionally identical (or substantially the same) in an opposite or mirrored configuration. This may provide for a pleasing appearance and reduced cost of manufacture.

Referring now to FIGS. 12-16, another implementation of the tracker 100' is shown in which the tracker frame 102' comprises a cam lock retention mechanism 136'. In many respects, the tracker 100' may be similar to that previously described with like numerals (plus a prime symbol (')) corresponding to like components, and any disclosure common to the corresponding components may be considered omitted in the interest of brevity should not be construed as limiting. It should be understood that counterpart components on the tracker frame 102' may be modified in an appropriate manner to permit the surgical instrument 34 to be inserted into and removed from the instrument engaging aperture 106' in the manners previously described. Further, it should be understood that, while discussed in the context of the retention mechanism 132', which may be integrated with or coupled to any mounting body 104', for example the mounting body 104 previously described, the disclosure may be applicable to the tracker 100' and/or the tracker frame 102' more generally.

In FIGS. 12-16, the tracker 100' is shown comprising the tracker frame 102', having the mounting body 104' and the offset body 110' supported thereon. Similar to above, the mounting body 104' defines the instrument engaging aperture 106', which is configured to slidably engage the surgical instrument 34 at a proximal end 36. The distal end 38 of the surgical instrument 34 is inserted into the proximal side of the instrument engaging aperture 106' and slid in a distal direction until a collar coupled to the proximal end 36 of the surgical instrument 34 and having a diameter larger than the instrument engaging aperture 106' abuts the mounting body 104'. The collar defines the complementary shaped recess in the housing 46 of the surgical instrument 34, which is configured to engage the attachment protrusion 148' adjacent to the instrument engaging aperture 106'. Here, the retention mechanism 132' has a release knob with an angled cam surface that engages the collar of the surgical instrument 34, which biases the surgical instrument 34 towards engagement with the instrument engaging aperture 106'. Moving the knob to a release position disengages the collar and allows the surgical instrument 34 to be removed from the tracker 100'.

Figure 16:
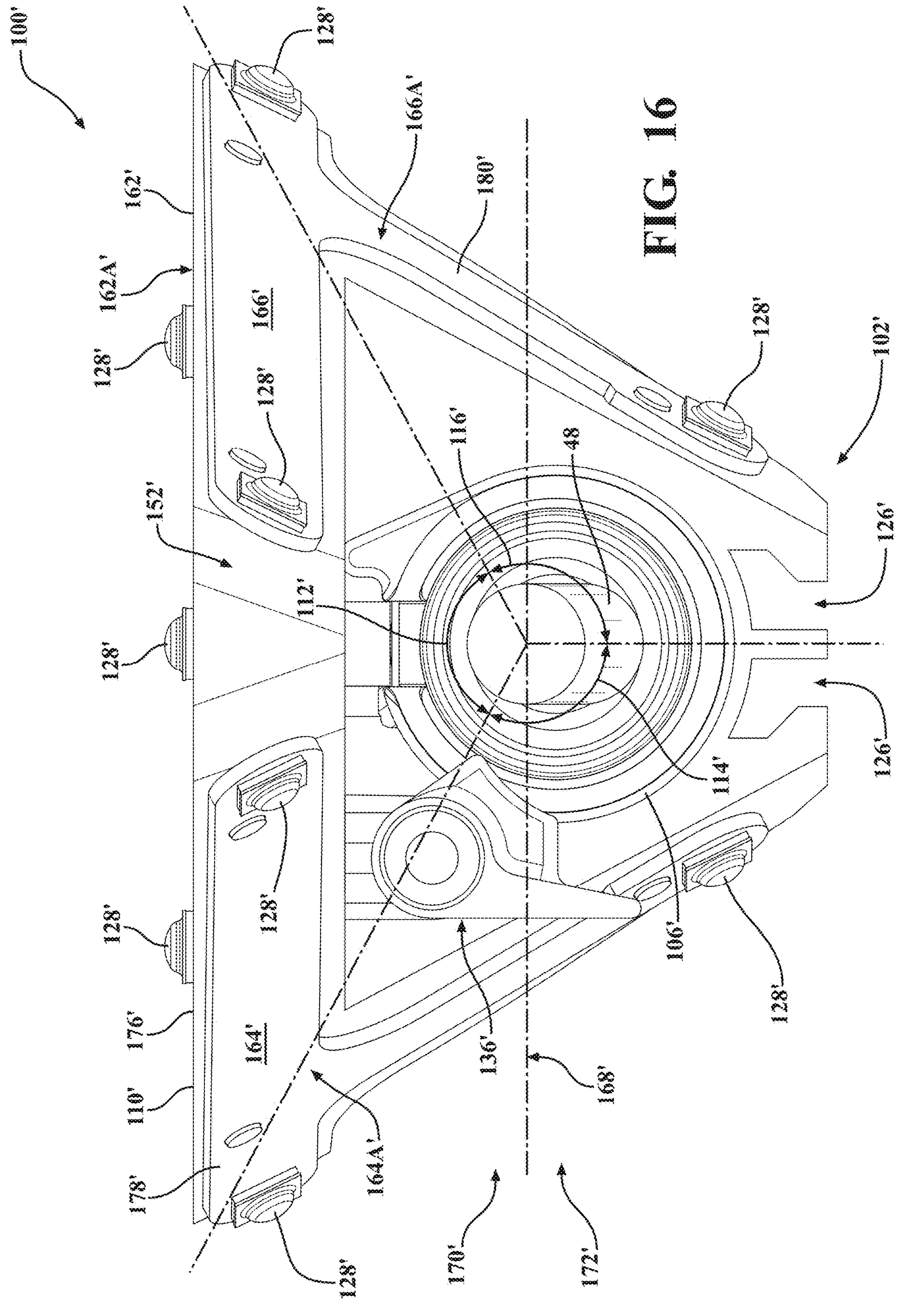
FIG. 16 is a proximal view of the tracker of FIG. 12.
Figure 17:
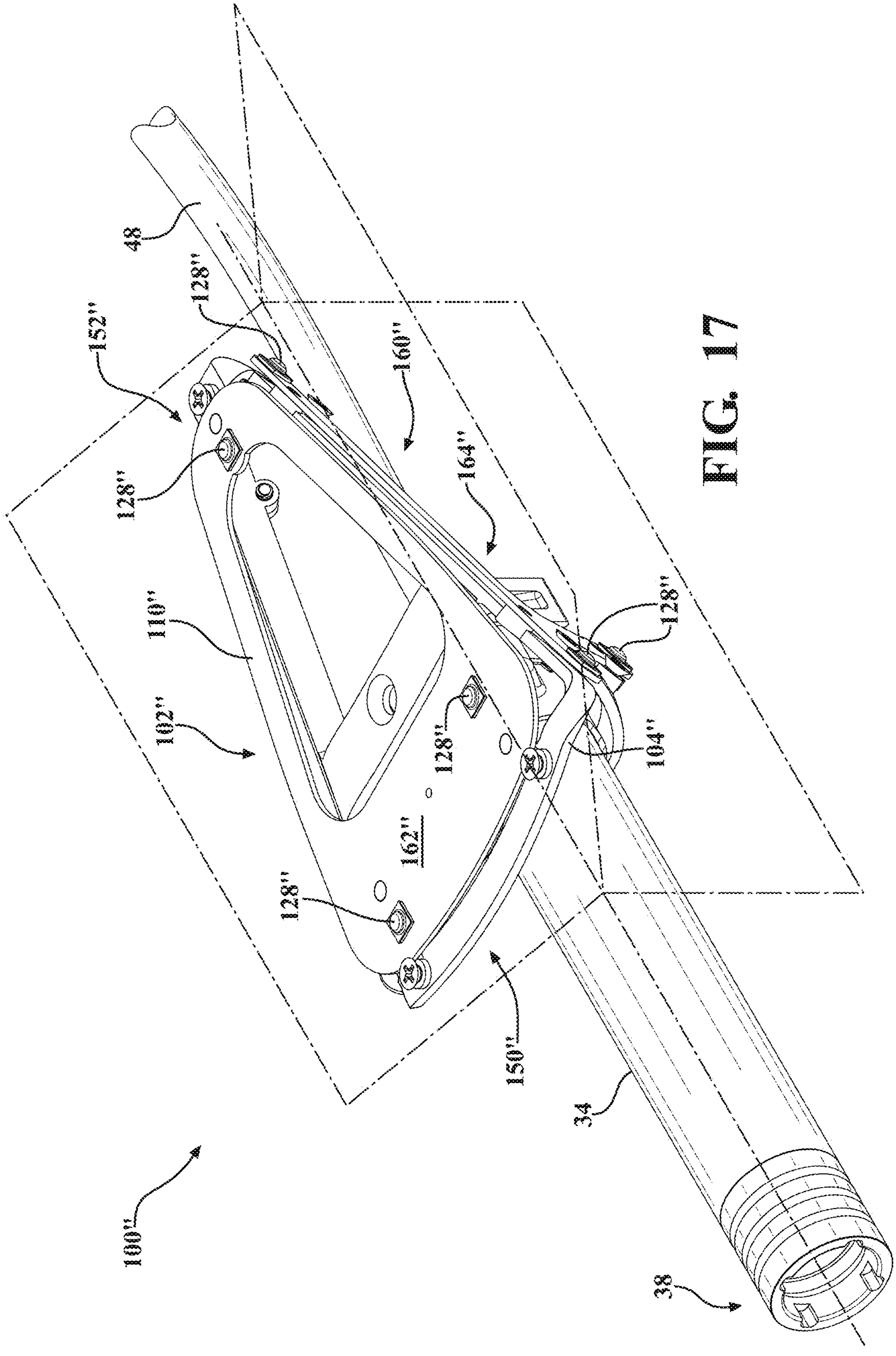
FIG. 17 is a perspective view of yet another embodiment of a tracker shown coupled to a surgical instrument.

FIG. 16 shows the radial segments 112', 114', 116' as they are arranged about the longitudinal axis 108'. The asymmetric arrangement of the markers 128' on the tracker body 102' facilitates an increased visibility of the tracker 100' by the surgical navigation system by emitting infrared radiation or light in at least 260 degrees about the longitudinal axis 108'. Some arrangements of the markers 128' may emit light 360 degrees about the longitudinal axis 108'.

Referring now to FIGS. 17-21, another implementation of the tracker 100" is shown in which the tracker frame 102" is a space frame construction. Here too the tracker 100" comprises a cam lock retention mechanism 136". In many respects, the tracker 100" may be similar to that previously described with like numerals (plus a double-prime symbol (")) corresponding to like components, and any disclosure common to the corresponding components may be considered omitted in the interest of brevity should not be construed as limiting. It should be understood that counterpart components on the tracker frame 102" may be modified in an appropriate manner to permit the surgical instrument 34 to be inserted into and removed from the instrument engaging aperture 106" in the manners previously described. Further, it should be understood that, while discussed in the context of the tracker frame 102", the disclosure may be applicable to the tracker 100" and/or the tracker frame 102" more generally.

In FIGS. 17-21, the tracker 100" is shown comprising the tracker frame 102", having the mounting body 104" and the offset body 110" supported thereon. Similar to above, the mounting body 104" defines the instrument engaging aperture 106", which is configured to slidably engage the surgical instrument 34 at a proximal end 36. The distal end 38 of the surgical instrument 34 is inserted into the proximal side of the instrument engaging aperture 106" and slid in a distal direction until a collar coupled to the proximal end 36 of the surgical instrument 34 and having a diameter larger than the instrument engaging aperture 106" abuts the mounting body 104".

Figure 21:
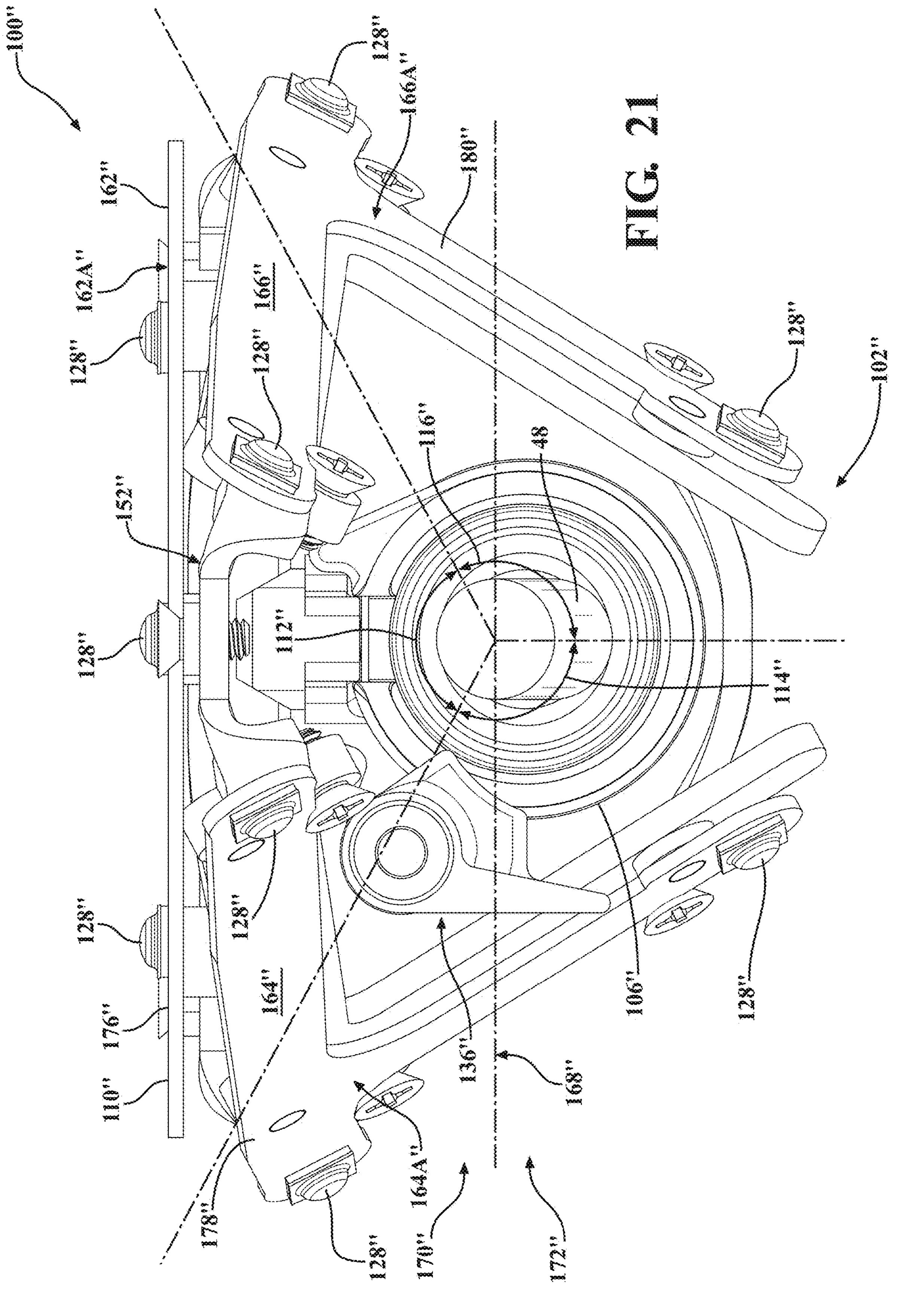
FIG. 21 is a proximal view of the tracker of FIG. 17.

In this implementation the tracker frame 102" is formed from a bent plate, thereby forming each of the three sides. The tracker frame 102" is bent such that each side aligns with the three radial segments 112", 114", 116", which are shown in FIG. 21. The tracker frame 102" is formed from a metallic material such as titanium, which is lightweight and durable. Because the tracker 100" is intended to be reusable, the construction permits certain components to be serviced or replaced. For example, the at least two arrays 162", 164", 166" are coupled to the tracker frame 102" with threaded fasteners. Similarly, this allows the at least two arrays 162", 164", 166" to be removed for cleaning.

As with before, the plurality of markers 128" are arranged on the tracker frame 102" such that at least one marker 128" is positioned in each of the radial segments 112", 114", 116". Additionally, FIG. 21 shows an edge of a longitudinal plane 168", which is parallel to the longitudinal axis 108" and bisects the instrument engaging aperture 106" to define the first region 170" and the second region 172". The arrangement of the markers 128" is further defined with respect to the first region 170" and the second region 172", wherein a first quantity of the plurality of markers 128" are positioned in the first region 170", and a second quantity of the plurality of markers 128" are positioned in the second region 172", the first quantity being greater than the second quantity.

Figure 18:
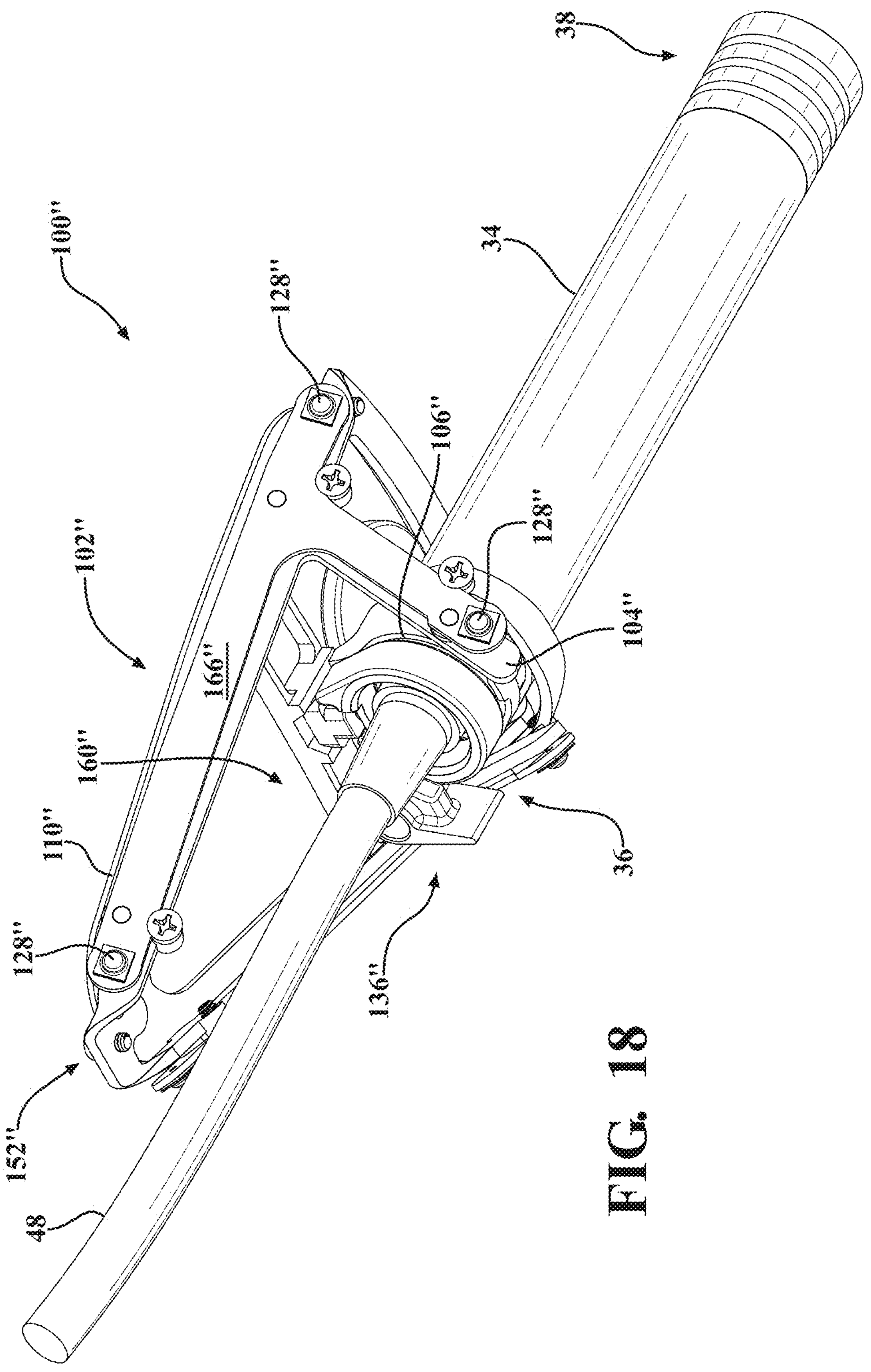
FIG. 18 is another perspective view of the tracker of FIG. 17.
Figure 19:
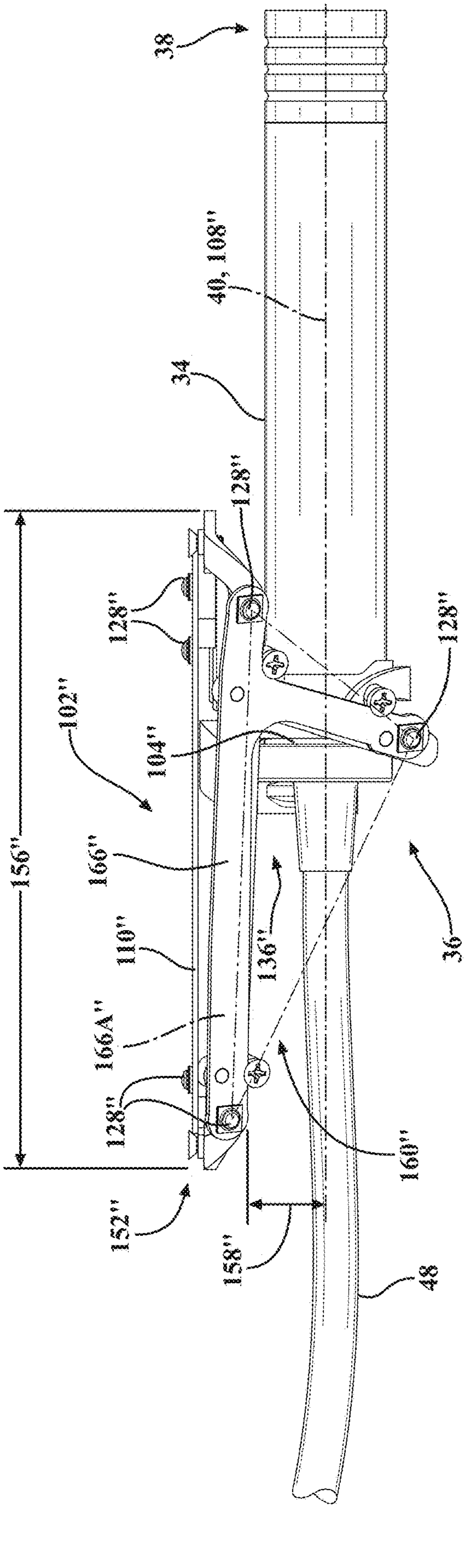
FIG. 19 is a side view of the tracker of FIG. 17.
Figure 20:
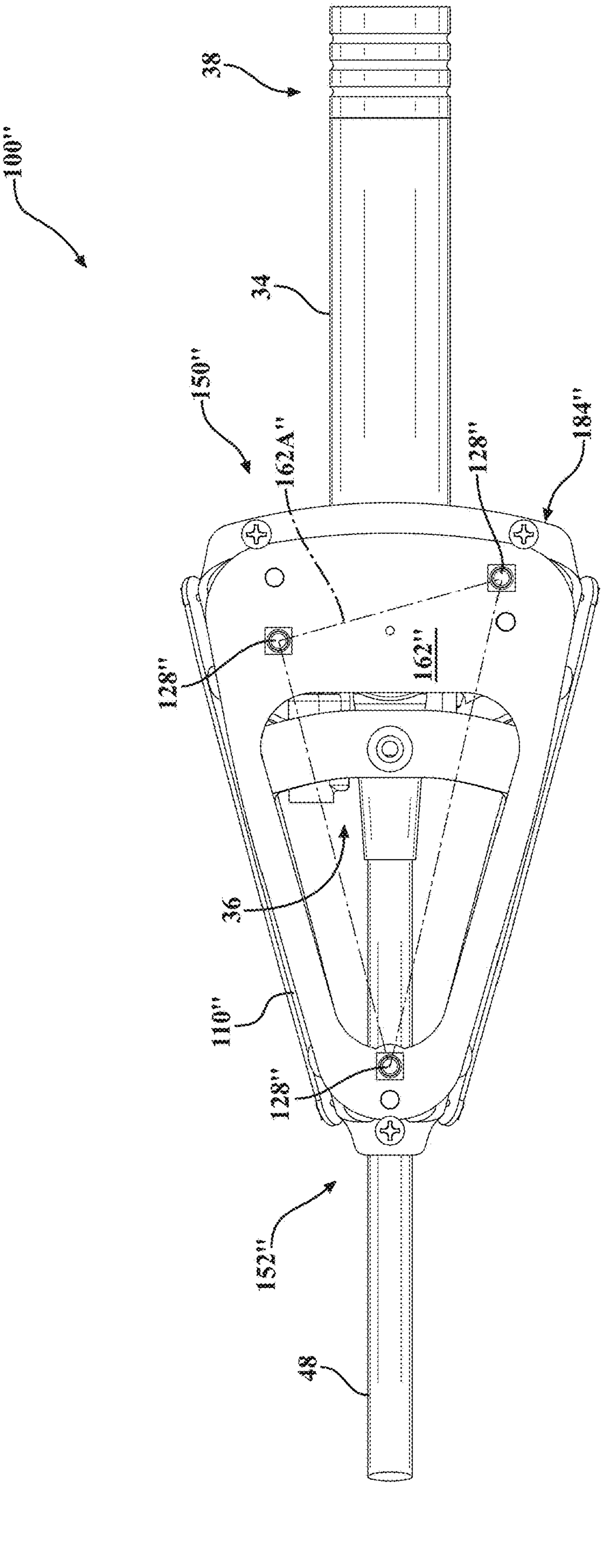
FIG. 20 is a top view of the tracker of FIG. 17.

FIG. 18 shows the proximal end 152" of the offset body 110" spaced about the longitudinal axis 108" to define the relief area 160", which provides clearance for the flexible supply cable 48. Here too, a portion of the at least two arrays 162", 164", 166" is positioned proximally of the mounting body 104", and this portion comprises exactly one marker 128".

Some embodiments of the tracker 100 may be configured with the PCBs as outward facing exterior surfaces where they may be exposed and susceptible to contact with debris or fluids. A short circuit may result in damage to the components coupled to the PCB such as the markers 128 or the resistors, which may cause undesirable operation of the tracker 100. The PCBs and components forming each of the tracker arrays may be protected by the application of a conformal coating, which creates a barrier on the PCB preventing the ingress of debris and fluids. Exemplary conformal coatings may comprise a parylene film applied to assembled PCBs.

Referring now to FIGS. 22-26, another alternative implementation of the optical tracker 100''' is shown without the handheld surgical instrument 34. In this implementation of the tracker 100''', the retention mechanism 132 takes the form of a lever clamp 192'''. As above, in many respects, the tracker 100' may be similar to that previously described with like numerals (plus a triple prime symbol (''')) corresponding to like components, and any disclosure common to the corresponding components may be considered omitted in the interest of brevity should not be construed as limiting. Here, the lever clamp 192''' comprises two resilient arms 194''' coupled to the tracker frame 102''' at a first end and spaced from each other at a second end, and a lever 196''' pivotably coupled to the second end of the resilient arms 194'''. The resilient arms 194''' cooperate to define the instrument engaging aperture 106''', which extends along the longitudinal axis 108''' within the mounting body 104'''.

The offset body 110''' is supported on the mounting body 104''' and extends in a proximal direction. The offset body 110''' is spaced from the longitudinal axis 108''' and defines the cutout 118''', which extends through the offset body 110''' in a direction generally perpendicular to the longitudinal axis 108'''. Within the offset body 110''', shown here having a triangular shape corresponding to one face of the generally tetrahedral-like shape of the tracker frame 102''', is the lever 196'''. The lever 196''' is pivotable between a clamped position and an unclamped position (not shown) to secure the tracker frame 102''' to the surgical instrument 34.

Each resilient arm 194''' has an ear portion 198''' at one end. The lever 196''' is engaged with each ear portion 198''' and pivotable about a lever axis that is generally perpendicular to the longitudinal axis 108''' of the tracker frame 102'''. In one instance each ear portion 198''' may define a lever support bore, which extends along the lever axis through the ear portions 198'''. The lever 196''' may comprise two pins arranged on the lever axis and engageable with the lever support bores. The engagement between the pins and the lever support bores facilitates the pivoting movement of the lever 196''' between the clamped position and the unclamped position. In another instance the lever 196''' and the ear portions 198''' may be configured with the pins protruding from the ear portions 198''' and the lever support bore defined in the lever 196'''.

As mentioned above, the tracker frame 102''' may comprise a plastic or a polymer material. As such, the tracker frame 102''' may be formed using an injection molding or additive manufacturing process, which forms the tracker frame 102''' as a single unitary body. By forming the tracker frame 102''' as a single unitary body steps such as assembling the clamp 192''' to the tracker frame 102''' may be eliminated. Furthermore, dimensional accuracy of the tracker frame 102''' may be increased by reducing tolerance stack-ups. In addition, by eliminating any joints between pieces, the stiffness of the tracker frame 102''' may be increased. Geometry that would be formed for the purpose of joining multiple piece together may be eliminated further reducing the weight of the tracker frame 102''' and the need to control the accuracy of mating surfaces. When formed from a plastic or polymer material, the resilient arms 194''' may flex slightly, which allows the ear portions 198''' to be displaced relative to each other, thereby allowing a distance defined therebetween to be reduced. When the user pivots the lever 196''' from the unclamped position to the clamped position the ear portions 198''' are moved closer together, which reduces a diameter of the instrument engaging aperture 106'''. When the surgical instrument 34 is inserted in the instrument engaging aperture 106''' and the lever 196''' pivoted into the clamped position, the resilient arms 194''' are tightened against an outer surface of the surgical instrument 32 and prevent relative movement therebetween.

The structure of the trackers 100, 100', 100'', 100''' described herein are optimized to reduce both mass and size in furtherance of creating a low-cost disposable tracker. In some embodiments the mass of the tracker including the battery may be 40 g. Some embodiments of trackers, including the power source, may have a mass of less than 50 g, 40 g, or less than 35 g.

Figure 24:
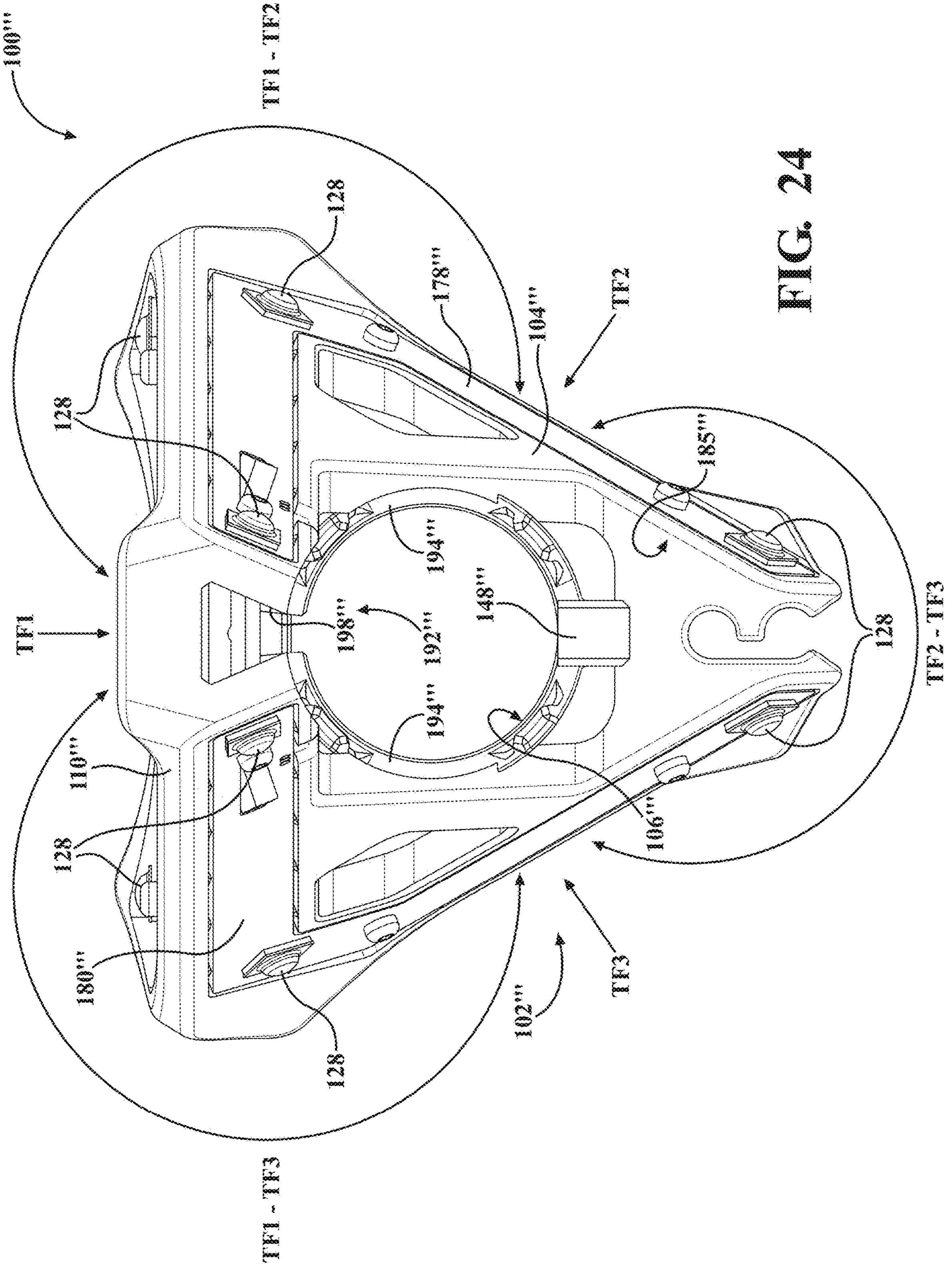
FIG. 24 is a proximal view of the tracker of FIG. 22.
Figure 25:
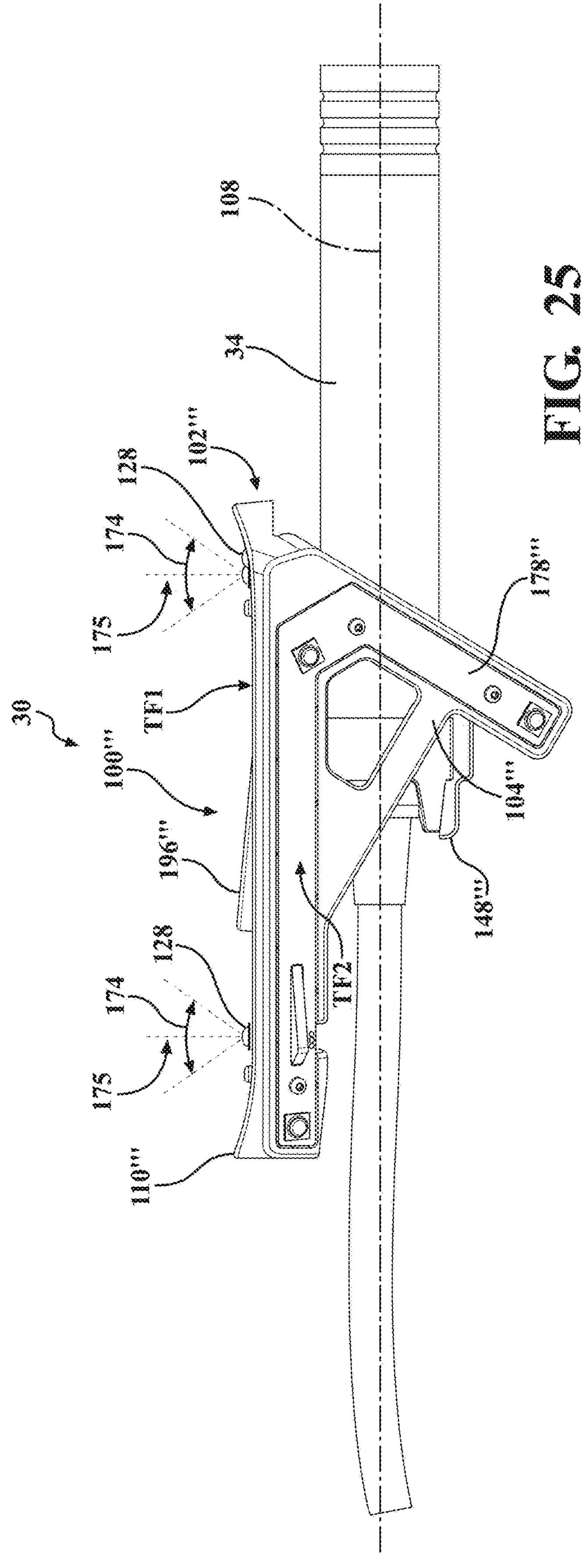
FIG. 25 is a side view of the tracker of FIG. 22 coupled to the surgical instrument.
Figure 26:
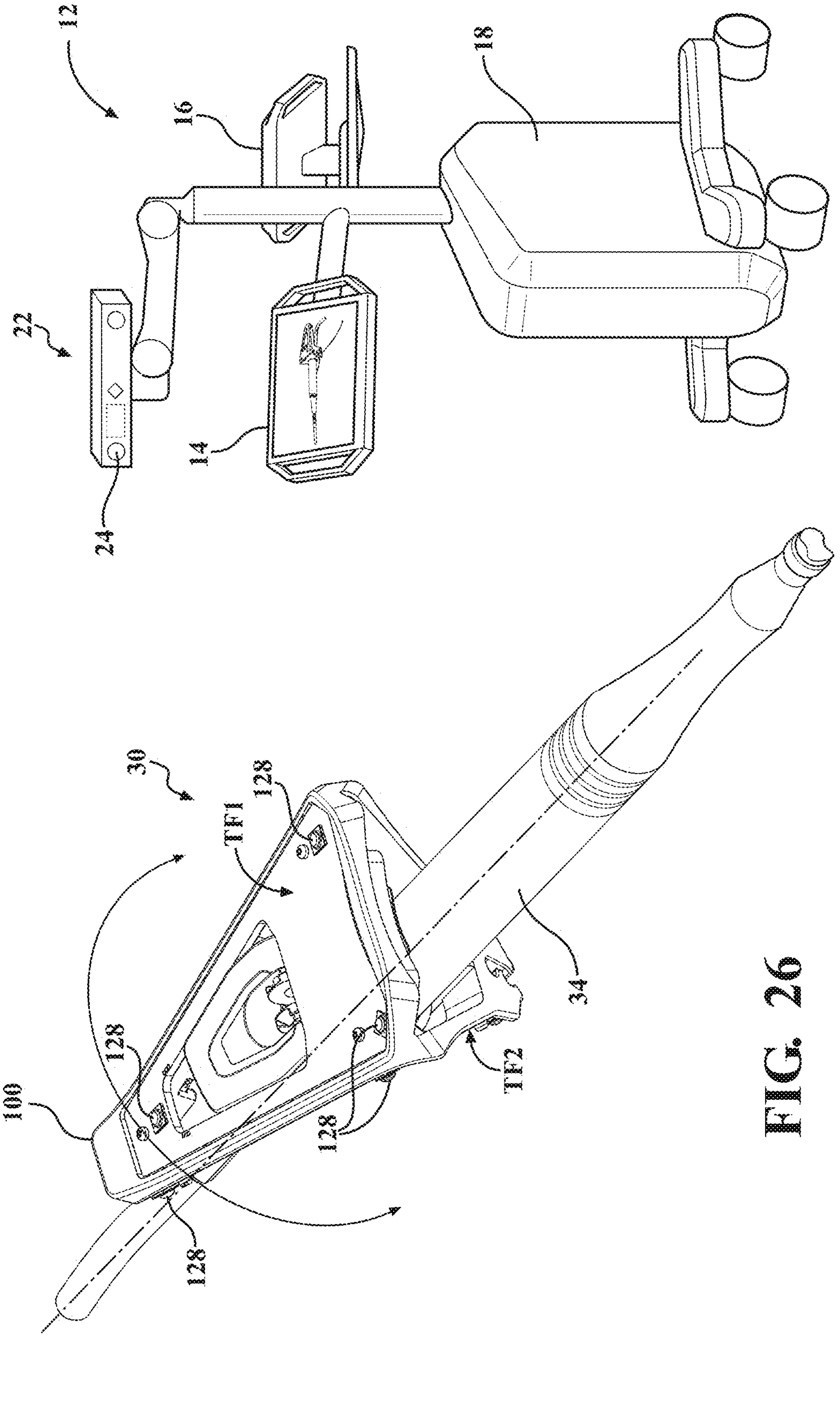
FIG. 26 is a perspective view of the tracker and a surgical navigation cart.

Also disclosed is a method for calibrating and registering the tracker 100 and tracking array for a surgical procedure using a localizer. Turning to FIGS. 24-26, steps for calibrating and registering the tracking array having a first tracking face TF1 and a second tracking face TF2 coupled to one another are illustrated. The tracking array may further include a third tracking face TF3 coupled to both the first tracking face TF1 and the second tracking face TF2. The method steps are illustrated in the context of the fourth implementation of the tracker 100'' described above, however the steps are applicable to each of the trackers 100, 100', 100'', 100''' described herein. As such, any of the trackers 100, 100', 100'', 100''' may be calibrated according to the method described below. The elements described in connection with the method are generally similar among each of the four implementations with like numerals corresponding to like components and any primes omitted in the interest of clarity.

The tracker is calibrated in the operating room to achieve high tracking accuracy. A high tracking accuracy may correspond to accurate and precise measurements of the relative position of each of the optical tracking elements. By calibrating the tracker in situ, the navigation system can precisely measure the position of each of the optical tracking elements to compensate for high manufacturing tolerances. Due to the high degree of accuracy that can be achieved by the calibration procedure the tracker can be manufactured in such a way that may result in a lower cost and a lighter weight. In an exemplary implementation of the tracker, the tracker frame may be formed using a stereolithography process and an epoxy resin.

Calibration and registration of the tracking array may be initiated by a user, such as the surgeon, before or at a beginning of the surgical procedure by coupling the tracker 100 to the medical instrument 34 or a patient, and activating the tracker 100 (e.g., by actuating the single-use switch). Alternatively, the calibration and registration procedures may be initiated automatically by the surgical navigation system 12 upon identifying the tracker or via the user input 16. Upon initiating calibration and registration the navigation processor 18 may provide a first set of instructions to the user on the display unit 14. These instructions may be a static list of steps or, as will be discussed below, may update dynamically.

Some embodiments of the surgical navigation system 12 comprise a memory device (not shown), which may have manufacturing dimensions of the tracking array stored thereon. The manufacturing dimensions may include a first set of geometrical data including first tracking face TF1 geometrical data, second tracking face TF2 geometrical data, and third tracking face TF3 geometrical data. The first tracking face geometrical data may include data indicative of expected relative positions of the plurality of optical tracking elements 128 on the first tracking face TF1, their position with respect to one another, and an expected direction of facing of the plurality of optical tracking elements 128 on the first tracking face. The second tracking face geometrical data may include data indicative of the expected relative positions of the plurality of optical tracking elements 128 on the second tracking face TF2, their position with respect to one another, and an expected direction of facing of the plurality of optical tracking elements 128 on the second tracking face 128. The third tracking face geometrical data may include data indicative of the expected relative positions of the plurality of optical tracking elements 128 on the third tracking face TF3, their position with respect to one another, and an expected direction of facing of the plurality of optical tracking elements on the third tracking face TF3. These data may further comprise the distances between individual optical tracking elements 128, the angles of the normal line 175, expected manufacturing positional tolerances, and other data that may characterize the tracking array.

The first tracking face TF1, the second tracking face TF2, and the third tracking face TF3 may each include a plurality of optical tracking elements 128 that are detectable by the navigation system 12. Calibration of the tracker 100 may be initiated by positioning the tracking array such that the plurality of optical tracking elements 128 of at least two of the first tracking face TF1, the second tracking face TF2, and/or the third tracking face TF3 are at least partially visible to the localizer 22. In a next step, the relative positions of the plurality of optical tracking elements 128 are measured while the plurality of optical tracking elements 128 are visible to the localizer 22.

As mentioned above, the optical tracking elements 128 (or markers) may be infrared light emitting diodes (IR-LEDs), which emit light in the infrared spectrum in a generally cone shaped beam along a normal line 175. However, the optical tracking elements 128 may be implemented as reflective tracking elements or retroreflectors, which reflect light from an infrared source near the localizer 22 in a direction that is closely aligned with the source.

As previously described, each of the tracking elements 128 has a normal line 175, which is generally orthogonal to the respective tracking face and defines the centerline of peak intensity. Said differently, the orientation of the normal line 175 is representative of a facing direction of the optical tracking element 128. In addition to measuring the relative positions of the plurality of optical tracking elements 128, the navigation system 12 may detect the normal line 175 of the plurality of optical tracking elements 128 while the plurality of optical tracking elements 128 are visible to the localizer 22 for each tracking face. For certain tracker configurations, such as when the tracker includes arrays defining three distinct areas, the step of detecting may be omitted.

Some implementations of the tracker 100 may be configured such that the tracking array has two tracking faces with the optical tracking elements 128 arranged in the same geometrical arrangement. In other words, the optical tracking elements 128 are arranged on one tracking face in the same relative position as the optical tracking elements 128 on the other tracking face. In an illustrative example shown in FIG. 24, the second tracking face TF2 is one tracking face and the third tracking face TF3 is the other tracking face. The distances between, or relative positions of each of the optical tracking elements 128 on the second tracking face TF2 and the third tracking face TF3 are the same. Furthermore, the optical tracking elements 128 on each of those tracking faces defines the same triangular area. However, as can be seen in FIG. 24, the second tracking face TF2 and the third tracking face TF3 are a mirrored arrangement, with the normal lines 175 of the respective optical tracking elements 128 facing away from each other. By determining the normal line 175/direction of facing for each of the visible optical tracking elements 128 or for at least one optical tracking element 128 on each face, the navigation processor can differentiate between the two or more tracking faces.

Once the normal line 175 of the visible optical tracking elements 128 has been detected, the optical tracking elements 128 may be grouped into a first rigid body and a second rigid body based on the measured relative positions and facing directions, each of the first rigid body and the second rigid body including at least one tracking element 128. Based on the measured relative positions and facing directions of the plurality of optical tracking elements 128 of the third tracking face TF3, the plurality of visible optical tracking elements 128 may further be grouped into a third rigid body.

The method further comprises a step of positioning the tracking array such that at least one of the optical tracking elements 128 of the first tracking face TF1, at least one of the optical tracking elements 128 of the second tracking face TF2, or at least one of the optical tracking elements 128 of the third tracking face TF3 is visible to the localizer 22 at the same time. While the at least one optical tracking elements 128 belonging to the respective first tracking face TF1, second tracking face TF2, or third tracking face TF3 are visible at the same time, the relative positions are measured with the localizer 22. In certain configurations, the step of positioning may require that at least three optical tracking elements 128 of the first tracking face TF1 may be visible at the same time that at least one optical tracking element 128 of the second tracking face TF2 or the third tracking face TF3 are visible. Similarly, to establish a correspondence between the second tracking face TF2 and the third tracking face TF3, at least three optical tracking elements 128 of the second tracking face TF2 may need to visible at the same time as at least one optical tracking element 128 of the third tracking face TF3. It should be appreciated that it is not limited to three tracking faces, and the implementation would be useful for trackers having only two faces, or four or more faces.

Using the navigation processor 18, a composite rigid body may be created based on: the first rigid body, the second rigid body, and the third rigid body; and the measured relative positions of at least one optical tracking element 128 of the first tracking face TF1, the at least one optical tracking element 128 of the second tracking face TF2, and the at least one optical tracking element 128 of the third tracking face TF3. Alternatively, the composite rigid body may be created based on only the measured relative positions of the at least one optical tracking element 128 of the first tracking face TF1, the at least one optical tracking element 128 of the second tracking face TF2, and the at least one optical tracking element 128 of the third tracking face TF3.

Using the measured relative positions of the plurality of optical tracking elements 128 of at least three optical tracking elements of a single tracking face, the tracker may be identified. In some implementations, the step of identification may be further based on the detected facing direction data of the plurality of optical tracking elements.

The navigation processor may perform a comparison of the positions of the at least three optical tracking elements of the tracking face and/or the detecting facing direction to the first set of geometrical data to identify the tracking array. The identification may be based on the expected direction of facing of the plurality of optical tracking elements 128 on the first tracking face TF1, the expected direction of facing of the plurality of optical tracking elements 128 on the second tracking face TF2, and/or the expected direction of facing of the plurality of optical tracking elements 128 on the third tracking face TF3. By utilizing the direction of facing, the localizer 22 may be capable of identifying the tracker despite the fact that the visibility of optical tracking elements may be limited to avoid degrading the measurement accuracy at wide angles. This step of identification may trigger the calibration workflow.

As mentioned above, and shown in FIG. 26, in order to facilitate an accurate calibration, the navigation system 12 may display calibration instructions to the user via the display unit 14. These instructions that are displayed may update depending on which calibration step the user is currently performing or has just completed. The instructions may comprise graphics that indicate to the user to rotate the tracking array relative to the localizer 22 such that the at least one optical tracking element 128 of the first tracking face TF1 and the at least one optical tracking element 128 of the second tracking face TF2 are visible to the localizer 22 at the same time. The instructions may further comprise graphics that indicate to the user to rotate the tracking array relative to the localizer 22 such that the at least one optical tracking element 128 of the first tracking face TF1 and the at least one optical tracking element 128 of the third tracking face TF3 are visible to the localizer 22 at the same time. Furthermore, the instructions may then comprise graphics that indicate to the user to rotate the tracking array relative to the localizer 22 such that at least one optical tracking element 128 of the second tracking face TF2 and at least one optical tracking element 128 of the third tracking face TF3 may be visible to the localizer 22 at the same time. The same step could be prompted for the third tracking face TF3 and the first tracking face TF1 described above.

The calibration and registration method may further comprise a step of identifying the medical instrument 34 to which the tracker 100 is coupled. The identification of the medical instrument 34 is based on associating the composite rigid body of the tracker array created by the navigation processor to a medical instrument 34 that may be used in the surgical procedure. The tracking array may further be assigned to a particular medical instrument 34 in the same way by associating the composite rigid body to the medical instrument 34. The method may further comprise determining a positional relationship between a portion of the medical instrument 34 and the composite rigid body by positioning the portion of the medical instrument 34 on a known reference location. The tracker 100 may be calibrated to the medical instrument using various techniques, such as by touching off on a reference location that is being tracked by the localizer 22. In one example, the reference location is a known position on a trackable calibration device.

Figure 27:
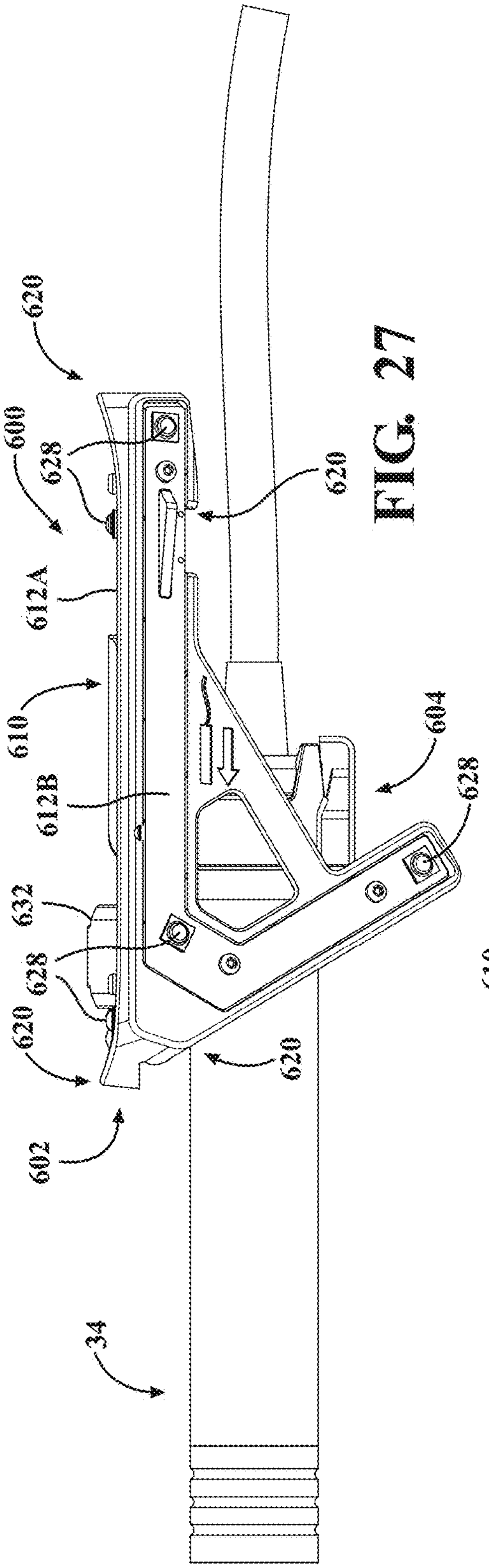
FIG. 27 is a side view of a tracker and an exemplary surgical instrument.
Figure 28:
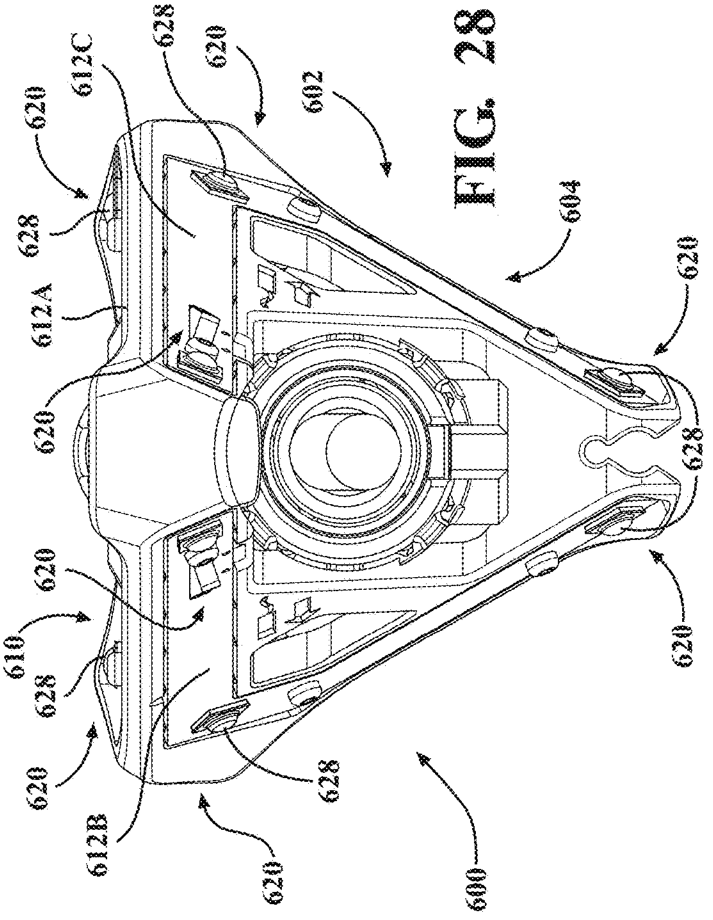
FIG. 28 is a proximal-end view of the tracker and surgical instrument of FIG. 27.

Turning now to FIGS. 27-34, an exemplary optical tracker 600 is shown. Specifically, in FIGS. 27 and 28, the optical tracker 600 is shown coupled to a surgical object, shown here as a handheld surgical instrument 34. The surgical instrument 34 illustrated in connection with FIGS. 27 and 28 is substantially similar to the surgical instrument described above in connection with FIGS. 1-26. As such, the surgical object may be a surgical drill, however other types of instruments are contemplated, such as a handheld saw or bur, an ultrasonic ablation tool, etc. In other implementations of the surgical tracker, the surgical object may be an adapter (not shown) that is engageable with a surgical instrument. For example, the adapter may be used to facilitate coupling the tracker to a surgical instrument (such as a screwdriver) that is rotatable about the longitudinal axis during use, and as such it may be desirable that the adapter permit relative rotation between the tracker and the surgical instrument.

The surgical instrument 34 has a proximal end 36 and a distal end 38 that are spaced along an instrument axis 40. In many cases, such as shown in FIG. 2, the surgical instrument 34 transfers mechanical energy along the instrument axis 40 from a source (e.g. a motor or an ultrasonic transducer) arranged near the proximal end 36 to an attachment 42 coupled to the distal end 38 of the surgical instrument 34. The surgical instrument 34 may include a housing 46, a motor (not shown) disposed in the housing 46, a flexible supply cable 48 protruding from the housing 46 in a proximal region, and an attachment interface 50 near the distal end 38 of the surgical instrument 34.

Turning now to FIGS. 27 and 28, the tracker 600 may comprise a tracker frame 602 comprising a coupling portion 604, which defines an instrument engaging aperture 606 extending therethrough along a longitudinal axis 608 similar to the trackers described above. The tracker frame 602 may further comprise an offset body 610 supported on the coupling portion 604 and extending proximally and generally parallel to the longitudinal axis 608.

Figure 29:
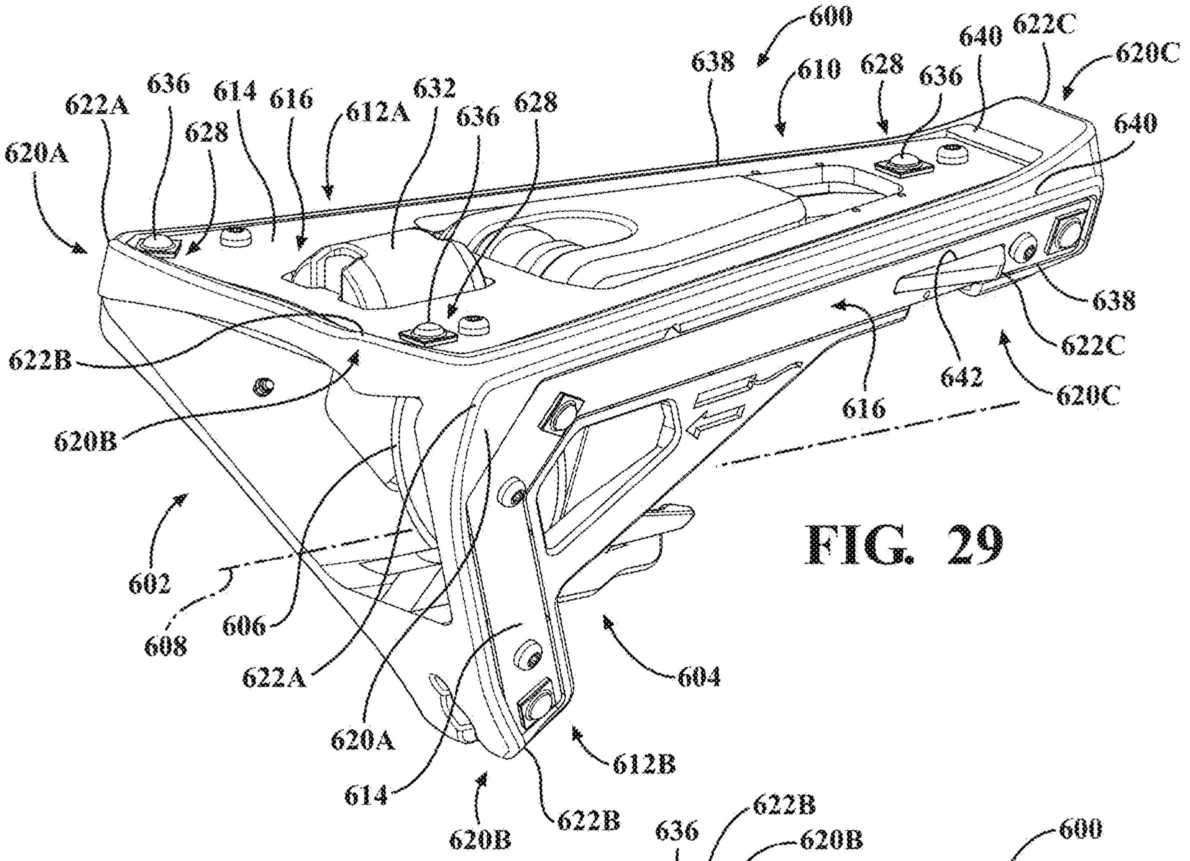
FIG. 29 is a distal-end perspective view of the tracker of FIG. 27 with the surgical instrument removed.
Figure 30:
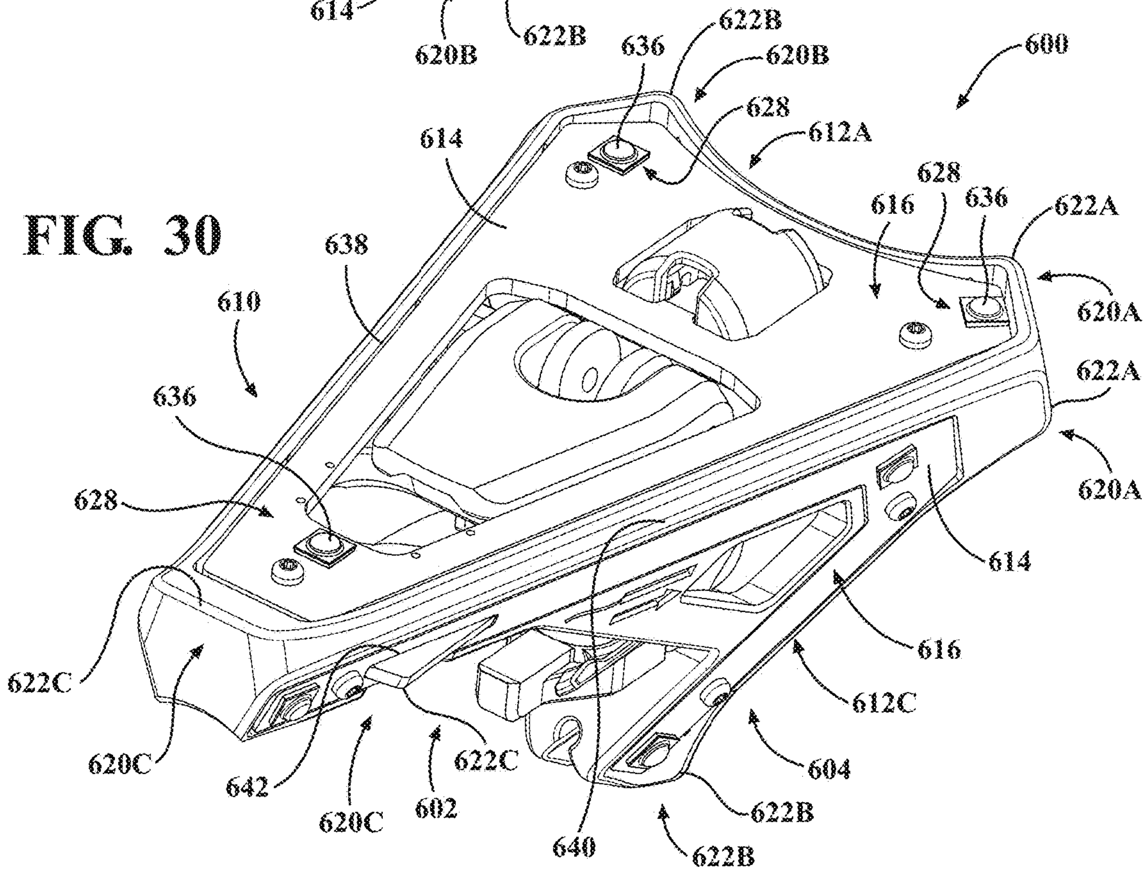
FIG. 30 is a proximal-end perspective view of the tracker of FIG. 29.

With reference to FIGS. 29 and 30, the tracker 600 and tracker frame 602 are shown without the surgical instrument 34. In addition to the offset body 610, the tracker 600 may further comprise one or more pedestals 620 coupled to the tracker frame 602. For example, the one or more pedestals may be three pedestals, a first pedestal 620A, a second pedestal 620B, and a third pedestal 620C, having a pedestal height 624, discussed in further detail below. The pedestals 620 collectively have at least three apex points 622, which in some cases may be associated with a corresponding pedestal 620. For example, the first pedestal 620A may have a first apex point 622A, the second pedestal 620B may have a second apex point 622B, and the third pedestal 620C may have a third apex point 622C. While the tracker 600 illustrated in FIGS. 29 and 30 is illustrated as having three discrete pedestals 620A, 620B, 620C each having a respective apex point 622A, 622B, 622C, it is contemplated that the tracker 600 may comprise a single pedestal having three apex points. Other combinations of pedestals and apex points are further contemplated, such as two pedestals, a first pedestal with two apex points and a second pedestal with one apex point. Additional pedestals and apex points are further contemplated.

Figure 33:
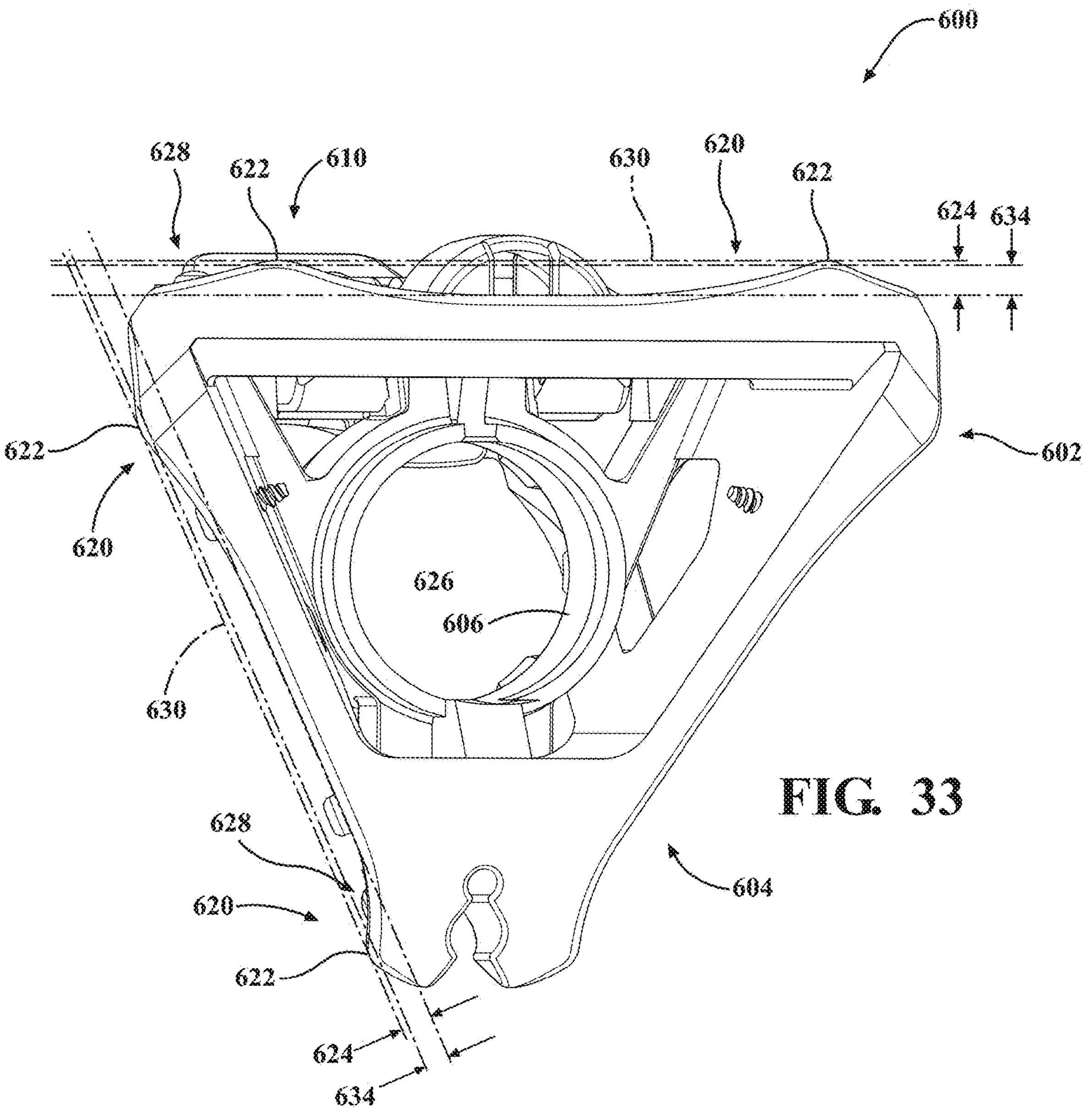
FIG. 33 is another distal-end perspective view of the tracker of FIG. 29 showing planes defined by the LED emitters and by pedestals coupled to a tracker frame.
Figure 34:
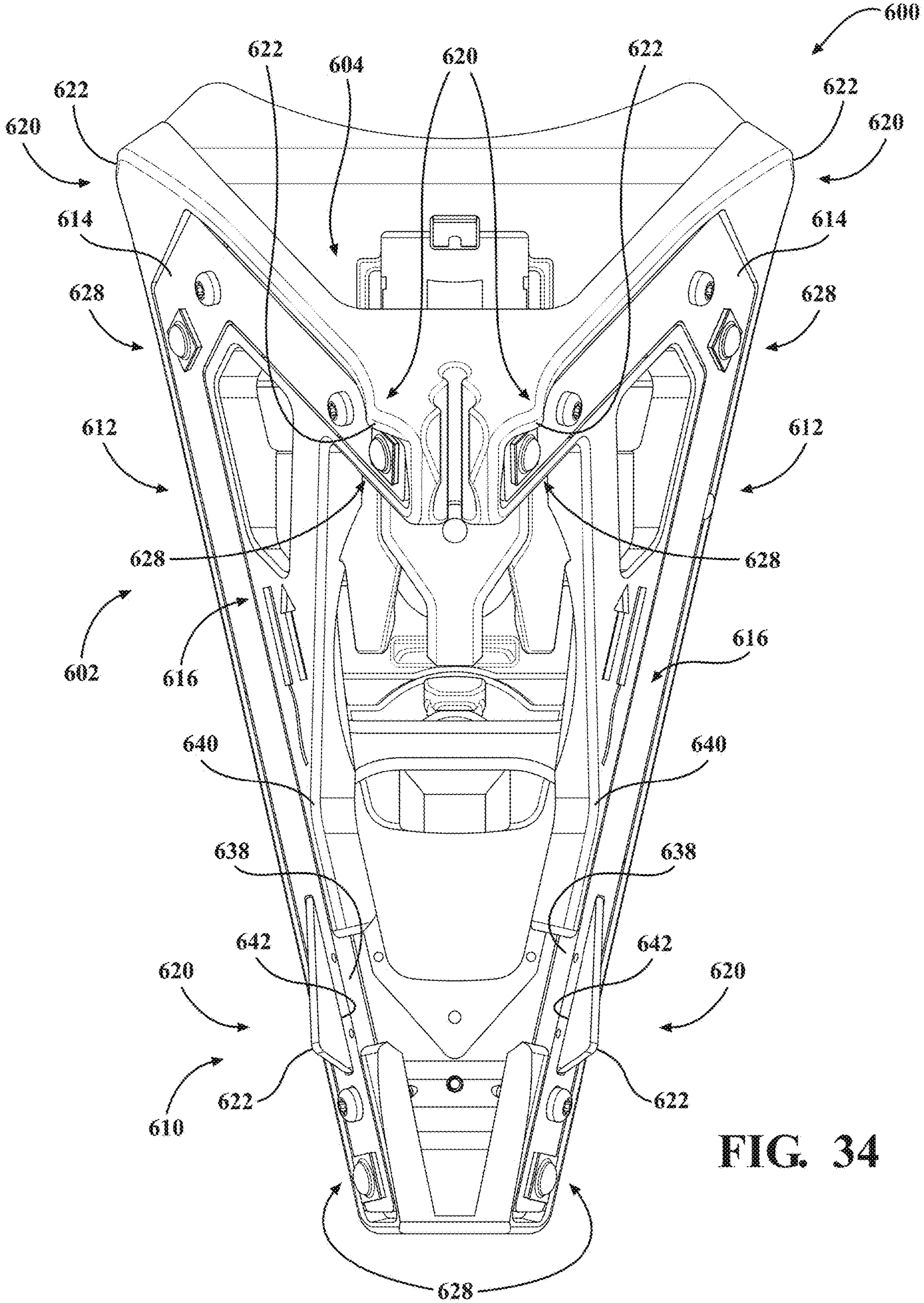
FIG. 34 is a bottom-side view of the tracker of FIG. 29.

The at least three apex points 622 may define a support plane 630 in some instances, which is further defined by three apex points having the greatest pedestal heights 624. Accordingly, the pedestal height may alternatively refer to the height of the support plane 630 from a mounting face 616 (discussed below). The support plane 630 is a representative plane upon which the tracker 600 would be supported if the tracker 600 was placed on a relatively flat surface, such as a table. Referring specifically to FIG. 33, the tracker 600 is shown oriented such that two support planes 630 are visible, each support plane 630 being associated with one side of the tracker frame 602. It should be appreciated that while only two support planes 630 are illustrated, an additional support plane is defined on the side of the tracker frame 602 having the second tracking array 612B.

The optical tracker 600 further has a center of mass 626, which is illustrated in an estimated, non-representative location in FIG. 33. The center of mass 626 is located within a volume of the tracker frame 602 and represents a theoretical location of a point mass of the tracker 600. In order to balance the tracker 600 on the apex points 622 when the tracker 600 is placed on a surface, the mass of the tracker 600 must be distributed among the at least three apex points 622. Accordingly, the apex points 622 and the pedestals 620 are arranged on the tracker frame 602 spaced from the center of mass 626 such that the center of mass 626 is positioned between the at least three apex points 622. Said differently, a gravitational force component acting on the center of mass 626 in a downward direction would be within a triangle defined by the three apex points 622.

Figure 31:
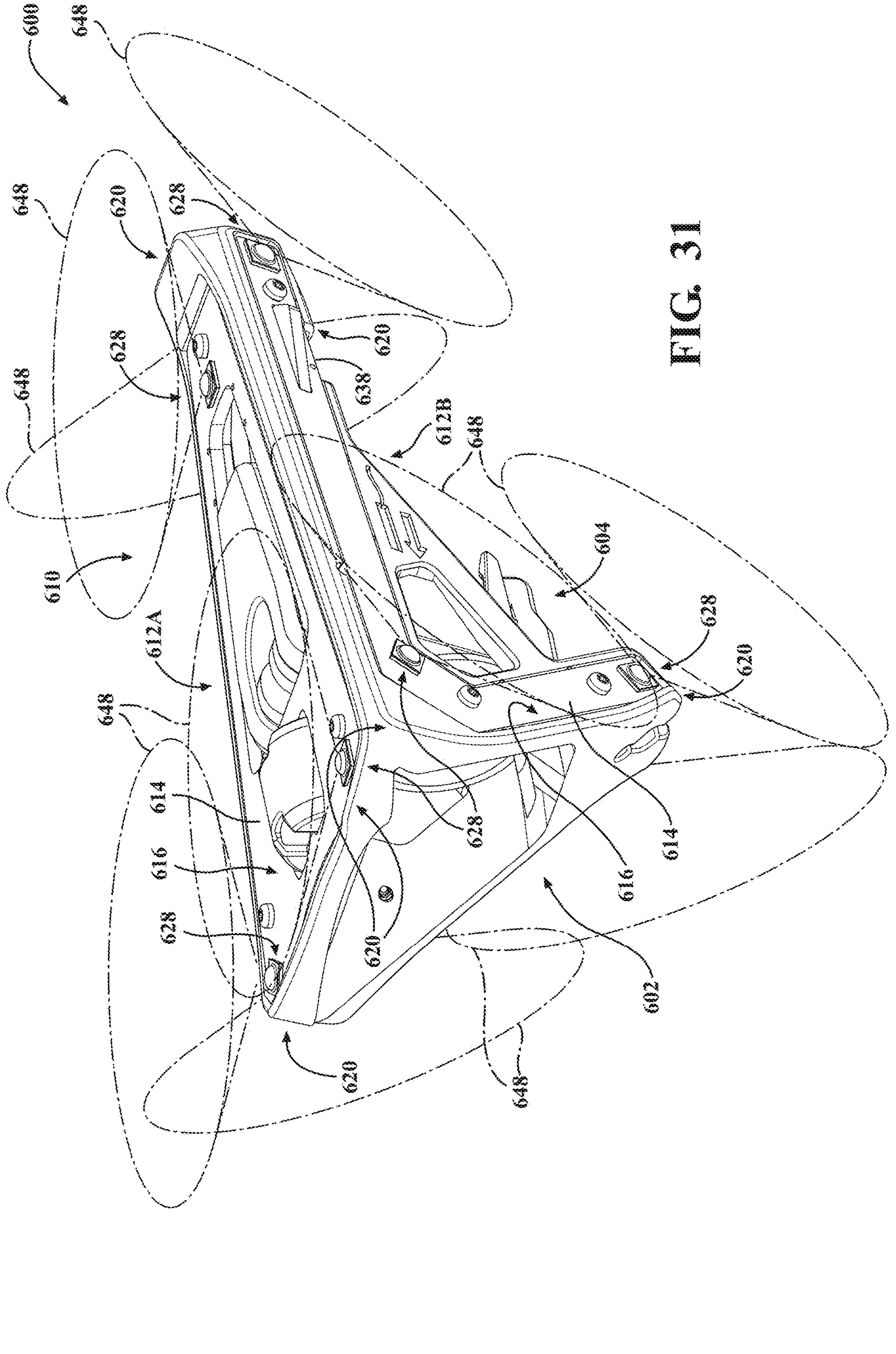
FIG. 31 is another distal-end perspective view of the tracker of FIG. 29 showing a plurality of LED emitters and exemplary illuminated regions.
Figure 32:
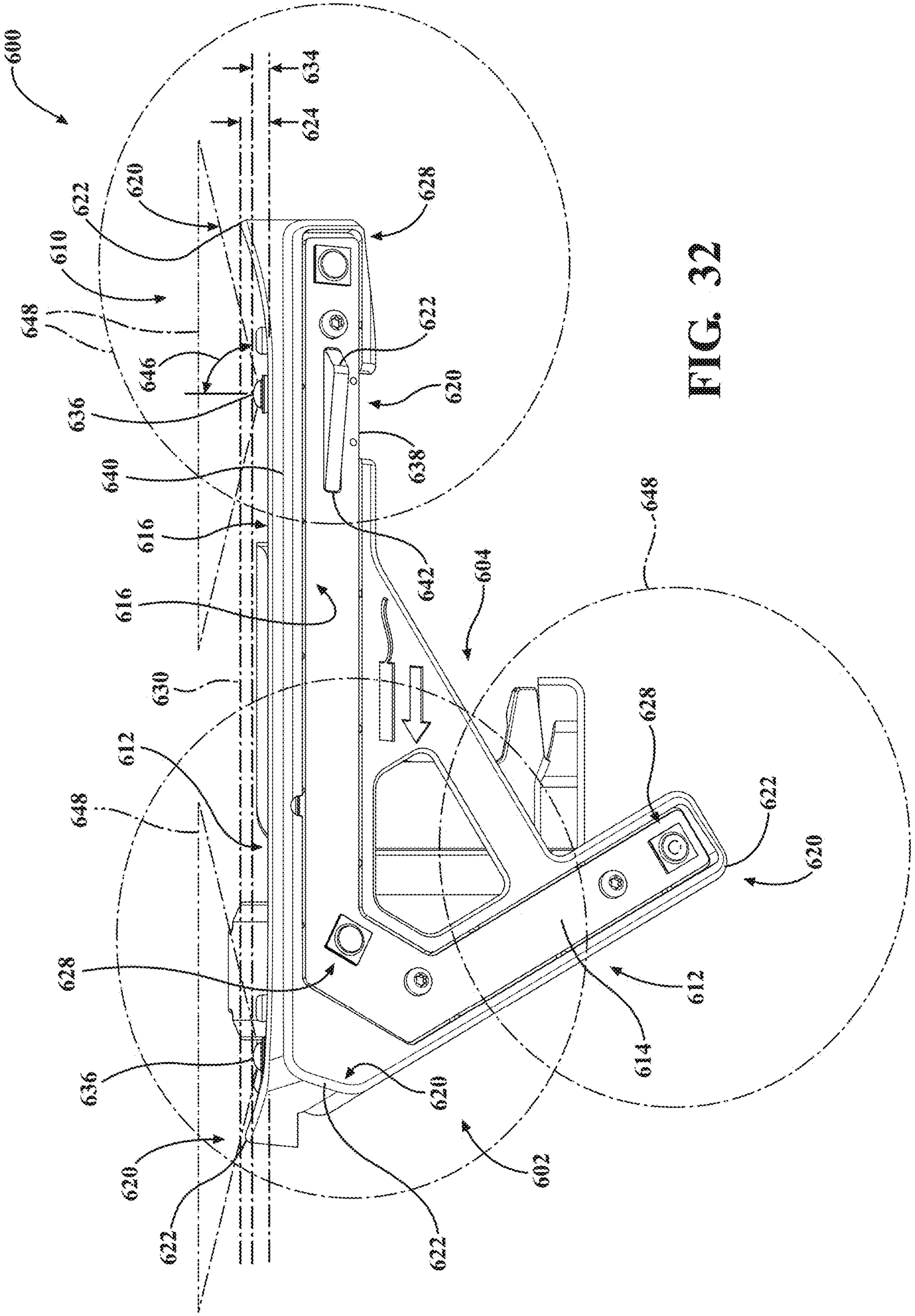
FIG. 32 is a side view of the tracker and exemplary illuminated regions of FIG. 31.

Turning now to FIGS. 31 and 32, in order to track the position and orientation of the surgical object, the tracker 600 may comprise one or more tracking arrays 612 coupled to the tracker frame 602. The tracking array 612 may comprise a mounting fixture 614 having a planar mounting face 616 and a plurality of LED emitters 628 mounted on the mounting face 616. The tracking array 612 as shown here may be configured with a mounting face 616 having a generally triangular shape, however other shapes are considered. While the mounting face 616 is illustrated as being generally planar, it is to be appreciated that the mounting face 616 may have certain protrusions or raised portions that may not be perfectly planar. For example, electrical components may be soldered on to portions of the mounting face 616, and additionally, conductive traces embedded in the mounting fixture 614 may cause certain portions of the mounting face 616 to be raised. The tracking arrays 612 may be removably coupled to the tracker frame 602 to permit replacement or service, such as sterilization. Removably coupling may include coupling with a quick release latch, or may include coupling with fasteners that may be removable with the assistance of an appropriate tool, such as shown here.

Here, the tracker 600 comprises three tracking arrays 612, which are radially arranged about the longitudinal axis 608 of the instrument engaging aperture 606. More specifically, a first tracking array 612A, a second tracking array 612B, and a third tracking array 612C are arranged such that they form a generally tetrahedral shape. As mentioned above, the offset body 610 is supported on the coupling portion 604 and extends proximally therefrom. One face of the tetrahedral shape may be defined by the first tracking array 612A, which is arranged on the offset body 610. Other faces of the tetrahedral shape may be defined by the second tracking array 612B and the third tracking array 612C. The second tracking array 612B and the third tracking array 612C may be coupled to both the offset body 610 and the coupling portion 604. Said differently, a portion of the second tracking array 612B is coupled to one side of the offset body 610 adjacent to the first tracking array 612A and another portion of the second tracking array 612B is coupled to the coupling portion 604. A portion of the third tracking array 612C is coupled to one side of the offset body 610 adjacent to the first tracking array 612A and opposite the second tracking array 612B and another portion of the third tracking array 612C is coupled to the coupling portion 604.

As mentioned above, each tracking array 612 comprises a mounting fixture 614 having a planar mounting face 616. The LED emitters 628 are supported on the mounting face 616 and arranged to form an identifiable shape that can be detected by an optical tracking system to determine the position and orientation of the tracker 600 and therefore the surgical object. The LED emitters 628 emit light, oftentimes in the infrared spectrum, in a continuous and simultaneous manner and are powered by a battery 632 carried by the tracker 600. Power is transferred, at least in part, from the battery 632 to the LED emitters 628 via conductive traces in or on the mounting fixture 614. The mounting fixture 614 may be implemented as a printed circuit board, such as shown here.

The mounting face 616 of each mounting fixture 614 is a generally planar side of the printed circuit board to which the LED emitters 628 and other electronic components may be mounted. In one exemplary implementation, the LED emitters 618 may be soldered to the mounting face 616. It should be appreciated that the LED emitters 618 may be secured, such as by soldering, to a side of the mounting fixture 614 opposite of the mounting face 616, as in the case of through-hole components, for example. Similarly, mounting further comprises attachment via an intermediate component (not shown) such as a heat sink or other thermal management device. When mounted to the mounting face 616 each of the LED emitters 628 extends above the mounting face 616 by a diode height 634. The diode height 634 is the distance between the mounting face 616 and an outermost point 636 of the LED emitter 628. For example, the diode height 634 may be less than 2.5 mm in some implementations. In other implementations, the diode height 634 may be less than 2.0 mm, or less than 1.75 mm.

The mounting fixture 614, and accordingly the tracking array 612, may be coupled to the tracker frame 602 via fasteners, such as shown here, such that the mounting face 616 forms a portion of an exterior surface of the tracker 600. Said differently, the exterior or outermost surface of the tracker 600 may be partially defined by the mounting face 616 of the mounting fixture 614. In some configurations of the tracker (not shown), the mounting fixture may be removably coupled to the tracker frame via a latch. In this way the tracking array may be serviceable separately from the tracker frame such as for cleaning, calibration, or replacement.

Utilizing the mounting fixture 614 to form a part of the exterior surface of the tracker 600 advantageously allows maximum light transmission from the LED emitters 628 i.e. without an additional covering, none of the light emitted by the LED emitters 628 is absorbed, thereby increasing the amount of light that may be visible to the tracking camera. However, the exposed LED emitters 628 may be more susceptible to undesired contact with a foreign object or debris. If the tracker 600 is mishandled, contact with one of the LED emitters may cause the relative position of an individual LED emitter 628 to shift, or otherwise damage the LED emitter 628.

With continued reference to FIGS. 32 and 33, both the pedestal height 624 and the diode height 634 are shown. Here, it can be seen that the pedestal height 624 is greater than the diode height 634, and therefore the support plane 630 is spaced away from the outermost point 636 of each LED emitter 628. In this way, when the tracker 600 is placed on a surface (again, such as a table) the tracker frame 602 contacts the surface at the apex points 622 and is supported on the pedestals 620. Because the pedestals 620 are coupled to the tracker frame 602, none of the weight of the tracker 600 is transferred to the tracking array 612. Furthermore, because the diode height 634 is less than the pedestal height 624, there is no contact between the surface and the LED emitters 628, which reduces the likelihood of damaging the LED emitters 628 when the tracker 600 is placed on a surface. By way of example, in implementations of the tracker 600 employing LED emitters 628 with a diode height 634 of 2.5 mm or less, the pedestal height 624 may be greater than 2.5 mm, such as 3.0 mm. Alternatively, if the tracker 600 employs LED emitters with a diode height 634 of 1.75 mm or less, the pedestal height 624 may be similarly reduced to greater than 1.75 mm, such as 2.0 mm or 2.5 mm.

Some implementations of the tracker 600 may utilize tracking arrays 612 having the apex points coupled to the mounting fixture 614. While apex points that are coupled to the mounting fixture 614 may not prevent the weight of the tracker 600 from being supported by the tracking array 612, the effectiveness in reducing the likelihood of damage to the LED emitters 628 is unaffected. Because the apex points protrude from the mounting face 616 a distance greater than the LED emitters 628, contact between a table surface and the LED emitters 628 is prevented.

Best shown in FIG. 32, on some of the tracking arrays 612 each of the mounting fixtures 614 has a perimeter 638 or outside edge that defines the shape of the mounting fixture 614. For example, the second tracking array 612B and the third tracking array 612C may each have an L or "dog-leg" shaped perimeter 638. This perimeter 638 further defines the mounting face 616. Some implementations of the tracker 600 may arrange one or more of the pedestals 620 within the perimeter 638 of the mounting fixture 614. Said differently, the pedestals 620 may be mounted on the mounting fixture 614 and extend therefrom to the pedestal height 624.

While some pedestals 620 may be arranged within the perimeter 638 of the mounting fixture 614, others may be arranged outside the perimeter 638 on a rim 640 of the tracker frame 602. For example the rim 640 may be a portion of the tracker frame 602 that is adjacent to and around the perimeter 638. The pedestals 620 may be formed on the rim 640 or may protrude from the rim 640. With respect to FIG. 30, the first pedestal 620A, the second pedestal 620B, and the third pedestal 620C may be formed on the rim 640 and outside the perimeter 638. Conversely, in reference to FIG. 31, the first pedestal 620A and the second pedestal 620B may be formed on the rim 640 and the third pedestal 620C may be within the perimeter 638 and separate from the rim 640.

Some implementations of the tracking array 612, such as shown in FIG. 32, may utilize a mounting fixture 614 that defines an opening 642, which extends therethrough. One of the pedestals 620 may be coupled to the tracker frame 602 and positioned within the opening 642 such that the pedestal 620 extends above the mounting face 616 to the pedestal height 624. For example, the third pedestal 620C of FIG. 32 is coupled to the tracker frame 602 behind the tracking array 612B and protrudes through the opening 642 in the mounting fixture 614.

Referring to FIGS. 31 and 32 the arrangement of the LED emitters 628 on each of the tracking arrays 612 is shown. As mentioned above, the LED emitters 628 are mounted on the mounting face 616 of the mounting fixture 614 to emit light, which is used by the tracking system to measure the position of the tracker 600. Distribution of light around the tracker 600 may be enhanced by configuring the LED emitters 628 to emit light in a uniform manner. For example and as shown here, each of the LED emitters 628 may be configured to emit light normal to the mounting face 616. Similar to the emission angle 174 described above, each of the LED emitters 628 also has an emission angle 646 that defines an illuminated region 648. Here, the illuminated region 648 is illustrated as having a cone shape, which is the approximate volume of space that is illuminated by the respective LED emitter 628 during operation. An emission angle 646 of 75 degrees is illustrated, which results in an illuminated region 648 that occupies approximately 150 degrees.

Further to improving the visibility of the tracker 600, maximizing the amount of light that is visible to the tracking system may include reducing any interference in the illuminated region 648. Best shown in FIG. 32 in connection with the tracking array 612A coupled to the offset body 610 the illuminated region 648 for two of the LED emitters 628 is shown along with the support plane 630 and the diode height 634. The illuminated regions 648 are illustrated with dashed lines, which represent a cone of light above a brightness threshold. Because precision of the tracker 600 is increased when the spacing between each LED emitter 628 is greater, arranging the LED emitters 628 near ends of the tracker frame 602 is advantageous. Likewise, increasing the distance between each of the pedestals 620 offers increased stability when placing the tracker 600 on a surface, further reducing the possibility of unintentional damage to the tracking arrays 612.

With the goals of placing both the LED emitters 628 and the pedestals 620 at the ends of the tracker frame 602 in competition for similar space on the tracker frame 602, the efficacy of the pedestals 620 should not reduce the performance of the LED emitters 628. By spacing the pedestals 620 substantially outside of the illuminated region 648, the placement of the pedestals 620 will result in little to no reduction in performance.

Clauses:

I. A method of operating a tracker, wherein the tracker comprises a tracker frame and an electrical circuit supported by the tracker frame, wherein the electrical circuit comprises at least one infrared light emitting diode, IR-LED, wherein the electrical circuit further comprises a battery or a wireless power reception device configured to receive power wirelessly, the method comprising: providing, by the battery or the wireless power reception device, power to operate the at least one IR-LED; and limiting, by the electrical circuit, a current for at least one of the at least one IR-LED to not exceed 15 milliampere (mA).

II. A method of tracking the position and orientation of a tracker coupled to a surgical instrument within a surgical navigation system, the tracker defining a longitudinal axis and comprising at least three arrays each having at least three infrared emitters, said at least three arrays radially arranged about said longitudinal axis, the method comprising: measuring a position of each of the at least three infrared emitters to determine a position and orientation of each array; calculating a correction factor corresponding to the position of at least one marker of each array relative to each other array; determining the relative position and orientation of at least one marker of each array visible to the surgical navigation system; and determining the position and orientation of the tracker by correlating the relative position and orientation of said at least one marker of each array to an absolute position of the tracker using the correction factor.

III. A method for calibrating a tracking array for a surgical procedure using a localizer, the tracking array having a first tracking face and a second tracking face coupled to one another, the first tracking face and the second tracking face collectively including a plurality of optical tracking elements, the method comprising: positioning the tracking array such that the plurality of optical tracking elements of the first tracking face and the second tracking face are visible to the localizer; measuring relative positions of the plurality of optical tracking elements while the plurality of optical tracking elements are visible to the localizer; detecting a facing direction of the plurality of optical tracking elements while the plurality of optical tracking elements are visible to the localizer; grouping the plurality of optical tracking elements into a first rigid body and a second rigid body based on the measured relative positions and facing direction of the plurality of optical tracking elements, each of the first rigid body and the second rigid body including at least one tracking element; positioning the tracking array such that the at least one optical tracking element of the first rigid body and at least one optical tracking element of the second tracking face is visible to the localizer at the same time; measuring relative positions of the at least one optical tracking element of the first tracking face and at least one optical tracking element of the second tracking face while visible to the localizer at the same time; and creating a composite rigid body based on the first rigid body, the second rigid body, and the measured relative positions of at least one optical tracking element of the first tracking face and the at least one optical tracking element of the second tracking face while visible at the same time.

IV. A method for calibrating a tracking array for a surgical procedure using a localizer, the tracking array having a first tracking face and a second tracking face coupled to one another, the first tracking face and the second tracking face collectively including a plurality of optical tracking elements, the method comprising: positioning the tracking array such that the plurality of optical tracking elements of the first tracking face and the second tracking face are visible to the localizer; measuring relative positions of the plurality of optical tracking elements while the plurality of optical tracking elements are visible to the localizer; positioning the tracking array such that the at least one optical tracking element of the first tracking face and at least one optical tracking element of the second tracking face is visible to the localizer at the same time; measuring relative positions of the at least one optical tracking element of the first tracking face and at least one optical tracking element of the second tracking face while visible to the localizer at the same time; and creating a composite rigid body based on the measured relative positions of at least one optical tracking element of the first tracking face and the at least one optical tracking element of the second tracking face while visible at the same time.

V. A disposable optical tracker for tracking a surgical instrument, the optical tracker comprising: a circuit board having a planar configuration; an arrangement of at least three IR-LEDs coupled to said circuit board and disposed in a common plane, the distance between any two IR-LEDs is unique; an electrical circuit configured to limit a current for the at least three IR-LED to not exceed 15 mA; a battery in electrical communication with the at least three IR-LEDs; and wherein the disposable optical tracker does not comprise a communication interface and does not comprise a power cord.

VI. The disposable optical tracker of clause V, wherein the arrangement of at least three IR-LEDs is configured for continuous or quasi-continuous operation.

VII. The disposable optical tracker of clause V, wherein the electrical circuit comprises at least one resistor configured to limit the current for at least one of the at least three IR-LEDs.

VIII. The disposable optical tracker of clause VII, wherein the current for the at least one of the at least three IR-LEDs is limited by an internal electrical resistance of the at least one of the at least three IR-LEDs and an electrical resistance of the at least one resistor electrically connected in series to the at least one of the at least three IR-LEDs.

IX. The disposable optical tracker of clause VII, wherein the electrical circuit is configured to limit a radiant intensity of at least one of the at least three IR-LEDs to not exceed 40 microwatts per steradian (μW/sr).

X. The disposable optical tracker of clause VII, wherein a distance between two of the at least three IR-LEDs is smaller than 70 mm.

XI. The disposable optical tracker of clause VII, wherein the electrical circuit is configured to operate the at least three IR-LEDs simultaneously.

XII. The disposable optical tracker of clause VII, wherein a mass of the disposable optical tracker does not exceed 40 g.

XIII. The disposable optical tracker of clause V, further comprising a battery receptacle configured to engage said battery, and wherein said battery is further defined as a coin-cell battery.

XIV. The disposable optical tracker of clause V, further comprising a single-use switch in electrical communication with the at least three IR-LEDs.

XV. A surgical navigation system comprising the tracker of clause V and a camera capable of detecting light of at least one IR-LED and of generating a camera signal indicative of the detected light.

XVI. A tracker for a handheld surgical instrument having an instrument axis, the tracker comprising: a tracker frame comprising a mounting body defining an instrument engaging aperture having a longitudinal axis and comprising an attachment protrusion protruding parallel to said longitudinal axis and engageable with the surgical instrument for rotationally constraining said tracker frame along the instrument axis, and wherein said instrument engaging aperture is bisected by a plane parallel to said longitudinal axis to define first and second regions; and a plurality of LED emitters coupled to said tracker frame and arranged about said longitudinal axis such that a first quantity of said plurality of LED emitters are positioned in said first region and a second quantity of said plurality of LED emitters are positioned in said second region, said first quantity greater than said second quantity for decreasing obstruction of the surgical instrument.

XVII. The tracker of clause XVI, wherein said tracker frame further comprises an offset body supported on said mounting body and positioned in said first region, said offset body protruding proximally from a distal end coupled to said mounting body to a proximal end.

XVIII. The tracker of clause XVII, wherein said proximal end of said offset body is spaced from said distal end at a distance greater than said offset body is spaced from said longitudinal axis.

XIX. The tracker of clause XVII, wherein said offset body is tapered from said distal end to said proximal end.

XX. The tracker of clause XVI, wherein said plurality of LED emitters emit light continuously.

XXI. The tracker of clause XVI, wherein said plurality of LED emitters are arranged to form at least two arrays, each array comprising at least three LED emitters.

XXII. The tracker of clause XXI, wherein each of said at least two arrays comprises a circuit board, and wherein said at least three of said plurality of LED emitters are attached to said circuit board, and wherein said circuit boards are non-parallel relative to one another.

XXIII. The tracker of clause XXI, wherein said at least two arrays are radially arranged about said longitudinal axis such that said LED emitters radially emit infrared light 360 degrees about said longitudinal axis.

XXIV. The tracker of clause XXI, wherein at least a portion of said at least two arrays is arranged on said offset body and positioned proximally of said mounting body.

XXV. The tracker of clause XVI, wherein said tracker frame comprises a polymer or titanium.

XXVI. The tracker of clause XVI, wherein a coupling channel is defined in said mounting body, said mounting body further comprising two resilient arms disposed in said coupling channel, each resilient arm having a reference end and a movable end, said resilient arms cooperating to define said instrument engaging aperture.

XXVII. The tracker of clause XVI, further comprising a single use switch coupled to said tracker frame and in electrical communication with said plurality of LED emitters, said single use switch comprising a removable isolating material.

XXVIII. The tracker of clause XVI, wherein three radial segments of equal proportion are defined about said longitudinal axis to collectively encircle said longitudinal axis, and wherein said plurality of LED emitters is further defined as at least six LED emitters, said at least six LED emitters positioned such that at least one of said at least six LED emitters is positioned within each radial segment.

XXIX. A handheld surgical instrument having an instrument axis and coupled to the tracker of clause XVI.

XXX. A tracker for a handheld surgical instrument having a proximal end spaced along an instrument axis from a distal end, the tracker comprising: a tracker frame formed from a polymer and defining an instrument engaging aperture, said instrument engaging aperture defining a longitudinal axis and configured to slidably engage the surgical instrument such that said longitudinal axis of said instrument engaging aperture is aligned with the instrument axis, wherein said tracker frame is rotationally fixed to the surgical instrument; and a plurality of infrared emitters in electrical communication with a power source and coupled to said tracker frame, wherein a radiant intensity of each of said infrared emitters is less than 40 microwatts per steradian (μ W/sr).

XXXI. A tracker for a handheld surgical instrument, the tracker comprising: a tracker frame comprising a mounting body defining an instrument engaging aperture, said instrument engaging aperture defining a longitudinal axis, said tracker frame configured to slidably engage the surgical instrument such that said longitudinal axis of said instrument engaging aperture is aligned with the instrument axis; and at least four infrared emitters each coupled to said tracker frame, wherein said at least four infrared emitters are arranged to form a 3D volume, and wherein said 3D volume is a tetrahedron.

XXXII. An optical tracker for a handheld surgical instrument having an instrument axis, the optical tracker comprising: a tracker frame comprising a mounting body defining an instrument engaging aperture, said instrument engaging aperture defining a longitudinal axis, said tracker frame configured to slidably engage the surgical instrument such that said longitudinal axis of said instrument engaging aperture is aligned with the instrument axis; a plurality of optical markers coupled to said tracker frame; the optical tracker defining a first array comprising at least three of said plurality of optical markers, wherein said at least three optical markers define a first area; the optical tracker further defining a second array comprising at least three of said plurality of optical markers, wherein said at least three optical markers define a second area; the optical tracker further defining a third array comprising at least three of said plurality of optical markers, wherein said at least three optical markers define a third area, wherein said third area is equal to said second area; and wherein said first array, said second array, and said third array are arranged to define a tetrahedral-like shape having one edge and one face that intersect with said longitudinal axis such that a vertex of said tetrahedral-like shape is spaced from said longitudinal axis.

XXXIII. The optical tracker of clause XXXII, wherein said at least three optical markers of said first array are different from said at least three optical markers of said second array.

XXXIV. The optical tracker of clause XXXIII, wherein said at least three optical markers of said first array are different from said at least three optical markers of said third array.

XXXV. The optical tracker of clause XXXIV, wherein said at least three optical markers of said second array are different from said at least three optical markers of said third array.

XXXVI. A tracked handheld surgical instrument having a body extending between proximal and distal ends along an instrument axis and a flexible supply cable coupled to the body and protruding from the proximal end and configured to curve away from the handheld surgical instrument at a distance equal to a bend radius of the flexible supply cable, the tracked handheld surgical instrument comprising: a tracker frame comprising a mounting body defining an instrument engaging aperture, said instrument engaging aperture defining a longitudinal axis, said tracker frame configured to slidably engage the body of the handheld surgical instrument at the proximal end such that said longitudinal axis of said instrument engaging aperture is aligned with the instrument axis, wherein three radial segments of equal proportion are defined about said longitudinal axis to collectively encircle said longitudinal axis, and wherein a proximal end of said tracker frame is spaced proximally of the proximal end of the handheld surgical instrument and positioned relative to the flexible supply cable such that the proximal end of said tracker frame minimizes contact with the flexible supply cable; and at least six optical markers coupled to said tracker frame and positioned such that at least one of said at least six optical markers is positioned within each radial segment, and at least two of said at least six optical markers are positioned proximally of the proximal end of the handheld surgical instrument.

XXXVII. The tracked handheld surgical instrument of clause XXXVI, wherein said proximal end of said tracker frame is positioned in only one of said three radial segments.

XXXVIII. The tracked handheld surgical instrument of clause XXXVI, wherein said tracker frame further comprises an offset body supported on said mounting body and extending in a direction parallel to said longitudinal axis to said proximal end of said tracker frame.

XXXIX. The tracked handheld surgical instrument of clause XXXVIII, wherein the proximal end of the handheld surgical instrument is positioned proximally of a proximal end of said mounting body.

XL. The tracked handheld surgical instrument of clause XXXVI, wherein said tracker frame further comprises an attachment protrusion coupled to said mounting body and radially arranged about said longitudinal axis, wherein said attachment protrusion is configured for indexing engagement in a single position with the surgical instrument along the instrument axis.

XLI. An optical tracker for a surgical instrument, the optical tracker comprising: a tracker frame comprising a mounting body defining an instrument engaging aperture, said instrument engaging aperture defining a longitudinal axis, said tracker frame configured to couple to the surgical instrument with said longitudinal axis aligned with the instrument axis; at least nine optical markers coupled to said tracker frame and arranged to form at least three arrays, wherein each array comprises at least three of said at least nine optical markers, and wherein said at least three optical markers of each array are configured to emit light in the same direction; a single-use switch and a battery in electrical communication with said at least nine optical markers; and wherein each of said at least three arrays is oriented to emit light in a direction different from each other.

XLII. The optical tracker of clause XLI, wherein said at least three arrays emit light at least 260 degrees about said longitudinal axis.

XLIII. The optical tracker of clause XLI, wherein said single-use switch comprises a removable isolating material.

XLIV. A method for calibrating a tracking array for a surgical procedure using a localizer, the tracking array having a first tracking face and a second tracking face coupled to one another, the first tracking face and the second tracking face collectively including a plurality of optical tracking elements, the method comprising: positioning the tracking array such that the plurality of optical tracking elements of the first tracking face and the second tracking face are visible to the localizer; measuring relative positions of the plurality of optical tracking elements while the plurality of optical tracking elements are visible to the localizer; detecting a facing direction of the plurality of optical tracking elements while the plurality of optical tracking elements are visible to the localizer; grouping the plurality of optical tracking elements into a first rigid body and a second rigid body based on the measured relative positions and facing direction of the plurality of optical tracking elements, each of the first rigid body and the second rigid body including at least one tracking element; positioning the tracking array such that the at least one optical tracking element of the first tracking face and at least one optical tracking element of the second tracking face is visible to the localizer at the same time; measuring relative positions of the at least one optical tracking element of the first tracking face and at least one optical tracking element of the second tracking face while visible to the localizer at the same time; and creating a composite rigid body based on the first rigid body, the second rigid body, and the measured relative positions of at least one optical tracking element of the first tracking face and the at least one optical tracking element of the second tracking face while visible at the same time.

XLV. The method of clause XLIV, further comprising storing manufacturing dimensions of the tracking array in a memory device of a navigation system, the manufacturing dimensions including a first set of geometrical data including first tracking face geometrical data and second tracking face geometrical data; and identifying the tracking array based on the first set of geometrical data, the measured relative positions of the plurality of optical tracking elements, and the detected facing direction of the plurality of optical tracking elements.

XLVI. The method of clause XLV, wherein the first tracking face geometrical data includes data indicative of expected relative positions of the plurality of optical tracking elements on the first tracking face and an expected direction of facing of the plurality of optical tracking elements on the first tracking face, and wherein the second tracking face geometrical data includes data indicative of the expected relative positions of the plurality of optical tracking elements on the second tracking face and an expected direction of facing of the plurality of optical tracking elements on the second tracking face.

XLVII. The method of clause XLVI, wherein the step of identifying includes comparing the detected direction of facing of the plurality of optical tracking elements, the expected direction of facing of the plurality of optical tracking elements on the first tracking face, and the expected direction of facing of the plurality of optical tracking elements on the second tracking face.

XLVIII. The method of clause XLV, further comprising displaying calibration instructions based on the step of identifying the tracking array.

XLIX. The method of clause XLVIII, wherein the step of displaying calibration instructions further comprises displaying graphics that indicate to a user to rotate the tracking array relative to the localizer such that the at least one optical tracking element of the first tracking face and at least one optical tracking element of the second tracking face are visible to the localizer at the same time.

L. The method of clause XLIV, further comprising assigning the tracking array to a medical instrument by associating the composite rigid body to the medical instrument.

LI. The method of clause L, further comprising identifying the medical instrument based on associating the composite rigid body to the medical instrument.

LII. The method of clause XLIV, wherein the first tracking face and the second tracking face are mirror images of one another.

LIII. The method of clause XLIV, wherein the tracking array further includes a third tracking face, the first tracking face, the second tracking face, and the third tracking face collectively including the plurality of optical tracking elements; said method further comprising: positioning the tracking array such that the plurality of optical tracking elements of the third tracking face are visible to the localizer; grouping the plurality of optical tracking elements into a third rigid body based on the measured relative positions and facing direction of the plurality of optical tracking elements, measuring relative positions of the at least one optical tracking element of the first tracking face or at least one optical tracking element of the second tracking face, and at least one optical tracking element of the third tracking face while visible to the localizer; and measuring relative positions of the at least one optical tracking element of the first tracking face or at least one optical tracking element of the second tracking face, and at least one optical tracking element of the third tracking face while visible to the localizer; and creating a composite rigid body based on the first rigid body, the second rigid body, and the third rigid body and the measured relative positions of at least one optical tracking element of the first tracking face, the at least one optical tracking element of the second tracking face, and the at least one optical tracking element of the third tracking face.

LIV. The method of clause XLIV, wherein the optical tracking element is a reflective element.

LV. The method of clause XLIV, wherein the optical tracking element is an infrared light emitting diode.

LVI. The method of clause XLIV, further comprising determining a positional relationship between a portion of a medical instrument and the composite rigid body by positioning the portion of the medical instrument on a known reference location.

LVII. The method of clause LVI, wherein the reference location is a known position on a trackable calibration device.

LVIII. The method of clause XLIV, further comprising coupling the tracking array to a medical instrument or a patient.

LIX. A system for navigation of a medical instrument, the system comprising: a localizer; a tracking array having a first tracking face and a second tracking face coupled to one another, the first tracking face and the second tracking face collectively including a plurality of optical tracking elements; a processor configured to: measure relative positions of the plurality of optical tracking elements while the plurality of optical tracking elements are visible to the localizer; detect a facing direction of the plurality of optical tracking elements while the plurality of optical tracking elements are visible to the localizer; group the plurality of optical tracking elements into a first rigid body and a second rigid body based on the measured relative positions and facing direction of the plurality of optical tracking elements, each of the first rigid body and the second rigid body including at least one tracking element; measure relative positions of the at least one optical tracking element of the first tracking face and at least one optical tracking element of the second tracking face while visible to the localizer at the same time; and create a composite rigid body based on the first rigid body, the second rigid body, and the measured relative positions of at least one optical tracking element of the first tracking face and the at least one optical tracking element of the second tracking face while visible at the same time.

LX. A method for calibrating a tracking array for a surgical procedure using a localizer, the tracking array having a first tracking face and a second tracking face coupled to one another, the first tracking face and the second tracking face collectively including a plurality of optical tracking elements, the method comprising: positioning the tracking array such that the plurality of optical tracking elements of the first tracking face and the second tracking face are visible to the localizer; measuring relative positions of the plurality of optical tracking elements while the plurality of optical tracking elements are visible to the localizer; positioning the tracking array such that the at least one optical tracking element of the first tracking face and at least one optical tracking element of the second tracking face is visible to the localizer at the same time; measuring relative positions of the at least one optical tracking element of the first tracking face and at least one optical tracking element of the second tracking face while visible to the localizer at the same time; and creating a composite rigid body based on the measured relative positions of at least one optical tracking element of the first tracking face and the at least one optical tracking element of the second tracking face while visible at the same time.

LXI. An optical tracker for a surgical instrument, the optical tracker comprising: a tracker frame comprising a mounting body configured to couple to the surgical instrument, the tracker frame consisting of a polymer; at least six optical markers coupled to said tracker frame and arranged to form at least two arrays, wherein each array comprises at least three of said at least six optical markers, and wherein said at least three optical markers of each array are configured to emit light in the same direction; a battery in electrical communication with said at least six optical markers; and wherein each of said at least three arrays is oriented to emit light in a direction different from each other.

LXII. An optical tracker for a surgical instrument, the optical tracker comprising: a tracker frame comprising a mounting body defining an instrument engaging aperture, said instrument engaging aperture defining a longitudinal axis, said tracker frame configured to couple to the surgical instrument with said longitudinal axis aligned with the instrument axis; at least nine optical markers coupled to said tracker frame and arranged to form at least three arrays, wherein each array comprises at least three of said at least nine optical markers, and wherein said at least three optical markers of each array are configured to emit light in the same direction; wherein each of said at least three arrays is oriented to emit light in a direction different from each other; and wherein two of said at least three arrays are configured such that a position of said at least three optical markers is mirrored about said longitudinal axis.

LXIII. An optical tracker for a surgical instrument, the optical tracker comprising: a tracker frame comprising a first portion defining an instrument engaging portion and a second portion, and further comprising a polymer; a first circuit board coupled to the first portion of the tracker frame and including at least three LEDs defining a first array; second circuit board coupled to the second portion of the tracker frame and including at least three LEDs defining a second array; wherein said first array is oriented to emit light in a different direction than said second array; a battery electrically coupled to said first circuit board and said second circuit board; and wherein the optical tracker is free from a communication interface.

LXIV. The optical tracker of clause LXIII, wherein said battery is a coin-cell battery.

LXV. The optical tracker of clause LXIII, wherein said battery has a mass less than 5 grams.

LXVI. An optical tracker for a surgical object, the optical tracker comprising: a tracker frame comprising a coupling portion configured to engage the surgical object; a tracking array coupled to said tracker frame comprising: a mounting fixture having a mounting face; a plurality of LED emitters mounted on said mounting face, wherein said plurality of LED emitters extend a first height above said mounting face; and at least three apex points defined by said tracker frame and extending to a second height above said mounting face, wherein said second height is greater than said first height.

LXVII. The optical tracker of clause LXVI, wherein said plurality of LED emitters are configured to emit light normal to said mounting face.

LXVIII. The optical tracker of clause LXVII, wherein each of said plurality of LED emitters has an emission angle that defines an illuminated region, and wherein said at least three apex points are spaced from said LED emitters such that said at least three apex points are substantially outside said illuminated region.

LXIX. The optical tracker of clause LXVIII, wherein said emission angle of each said plurality of LED emitters is at least 75 degrees.

LXX. The optical tracker of clause LXVI, wherein said plurality of LED emitters emit light in a continuous and simultaneous manner.

LXXI. The optical tracker of clause LXVI, wherein each of said plurality of LED emitters has an outermost point, and wherein three of said at least three apex points define a support plane, and wherein said support plane is spaced further from said mounting face than said outermost point of each of said plurality of LED emitters.

LXXII. The optical tracker of clause LXXI, wherein a height of said outermost point of said plurality of LED emitters is less than 2.0 mm.

LXXIII. The optical tracker of clause LXVI, wherein a center of mass of the optical tracker is positioned between said at least three apex points such that the optical tracker may be balanced on the at least three apex points when placed on a surface, and wherein said at least three apex points prevent contact between said plurality of LED emitters and the surface.

LXXIV. The optical tracker of clause LXVI, further comprising one or more pedestals coupled to said tracker frame, wherein one of said at least three apex points is defined by said one or more pedestals.

LXXV. The optical tracker of clause LXXIV, wherein said mounting fixture has a perimeter defining the tracking array and wherein one or more of said one or more pedestals is positioned inside said perimeter.

LXXVI. The optical tracker of clause LXXV, wherein said mounting fixture defines an opening within said perimeter, and wherein one of said one or more pedestals is positioned in said opening.

LXXVII. The optical tracker of clause LXXVI, wherein said one or more pedestals is further defined as three pedestals, and wherein each of said three pedestals has one of said at least three apex points.

LXXVIII. The optical tracker of clause LXVI, wherein said coupling portion defines an instrument engaging aperture extending along a longitudinal axis, wherein said instrument engaging aperture is configured to receive the surgical object such that said longitudinal axis of said instrument engaging aperture is aligned with a longitudinal axis of the surgical object, and wherein said tracking array is further defined as a plurality of tracking arrays, said plurality of tracking arrays radially arranged about said longitudinal axis of said instrument engaging aperture.

LXXIX. The optical tracker of clause LXXVIII, wherein said plurality of tracking arrays is further defined as a first tracking array, a second tracking array, and a third tracking array, and wherein said first tracking array, said second tracking array, and said third tracking array are arranged around said longitudinal axis in a tetrahedral shape.

LXXX. The optical tracker of clause LXVI, wherein an exterior surface of the optical tracker is partially defined by said mounting face of said mounting fixture, and wherein said LED emitters are mounted directly to said mounting face.

LXXXI. The optical tracker of clause LXXX, wherein said mounting fixture comprises a printed circuit board.

LXXXII. The optical tracker of clause LXVI, wherein said tracker frame further comprises an offset body supported on said coupling portion and extending in a proximal direction, wherein said tracking array is coupled to said offset body.

LXXXIII. The optical tracker of clause LXXXII, wherein said tracking array is further defined as a first tracking array, and further comprising a second tracking array and a third tracking array, wherein said second tracking array and said third tracking array are coupled to said coupling portion and to said offset body.

LXXXIV. The optical tracker of clause LXVI, wherein said plurality of LED emitters is further defined as three LED emitters.

Several examples have been discussed in the foregoing description. However, the examples discussed herein are not intended to be exhaustive or limit the invention to any particular form. The terminology that has been used is intended to be in the nature of words of description rather than of limitation. Many modifications and variations are possible in light of the above teachings and the invention may be practiced otherwise than as specifically described.

What is claimed is:

1. A navigation system for navigating a medical instrument, the system comprising:

a localizer;

a tracking array having a first tracking face and a second tracking face coupled to one another, the first tracking face and the second tracking face collectively including a plurality of optical tracking elements;

a processor configured to:

determine that the plurality of optical tracking elements of the first tracking face and the second tracking face are visible to the localizer;

measure relative positions of the plurality of optical tracking elements while the plurality of optical tracking elements are visible to the localizer;

determine that the at least one optical tracking element of the first tracking face and at least one optical tracking element of the second tracking face is visible to the localizer at the same time;

measure relative positions of the at least one optical tracking element of the first tracking face and at least one optical tracking element of the second tracking face while visible to the localizer at the same time; and create a composite rigid body based on the measured relative positions of at least one optical tracking element of the first tracking face and the at least one optical tracking element of the second tracking face while visible at the same time.

2. The system of claim 1, wherein the processor is further configured to:

detect a facing direction of the plurality of optical tracking elements while the plurality of optical tracking elements are visible to the localizer;

group the plurality of optical tracking elements into a first rigid body and a second rigid body based on the measured relative positions and facing direction of the plurality of optical tracking elements, each of the first rigid body and the second rigid body including at least one tracking element; and create the composite rigid body based on the first rigid body, the second rigid body, and the measured relative positions of at least one optical tracking element of the first tracking face and the at least one optical tracking element of the second tracking face while visible at the same time.

3. The system of claim 1, wherein the processor is further configured to:

store manufacturing dimensions of the tracking array in a memory device of the navigation system, the manufacturing dimensions including a first set of geometrical data including first tracking face geometrical data and second tracking face geometrical data;

detect a facing direction of the plurality of optical tracking elements while the plurality of optical tracking elements are visible to the localizer; and identify the tracking array based on the first set of geometrical data, the measured relative positions of the plurality of optical tracking elements, and the detected facing direction of the plurality of optical tracking elements.

4. The system of claim 3, wherein:

the first tracking face geometrical data includes data indicative of expected relative positions of the plurality of optical tracking elements on the first tracking face and an expected direction of facing of the plurality of optical tracking elements on the first tracking face, and the second tracking face geometrical data includes data indicative of the expected relative positions of the plurality of optical tracking elements on the second tracking face and an expected direction of facing of the plurality of optical tracking elements on the second tracking face.

5. The system of claim 3, wherein the processor is further configured to cause a display to display calibration instructions based on the step of identifying the tracking array.

6. The system of claim 5, wherein causing the display to display calibration instructions comprises causing the display to display graphics that indicate to a user to rotate the tracking array relative to the localizer such that the at least one optical tracking element of the first tracking face and at least one optical tracking element of the second tracking face are visible to the localizer at the same time.

7. The system of claim 4, wherein identifying the tracking array comprises comparing the detected direction of facing of the plurality of optical tracking elements, the expected direction of facing of the plurality of optical tracking elements on the first tracking face, and the expected direction of facing of the plurality of optical tracking elements on the second tracking face.

8. The system of claim 1, wherein the processor is further configured to assign the tracking array to the medical instrument by associating the composite rigid body to the medical instrument.

9. The system of claim 8, wherein the processor is further configured to identify the medical instrument based on associating the composite rigid body to the medical instrument.

10. The system of claim 1, wherein:

the tracking array further includes a third tracking face;

the first tracking face, the second tracking face, and the third tracking face collectively including the plurality of optical tracking elements; and the processor is further configured to:

detect a facing direction of the plurality of optical tracking elements while the plurality of optical tracking elements are visible to the localizer;

measure relative positions of the plurality of optical tracking elements while the plurality of optical tracking elements are visible to the localizer;

group the plurality of optical tracking elements into a first rigid body, a second rigid body, and a third rigid body based on the measured relative positions and facing direction of the plurality of optical tracking elements, each of the first rigid body, the second rigid body, and the third rigid body including at least one tracking element;

measure relative positions of the at least one optical tracking element of the first tracking face or at least one optical tracking element of the second tracking face, and at least one optical tracking element of the third tracking face while visible to the localizer; and create the composite rigid body based on the first rigid body, the second rigid body, and the third rigid body and the measured relative positions of at least one optical tracking element of the first tracking face, the at least one optical tracking element of the second tracking face, and the at least one optical tracking element of the third tracking face.

11. A method for calibrating a tracking array for a surgical procedure using a localizer, the tracking array having a first tracking face and a second tracking face coupled to one another, the first tracking face and the second tracking face collectively including a plurality of optical tracking elements, the method comprising:

positioning the tracking array such that the plurality of optical tracking elements of the first tracking face and the second tracking face are visible to the localizer;

measuring relative positions of the plurality of optical tracking elements while the plurality of optical tracking elements are visible to the localizer;

positioning the tracking array such that the at least one optical tracking element of the first tracking face and at least one optical tracking element of the second tracking face is visible to the localizer at the same time;

measuring relative positions of the at least one optical tracking element of the first tracking face and at least one optical tracking element of the second tracking face while visible to the localizer at the same time; and creating a composite rigid body based on the measured relative positions of at least one optical tracking element of the first tracking face and the at least one optical tracking element of the second tracking face while visible at the same time.

12. The method of claim 11, further comprising:

detecting a facing direction of the plurality of optical tracking elements while the plurality of optical tracking elements are visible to the localizer;

grouping the plurality of optical tracking elements into a first rigid body and a second rigid body based on the measured relative positions and facing direction of the plurality of optical tracking elements, each of the first rigid body and the second rigid body including at least one tracking element; and creating the composite rigid body based on the first rigid body, the second rigid body, and the measured relative positions of at least one optical tracking element of the first tracking face and the at least one optical tracking element of the second tracking face while visible at the same time.

13. The method of claim 11, further comprising:

storing manufacturing dimensions of the tracking array in a memory device of a navigation system, the manufacturing dimensions including a first set of geometrical data including first tracking face geometrical data and second tracking face geometrical data;

detecting a facing direction of the plurality of optical tracking elements while the plurality of optical tracking elements are visible to the localizer; and identifying the tracking array based on the first set of geometrical data, the measured relative positions of the plurality of optical tracking elements, and the detected facing direction of the plurality of optical tracking elements.

14. The method of claim 13, wherein:

the first tracking face geometrical data includes data indicative of expected relative positions of the plurality of optical tracking elements on the first tracking face and an expected direction of facing of the plurality of optical tracking elements on the first tracking face, and the second tracking face geometrical data includes data indicative of the expected relative positions of the plurality of optical tracking elements on the second tracking face and an expected direction of facing of the plurality of optical tracking elements on the second tracking face.

15. The method of claim 13, further comprising displaying calibration instructions based on the step of identifying the tracking array.

16. The method of claim 15, wherein the step of displaying calibration instructions further comprises displaying graphics that indicate to a user to rotate the tracking array relative to the localizer such that the at least one optical tracking element of the first tracking face and at least one optical tracking element of the second tracking face are visible to the localizer at the same time.

17. The method of claim 15, wherein the step of identifying includes comparing the detected direction of facing of the plurality of optical tracking elements, the expected direction of facing of the plurality of optical tracking elements on the first tracking face, and the expected direction of facing of the plurality of optical tracking elements on the second tracking face.

18. The method of claim 11, further comprising assigning the tracking array to a medical instrument by associating the composite rigid body to the medical instrument.

19. The method of claim 18, further comprising identifying the medical instrument based on associating the composite rigid body to the medical instrument.

20. The method of claim 11, wherein:

the tracking array further includes a third tracking face;

the first tracking face, the second tracking face, and the third tracking face collectively including the plurality of optical tracking elements; and the method further comprises:

detecting a facing direction of the plurality of optical tracking elements while the plurality of optical tracking elements are visible to the localizer;

measuring relative positions of the plurality of optical tracking elements while the plurality of optical tracking elements are visible to the localizer;

grouping the plurality of optical tracking elements into a first rigid body, a second rigid body, and a third rigid body based on the measured relative positions and facing direction of the plurality of optical tracking elements, each of the first rigid body, the second rigid body, and the third rigid body including at least one tracking element;

measuring relative positions of the at least one optical tracking element of the first tracking face or at least one optical tracking element of the second tracking face, and at least one optical tracking element of the third tracking face while visible to the localizer; and creating the composite rigid body based on the first rigid body, the second rigid body, and the third rigid body and the measured relative positions of at least one optical tracking element of the first tracking face, the at least one optical tracking element of the second tracking face, and the at least one optical tracking element of the third tracking face.

* * * * *